US009883812B2

(12) United States Patent
Huang et al.

(10) Patent No.: US 9,883,812 B2
(45) Date of Patent: Feb. 6, 2018

(54) ENHANCED MULTI-CORE BEAMFORMER ALGORITHM FOR SENSOR ARRAY SIGNAL PROCESSING BY COMBINING DATA FROM MAGNETOENCEPHALOGRAPHY

(75) Inventors: Ming-Xiong Huang, San Diego, CA (US); Roland R. Lee, San Diego, CA (US); Mithun Diwakar, San Diego, CA (US); Omer Tal, San Diego, CA (US); Thomas T. Liu, San Diego, CA (US)

(73) Assignees: The Regents of the University of California, Oakland, CA (US); U.S. Department of Veterans Affairs, Washington, DC (US)

( * ) Notice: Subject to any disclaimer, the term of this patent is extended or adjusted under 35 U.S.C. 154(b) by 1229 days.

(21) Appl. No.: 13/807,690

(22) PCT Filed: Jun. 28, 2011

(86) PCT No.: PCT/US2011/042258
§ 371 (c)(1),
(2), (4) Date: Mar. 28, 2013

(87) PCT Pub. No.: WO2012/006129
PCT Pub. Date: Jan. 12, 2012

(65) Prior Publication Data
US 2013/0204114 A1    Aug. 8, 2013

Related U.S. Application Data

(60) Provisional application No. 61/359,273, filed on Jun. 28, 2010, provisional application No. 61/454,347, filed on Mar. 18, 2011.

(51) Int. Cl.
*A61B 5/00* (2006.01)
*A61B 5/04* (2006.01)
(Continued)

(52) U.S. Cl.
CPC ........ *A61B 5/04008* (2013.01); *A61B 5/0059* (2013.01); *A61B 5/0476* (2013.01);
(Continued)

(58) Field of Classification Search
None
See application file for complete search history.

(56) References Cited

U.S. PATENT DOCUMENTS 5,263,488 A     11/1993   Van Veen et al.
5,269,325 A  *  12/1993   Robinson ........... A61B 5/04005
                                                        324/248
(Continued)

OTHER PUBLICATIONS

Popescu et al, Spatio-Temporal Reconstruction of Bilateral Auditory Steady-State Responses Using MEG Beamformers, IEEE Transactions on Biomedical Engineering, vol. 55, No. 3, Mar. 2008.*

(Continued)

*Primary Examiner* — Serkan Akar
(74) *Attorney, Agent, or Firm* — Perkins Coie LLP

(57) ABSTRACT

Techniques and systems are disclosed for implementing multi-core beamforming algorithms. In one aspect, a method of implementing a beamformer technique includes using a spatial filter that contains lead-fields of two simultaneous dipole sources rather than a linear combination of the two to directly compute and obtain optimal source orientations and weights between two highly-correlated sources.

8 Claims, 22 Drawing Sheets

(51) Int. Cl.
    A61B 5/0476    (2006.01)
    A61B 5/05      (2006.01)
(52) U.S. Cl.
    CPC .............. *A61B 5/05* (2013.01); *A61B 5/4088* (2013.01); *A61B 5/7282* (2013.01)

(56) References Cited

U.S. PATENT DOCUMENTS

| | | |
|---|---|---|
| 6,697,660 B1 | 2/2004 | Robinson |
| 2009/0182220 A1* | 7/2009 | Blunt .................... G06T 11/006 600/409 |

OTHER PUBLICATIONS

Sekihara et al "Localization bias and spatial resolution of adaptive and non-adaptive spatial filters for MEG source reconstruction", Neuroimage May 1, 2005; 25(4): 1056-1067.*

Aine, C., Huang, M., Stephen, J., Christner, R., 2000. Multistart algorithms for MEG empirical data analysis reliably characterize locations and time courses of multiple sources. NeuroImage 12, 159-172.

Auranen, T., Nummenmaa, A., Hamalainen, M.S., Jaaskelainen, I.P., Lampinen, J., Vehtari, A., Sams, M., 2005. Bayesian analysis of the neuromagnetic inverse problem with I(p)-norm priors. NeuroImage 26, 870-884.

Brookes, M.J., Stevenson, C.M., Barnes, G.R., Hillebrand, A., Simpson, M.I.G., Francis, S.T., Morris, P.G., 2007. Beamformer reconstruction of correlated sources using a modified source model. NeuroImage 34, 1454-1465.

Dalal, S.S., Sekihara, K., Nagarajan, S.S., 2006. Modified Beamformers for Coherent Source Region Suppression. IEEE Trans. Biomed. Eng. 53, 1357-1363.

Dale, A.M., Halgren, E., 2001. Spatiotemporal mapping of brain activity by integration of multiple imaging modalities. Curr. Opin. Neurobiol. 11, 202-208.

Dale, A.M., Fischl, B., Sereno, M.I., 1999. Cortical surface-based analysis: I. Segmentation and surface reconstruction. NeuroImage 9, 179-194.

Dale, A.M., Liu, A.K., Fischl, B.R., Buckner, R.L., Belliveau, J.W., Lewine, J.D., Halgren, E., 2000. Dynamic statistical parametric mapping: combining fMRI and MEG for high-resolution imaging of cortical activity. Neuron 26, 55-67.

Diwakar, M., Huang, M.X., Srinivasan, R., Harrington, D.L., Robb, A., Angeles, A., Muzzatti, L., Pakdaman, R., Song., T., Theilmann, R.J., Lee, R.R., 2011. Dual-Core Beamformer for obtaining highly correlated neuronal networks in MEG. NeuroImage 54, 253-263.

Fischl, B., van der, K.A., Destrieux, C., Halgren, E., Segonne, F., Salat, D.H., Busa, E., Seidman, L.J., Goldstein, J., Kennedy, D., Caviness, V., Makris, N., Rosen, B., Dale, A.M., 2004. Automatically parcellating the human cerebral cortex. Cereb. Cortex 14, 11-22.

Hamalainen, M.S., Ilmoniemi, R.J., 1994. Interpreting magnetic fields of the brain: minimum norm estimates. Med. Biol. Eng. Comput. 32, 35-42.

Hanlon, F.M., Weisend, M.P., Huang, M., Lee, R.R., Moses, S.N., Paulson, K.M., Thoma, R.J., Miller, G.A., Canive, J.M., 2003. A non-invasive method for observing hippocampal function. NeuroReport 14, 1957-1960.

Herman, A.T., Wollbrink, A., Chau, W., Ishii, R., ross, B., Pantev, C., Determination of activation areas in the human auditory cortex by means of synthetic aperture magnetometry. NeuroImage 20 (2), 2003, 995-1005.

Huang, M., Aine, C., Davis, L., Butman, J., Christner, R., Weisend, M., Stephen, J., Meyer, J., Silveri, J., Herman, M., Lee, R.R., 2000. Sources on the Anterior and Posterior Banks of the Central Sulcus Identified from Magnetic Somatosensory Evoked Responses using Multi-start Spatio-Temporal Localization. Human Brain Mapping. 11(2), 59-76.

Huang, M., Aine, C.J., Supek, S., Best, E., Ranken, D., Flynn, E.R., Multistart downhill simplex method for spatio-temporal source localization in magnetoencephalography. Electroencephalogr. Clin. Neurophysiol. 108, 1998. 32-44.

Huang, M., Dale, A.M., Song, T., Halgren, E., Harrington, D.L., Podgorny, I., Canive, J.M., Lewis, S., Lee, R.R., Vector-based spatial-temporal minimum L1-norm solution for MEG. NeuroImage 31, 2006, 1025-1037.

Huang, M., Davis, L.E., Aine, C., Wisend, M., Harrington, D., Christner R., Stephen, J., Edgar, J.C., Herman, M., Meyer, J., Paulson, K., Martin K., Lee, R.R., 2004. MEG response to median nerve stimulation correlates with recovery of sensory and motor function after stroke. Clin. Neurophysiol. 115, 820-833.

Huang, M.X., Harrington, D.L., Paulson, K.M., Weisend, M.P., Lee, R.R., 2004. Temporal dynamics of ipsilateral and contralateral motor activity during voluntary finger movement. Hum. Brain Mapp. 23, 26-39.

Huang, M.X., Lee, R.R., Gaa, K.M., Song, T., Harrington, D.L., Loh, C., Theilmann, R.J., Edgar, J.C., Miller, G.A., Canive, J.M., Granholm, E., 2010. Somatosensory System Deficits in Schizophrenia Revealed by MEG during a Median-Nerve Oddball Task. Brain Topography 23 (1), 82-104.

Huang, M.X., Lee, R.R., Miller, G.A., Thoma, R.J., Hanlon, F.M., Paulson, K.M., Martin, K., Harrington, D.L., Weisend, M.P., Edgar, J.C., Canive, J.M., 2005. A parietal-frontal network studied by somatosensory oddball MEG responses, and its cross-modal consistency. NeuroImage 28, 99-114.

Hui, H.B., Leahy, R.M., 2006. Linearly constrained MEG beamformers for MVAR modeling of cortical interactions. 3rd IEEE International Symposium on Biomedical Imaging: Nano to Macro, 2006, pp. 237-240.

Hui, H.B., Pantazis, D., Bressler, S.L., Leahy, R.M., 2010. Identifying true cortical interactions in MEG using the nulling beamformer. NeuroImage 49, 3161-3174.

Kim, S., Lee, C., Kang, H., 2006. Optimum beamformer in correlated source environments. J. Acoust. Soc. Am. 120 (6), 3770-3781.

Liljestrom, M., Kujala, J., Jensen, O., Salmelin, R., 2005. Neuromagnetic localization of rhythmic activity in the human brain: a comparison of three methods. NeuroImage 25, 734-745.

Marinkovic, K., Dhond, R.P., Dale, A.M., Glessner, M., Carr, V., Halgren, E., 2003. Spatiotemporal dynamics of modality-specific and supra-modal word processing. Neuron 38, 487-497.

Mosher, J.C., Baillet, S., Leahy, R.M., 1999. EEG source localization and imaging using multiple signal classification approaches. J. Clin. Neurophsiol. 16, 255-238.

Mosher, J.C., Leahy, R.M., 1998. Recursive MUSIC: a framework for EEG and MEG source localization. IEEE Trans. Biomed. Eng. 45, 1342-1354.

Mosher, J.C., Lewis, P.S., Leahy, R.M., 1992. Multiple dipole modeling and localization from spatio-temporal MEG data. IEEE Trans. Biomed. Eng. 39, 541-557.

Nguyen, T., Ding, Z., 1997. CMA beamforming for multipath correlated sources. IEEE International Conference on Acoustics, Speech, and Signal Processing 3, 2521-2524.

Osipova, D., Ahveninen, J., Jensen, O., Ylikoski, A., Pekkonen, E., 2005. Altered generation of spontaneous oscillations in Alzheimer's disease. NeuroImage 27, 835-841.

Pulvermuller, F., Shtyrov, Y., Ilmoniemi, R., 2003. Spatiotemporal dynamics of neural language processing: an MEG study using minimum-norm current estimates. NeuroImage 20, 1020-1025.

Quuran, M.A., Cheyne, D., 2010. Reconstruction of correlated brain activity with adaptive spatial filters in MEG. NeuroImage 49, 2387-2400.

Robinson, S., Vrba, J., 1998. Functional neuroimaging by synthetic aperture magnetometry. In: Yoshimoto, T., Kotani, M., Kuriki, S., Karibe, H., Nakasato, N. (Eds.), Recent Advances in Biomagnetism. Tohoku Univ. Press, Sendai, pp. 302-305.

Ross, B., Herdman, A.T., Pantev, C., 2005. Right hemispheric laterality of human 40 Hz auditory steady-state responses. Cereb. Cortex 15 (12), 2029-2039.

Sekihara, K., Nagarajan, S., Poeppel, D., Marantz, A., 2002. Performance of an MEG adaptive-beamformer technique in the pres-

(56) References Cited

OTHER PUBLICATIONS ence of correlated neural activities: effects on signal intensity and time course estimates. IEEE Trans. Biomed. Eng. 49 (12), 1534-1546.
Sekihara, K., Nagarajan, S., Poeppel, D., Marantz, A., 2004. Asymptotic SNR of scalar and vector minimum-variance beamformers for neuromagnetic source reconstruction. IEEE Trans. Biomed. Eng. 51 (10), 1726-1733.
Sekihara, K., Nagarajan, S., Poeppel, D., Marantz, A., Miyashita, Y.M., 2002. Application of an MEG eigenspace beamformer to reconstructing spatio-temporal activities of neural sources. Hum. Brain Mapp. 15, 199-215.
Shih, J.J., Weisend, M.P., Davis, J.T., Huang, M., 2000. Magnetoencephalographic characterization of sleep spindles in humans. J. Clin. Neurophysiol. 17, 224-231.
Simpson, M.I.G., Hadjipapas, A., Barnes, G.R., Furlong, P.L., Witton, C., 2005. Imaging the dynamics of the auditory steady-state evoked response. Neurosci. Lett. 16 (3), 195-197.
Song, T., Cui, L., Gaa, K., Feffer, L., Taulu, S., Lee, R.R., Huang, M.X., 2009. Signal Space Separation Algorithm and Its Application on Suppressing Artifacts Caused by Vagus Nerve Stimulation for Magnetoencephalography Recordings. J. Clin. Neurophysiol. 26 (6), 392-400.
Song, T., Gaa, K., Cui, L., Feffer, L., Lee, R.R., Huang, M.X., 2008. Evaluation of signal space separation via simulation. Med. Biol. Eng. Comput. 46, 923-932.
Stenbacka, L., Vanni, S., Uutela, K., Hari, R., 2002. Comparison of minimum current estimate and dipole modeling in the analysis of simulated activity in the human visual cortices. NeuroImage 16, 936-943.
Stephen, J.M., Aine, C.J., Christner, R.F., Ranken, D., Huang, M., Best, E., 2002. Central versus peripheral visual field stimulation results in timing differences in dorsal stream sources as measured with MEG. Vision Res. 42, 3059-3074.
Stephen, J.M., Davis, L.E., Aine, C.J., Ranken, D., Herman, M., Hudson, D., Huang, M., Poole, J., 2003. Investigation of the normal proximal somatomotor system using magnetoencephalography. Clin. Neurophysiol. 114, 1781-1792.
Taulu, S., Kajola, M., Simola, J., 2004. Suppression of interference and artifacts by the signal space separation method. Brain Topogr. 16, 269-275.
Taulu, S., Simola, J., 2006. Spatiotemporal signal space separation method for rejecting nearby interference in MEG measurements. Phys. Med. Biol. 51, 1759-1768.
Tesche, C., 2000. Evidence for somatosensory evoked responses in human temporal lobe. NeuroReport 11, 2655-2658.
Uutela, K., Hamalainen, M., Somersalo, E., 1999. Visualization of magnetoencephalographic data using minimum current estimates. NeuroImage 10, 173-180.
Van Drongelen, W., Yuchtman, M., Van Veen, B.D., Van Huffelen, A.C., 1996. A spatial filtering technique to detect and localize multiple sources in the brain. Brain Topogr. 9 (1), 39-49.
Van Veen, B.D., Van Drognelen, W., Yuchtman, M., Suzuku, A., 1997. Localization of brain electrical activity via linearly constrained minimum variance spatial filtering. IEEE Trans. Biomed. Eng. 44 (9).
Vanni, S., Uutela, K., 2000. Foveal attention modulates responses to peripheral stimuli. J. Neurophysiol. 83, 2443-2452.
International Search Report and Written Opinion of International Application No. PCT/US2011/042258; dated Feb. 29, 2012; 9 pages.
Hillebrand, A., Singh, K.D., Holliday, I.E., Furlong, P.L., Barnes, G.R., 2005. A new approach to neuroimaging with Magnetoencephalography. Hum. Brain Mapp. 25, 199-211.
Kumihashi, I., Sekihara, K., 2010. Array-gain constraint minimum-norm spatial filter with recursively updated gram matrix for biomagnetic source imaging. IEEE Trans. Biomed. Eng. 57, 1358-1365.
Spencer, M.E., Leahy, R.M., Mosher, J.C., Lewis, P.S., 1992. Adaptive filters for monitoring localized brain activity from surface potential time series. Conf. Record for 26thAnnu.Asilomer Conf. Signals, Systems, and Computers.156-161.
Vrba, J., Robinson, S.E., 2001. Signal processing in magnetoencephalography. Methods 25 (2), 249-271.
Popescu, et al., Spatio-Temporal Reconstrution of Bilateral Auditory Steady-State Responses Using MEG Beamformers, IEEE Transactions on Biomedical Engineering, vol. 55, No. 3, Mar. 2008.

\* cited by examiner

FIG. 1A-G

ENHANCED MULTI-CORE BEAMFORMER ALGORITHM FOR SENSOR ARRAY SIGNAL PROCESSING BY COMBINING DATA FROM MAGNETOENCEPHALOGRAPHY

CROSS REFERENCE TO RELATED APPLICATIONS

This international patent application claims priority to U.S. Provisional Patent Application No. 61/359,273, filed Jun. 28, 2010, and U.S. Provisional Patent Application No. 61/454,347, filed Mar. 18, 2011. The entire contents of the before-mentioned patent applications are incorporated by reference as part of the disclosure of this application.

STATEMENT REGARDING FEDERALLY SPONSORED RESEARCH OR DEVELOPMENT

This invention was made with government support under N00141010072 awarded by Office of Naval Research. The government has certain rights in the invention.

BACKGROUND

This application relates to devices and techniques that use medical imaging technologies.

Magnetoencephalography (MEG) is a functional imaging modality that directly detects neuronal activity. Because a number of different source configurations can generate the same MEG signal, assumptions are made about the nature of the sources (source models) to uniquely localize them. Conventional MEG source-modeling methods require a priori information when localizing highly-correlated networks from noisy MEG data.

The beamformer methodology is a spatial-filtering approach where the MEG sensor signal is filtered by different beams based on lead-field vectors corresponding to specific source-grid points. Each of these operations generates a pseudo-Z-statistic, which can be maximized to find the most highly-contributing source-grid dipoles. The beamformer method has low computational cost, although the orientation angle of each dipole must be optimized. The beamformer approach generally works well for MEG data with a low SNR. However, the conventional beamformer suppresses source-power estimates from source-grid dipoles that have highly correlated time-courses, as the method assumes that source time-courses from different generators are uncorrelated. Variants of the beamformer method, including the coherently combining signal-to-interference plus noise ratio (CC-SINR) beamformer and the constant modulus algorithm (CMA) beamformer, address reconstruction of correlated sources, but have been met with moderate success. Likewise, the coherent source suppression model (CCSM) and the independently developed nulling beamformer (NB) accurately reconstruct correlated sources but require a priori information of interfering source locations. Furthermore, entire unknown pathways of neural activity cannot be easily identified since correlated sources are suppressed to reconstruct a single source of interest.

SUMMARY

Techniques and systems and apparatus are disclosed for implementing "Multi-Core Beamformer" (MCBF), a lead-field based inverse-modeling technique designed for simultaneously reconstructing highly-correlated and uncorrelated sources from noisy sensor array data.

In one aspect, a method of implementing an enhanced beamformer technique includes reconstructing a source power covariance matrix $R_s$ between multiple sources to determine individual time-courses and correlations for sources in low SNR conditions.

Implementations can optionally include one or more of the following features. The enhanced beamformer technique can include an enhanced dual-core beamformer (eDCBF) technique. The eDCBF can use a single computation of a weight matrix for accurate correlation determination. The eDCBF weighting matrix can be defined as the m×4 matrix $W_d = [W_1 \ W_2]$, where $W_i$ are the individual weighting matrices for each source, ensuring no reduction in rank and enabling the computation of unique source time-courses and correlation. The beamformer technique can include an enhanced multi-core beamformer (eMCBF) reconstruction. The eMCBF can include detecting an orientation (direction) of signals to allow correlation and reconstruction of multiple interfering sources at the same time.

In another aspect, a method of implementing a beamformer technique can include using a spatial filter that contains lead-fields of two simultaneous dipole sources rather than a linear combination of the two to directly compute and obtain optimal source orientations and weights between two highly-correlated sources.

Implementations can optionally include one or more of the following features. For example, a magnetoencephalography (MEG) inverse-modeling technique can be used to reduce a computational time. The MEG inverse-modeling technique can cause non-linear optimization and non-linear searching for optimal orientations and weighting to be unnecessary. A modified Powell search can be used to find the optimal pseudo-Z-score to reduce the computational time required for source localization and identify other local maxima that can be interpreted as secondary correlated pathways.

In another aspect, described is a method of implementing a multi-core beamformer (MCBF) lead-field based inverse-modeling technique designed for simultaneously reconstructing highly-correlated and uncorrelated sources from noisy sensor array data.

Implementations can optionally include one or more of the following features. The MCBF can be used to reconstruct source positions, time-courses, and correlations. The MCBF can be used to localize abnormal neuronal networks using data from magnetoencephalography (MEG) to provide more sensitive diagnosis than conventional neuroimaging techniques for neurological and psychiatric disorders comprising at least one of 1) traumatic brain injury (TBI), 2) stroke, 3) Post-Traumatic Stress Disorder (PTSD), 4) schizophrenia, 5) Alzheimer's dementia, or 6) Autism. The MCBF can be used to recover source information from any types of sensor arrays, including radar, sonar, astronomical telescopes, magnetotelluric sensors, optical and other electromagnetic arrays.

The methods described in this document can be implemented using a system. For example, a system can include an imaging device to obtain an image signal; and a computing device to receive the image signal from the imaging device to reconstruct, based on the obtained image signal, a source power covariance matrix $R_s$ between multiple sources to determine individual time-courses and correlations for sources in low SNR conditions. The computing device can be configured to perform an enhanced beamformer technique on the obtained image signal.

Implementations can optionally include one or more of the following features. The enhanced beamformer technique can include an enhanced dual-core beamformer (eDCBF) technique. The eDCBF can use a single computation of a weight matrix for accurate correlation determination. The eDCBF weighting matrix can be defined as the m×4 matrix $W_d=[W_1\ W_2]$, where $W_i$ are the individual weighting matrices for each source, ensuring no reduction in rank and enabling the computation of unique source time-courses and correlation. The beamformer technique can include an enhanced multi-core beamformer (eMCBF) reconstruction. The eMCBF can include detecting an orientation (direction) of signals to allow correlation and reconstruction of multiple interfering sources at the same time.

In another aspect a system can include an imaging device to obtain an image signal; and a computing device to receive the image signal from the imaging device to perform a beamformer technique on the received image signal. The computing device is configured to perform the beam former technique including: using a spatial filter that contains lead-fields of two simultaneous dipole sources rather than a linear combination of the two to directly compute and obtain optimal source orientations and weights between two highly-correlated sources.

Implementations can optionally include one or more of the following features. The computing device can be configured to use a magnetoencephalography (MEG) inverse-modeling technique to reduce a computational time. The MEG inverse-modeling technique can cause non-linear optimization and non-linear searching for optimal orientations and weighting to be unnecessary. The computing device can be configured to use a modified Powell search to find the optimal pseudo-Z-score to reduce the computational time required for source localization and identify other local maxima that can be interpreted as secondary correlated pathways.

In another aspect, a system can include an imaging device to obtain an image signal; and a computing device to receive the image signal from the imaging device to perform on the received image signal a multi-core beamformer (MCBF) lead-field based inverse-modeling technique designed for simultaneously reconstructing highly-correlated and uncorrelated sources from noisy sensor array data.

Implementations can optionally include one or more of the following features. The computing device can be configured to use the MCBF to reconstruct source positions, time-courses, and correlations. The computing device can be configured to use the MCBF to localize abnormal neuronal networks using data from magnetoencephalography (MEG) to provide more sensitive diagnosis than conventional neuroimaging techniques for neurological and psychiatric disorders comprising at least one of 1) traumatic brain injury (TBI), 2) stroke, 3) Post-Traumatic Stress Disorder (PTSD), 4) schizophrenia, 5) Alzheimer's dementia, or 6) Autism. The computing device can be configured to use the MCBF to recover source information from any types of sensor arrays, including radar, sonar, astronomical telescopes, magnetotelluric sensors, optical and other electromagnetic arrays.

The subject matter described in this specification potentially can provide one or more of the following advantages. For example, the described MCBF algorithm can automatically calculate optimal amplitude-weighting, source orientations, and correlations for reconstruction for two or more sources, reducing the computational time of the dual-beamformer technique by a factor of 100. The MCBF can handle both correlated and uncorrelated sources, unlike the conventional beamformer and the dual-beamformer. Furthermore, the described MCBF can also include the paradigm and strategy of how to apply the new MCBF to obtain neuroimaging-based evidence for better diagnosing and monitoring different neurological and psychiatric disorders.

In addition, the described eMCBF techniques can be used to explore the active neuronal sources underlying magnetoencephalography (MEG) recordings at low signal-to-noise ratio (SNR). The described enhanced multi-core beamforming (eMCBF) and enhanced dual-core beamformer (eDCBF) techniques can be used to localize uncorrelated neuronal sources under poor SNR conditions. Also, the described eMCBF and eDCBF techniques can be used even when sources are correlated, which is a common and important property of real neuronal networks. In addition, the described eMCBF and eDCBF techniques can be used to produce individual time-courses and quantify source correlation. The described enhanced formulation of dual-core beamformer (DCBF) approach can reconstruct individual source time-courses and their correlations. Through computer simulations, it can be shown that the enhanced DCBF (eDCBF) can consistently and accurately model dual-source activity regardless of the correlation strength. Simulations also show that a multi-core extension of eDCBF can effectively handle the presence of additional correlated sources. In a human auditory task, we further demonstrate that eDCBF can accurately reconstruct left and right auditory temporal responses and their correlations. Spatial resolution and source-localization strategies corresponding to different measures within the eDCBF framework are also discussed. In summary, eDCBF can accurately reconstruct source spatio-temporal behavior, providing a means for characterizing complex neuronal networks and their communication.

BRIEF DESCRIPTION OF THE DRAWINGS

Like reference symbols and designations in the various drawings indicate like elements.

DETAILED DESCRIPTION

Figure 1:
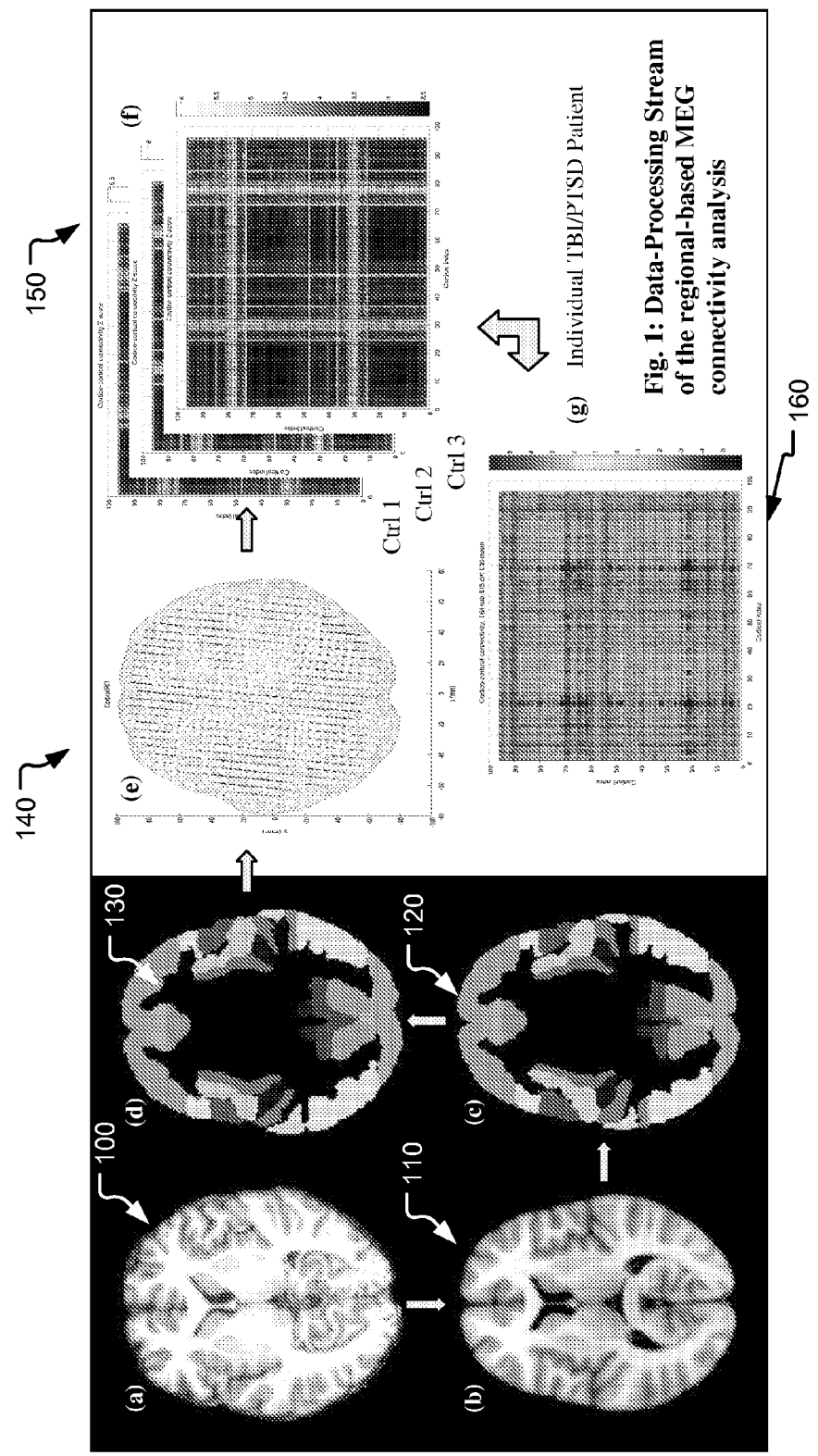
FIGS. 1A-G show data-Processing Stream of the regional-based MEG connectivity analysis.

The techniques, apparatus and systems described in this application can be used to implement "Multi-Core Beamformer" (MCBF), a new lead-field based inverse-modeling technique designed for simultaneously reconstructing highly-correlated and uncorrelated sources from noisy sensor array data. The MCBF is capable of reconstructing source positions, time-courses, and correlations. This novel algorithm can be used to localize abnormal neuronal networks using data from (but not limited to) magnetoencephalography (MEG) to provide more sensitive diagnosis than conventional neuroimaging techniques (e.g., CT and MRI) for a variety of neurological and psychiatric disorders such as: 1) traumatic brain injury (TBI), 2) stroke, 3) Post-Traumatic Stress Disorder (PTSD), 4) schizophrenia, 5) Alzheimer's dementia, and 6) Autism. MCBF can also be used to recover source information from any types of sensor arrays, including radar, sonar, astronomical telescopes, magnetotelluric sensors, optical and other electromagnetic arrays, and others.

Multi-Core Beamformer (MCBF)

Sensor arrays are used widely in the fields of science and mathematics. Sensor arrays provide greater information about signal-generating sources and can be used to find locations and time-courses of these signals. For example, the beamformer spatial filter is a method by which the lead-field approach of MEG is used to estimate neuronal current sources in the brain. The lead-field approach states that for a given set of current dipole sources, the MEG sensor readings can be described by a linear combination of the source signals. The relationship between MEG sensor signals and source time-courses can be expressed using a general sensor array equation 1:

$$b(t) = G \cdot p(t) \qquad (1)$$

b(t): matrix of sensor signals (m×t), e.g., an m dimensional column vector of m MEG sensor signals for the same temporal range;
p(t): matrix of source signals (3p×t), e.g., a 3p dimensional column vector of p source signals in 3 principle orientations;
G: gain matrix (m×3p), or lead-field matrix, estimated by MEG forward modeling for the MEG sensor grid;
m: number of sensors;
t: number of time-points; and
s: number of sources The rows of p(t) contain the source signals in each principal direction (3 total), allowing for a vector description of the source signals. Once sensor recordings are taken, the problem becomes to determine the gain matrix G and the source signal matrix p(t).

G can be found with an appropriate forward modeling algorithm for the system of interest. For example, the radar response to aircraft at various positions can be determined to construct the gain matrix for a given grid of sources. Other examples include sonar arrays deployed in the ocean or elsewhere; or telescope arrays for astronomical data collection; or magnetotelluric arrays for geologic exploration for water, oil, or minerals in the earth; etc.

The lead-field vector ($L_p$) for each of p source dipoles is defined as the three columns of G that correspond to the specific source dipole. Besides the lead-field vector, C, an m×m signal covariant matrix computed from b(t), and $\epsilon$, an m×m noise covariance matrix computed from noise-only MEG signal are also used to construct the beamformer (Van Veen et al., 1997). In order to compute the source power, orientation, and estimated neuronal activity for a dipole, the matrices Q and K must first be defined (Robinson and Vrba, 1998; Vrba and Robinson, 2001; Sekihara et al., 2004).

$$Q = (L_p^T \cdot C^{-1} \cdot L_p) \quad (2)$$

$$K = (L_p^T \cdot C^{-1} \cdot L_p)^{-1} \cdot (L_p^T \cdot (C^{-1} \cdot \epsilon C^{-1}) \cdot L_p) \quad (3)$$

Q is inversely proportional to the source power. It has been shown that the optimal power may be obtained by inverting the minimum eigenvalue of Q (Sekihara et al., 2004):

$$P_{opt} = (\min(\text{eig}(Q)))^{-1} \quad (4)$$

The optimal source orientation is therefore given by $U_{min}$, the three-component eigenvector corresponding to the minimum eigenvalue of Q:

$$O_{opt} = U_{min} \quad (5)$$

K is inversely proportional to the signal-to-noise ratio in source space. The estimated neuronal activity or pseudo-Z-score may be obtained by diagonalizing K with eigenvalue decomposition and inverting the smallest eigenvalue:

$$Z_{opt} = (\min(\text{eig}(K)))^{-1} \quad (6)$$

Z is a measure of the signal-to-noise ratio in the source space. The reconstructed source signal from a particular dipole is given by:

$$p(t) = O_{opt} \cdot (P_{opt} \cdot C^{-1} \cdot L_p \cdot O_{opt}) \cdot b(t) \quad (7)$$

In essence, the beamformer is a method wherein the signal is spatially filtered by the lead-field vectors to find the source location with maximum activity using a scanning approach over a pre-specified source grid with thousands of nodes (potential source locations). In the vector formulation, the optimal source power, orientation, and pseudo-Z-score may be computed with eigenvalue analysis. In the scalar formulation, the optimal dipole orientation must first be found using a search. However, the scalar and vector beamformer formulations have been shown to be mathematically equivalent.

Previous Dual Beamformer Solution (General Approach)

The single beamformer approach, as described above, has an important limitation when spatially distinct yet temporally-correlated sources are present in the MEG signal (Van Veen et al., 1997). Different modifications of the single beamformer approach attempt to compensate for this limitation (Kim et al., 2006; Nguyen and Ding, 1997; Brookes et al., 2007). Brookes et al. developed the dual beamformer approach specifically for reconstructing correlated sources. In this approach, a new lead-field vector is computed based on the linear combination of the two lead-field vectors from two particular source dipoles as follows:

$$L_{dual} = \alpha L_{\theta 1} + (1-\alpha) L_{\theta 2} \quad (8)$$

$L_{\theta 1}$ and $L_{\theta 2}$ are the lead-fields of the two source dipoles rotated to the orientations specified by $\theta_1$ and $\theta_2$, respectively. The relative dipole weights are specified by $\alpha$, the weighting parameter. The pseudo-Z-statistic and reconstructed source signal are recovered in an identical manner to the scalar single beamformer method. However, to find the optimal pseudo-Z-score, both orientation angles and the weighting parameter $\alpha$ must also be optimized non-linearly. Using this method, only a single signal is recovered for both dipoles. The relative weighting of these signals can be estimated by the optimized weighting parameter $\alpha_{opt}$. Due to the time-consuming nature of non-linear optimizing over these parameters, computing pseudo-Z-scores for every combination of current dipoles is not time-efficient. Thus, the use of other sources of information (e.g., fMRI) is suggested to fix one of the two dipoles in an a priori fashion, which reduces the computational needs of the dual-beamformer method (Brookes et al., 2007).

Conventional beamformer techniques can solve the signal equation for p(t) of a single source at a time. However, if sources are correlated, the conventional beamformer output power drops dramatically and the algorithm fails. The MCBF approach detailed below succeeds in reconstructing correlated and uncorrelated sources.

New Dual-Core Beamformer Approach (DCBF)

Previous dual-beamformer method requires optimization of the orientation of both beams and their relative weighting. Non-linear optimizations are used, which increase the computational complexity of the dual beamformer approach many-fold when compared to the single beamformer approach. In the new DCBF described in this document, the optimal orientations and weighting of both beams can be directly computed, instead of searched, by using a vector formulation of the dual beamformer approach.

To facilitate the description of the mathematics, the MCBF will first be described for two cores; and this approach is then generalized to N cores, where N is an integer greater than 2.

The process starts with a lead-field vector for each dipole as an m×3 matrix expressed in a pre-defined coordinate basis with three axes. Alternatively, since MEG is insensitive to radially-directed currents, the lead-field vector for each dipole can be decomposed by singular value decomposition (SVD) and expressed instead as an m×2 matrix to reduce the inverse problem to two spatial dimensions. A dual-core spatial filter can be construed including the 6 columns of the gain matrix associated with our two sources of interest. $L_1$ denotes the 3-column gain matrix corresponding to the first source, and $L_2$ denotes the 3-column gain matrix corresponding to the second source. The dual-core filter denoted $L_{dual}$ is given by equation 9 that defines the combined lead-field vectors from both dipoles in the dual beamformer as an m×6 matrix, instead of a linear combination of two lead-fields:

$$L_{dual} = [L_1 L_2] \quad (9)$$

The new $L_{dual}$ is therefore a spatial filter with two cores rather than one. Such a description of the spatial filter allows eigenvalue analysis to analytically determine optimal orientations of each beam and optimal weighting between each beam.

A matrix analogous to $Q_{dual}$ is defined for the single beamformer in (2) to estimate the source powers and orientations by constructing the $Q_{dual}$ matrix which is inversely proportional to source power:

$$Q_{dual} = L_{dual}^T C^{-1} L_{dual} \quad (10)$$

C: (m×m) covariant matrix of b(t)

By diagonalizing $Q_{dual}$ eigenvalue decomposition, the optimum beamformer power can be obtained along with the optimum orientations, and the optimum weighting of the two source dipoles as follows:

$$P_{opt}^{dual} = (\min(\text{eig}(Q_{dual})))^{-1} \quad (11)$$

$$O_{opt}^{dual} = U_{min} \quad (12)$$

$U_{min}$ is defined as the six-component eigenvector associated with the minimum eigenvalue of $Q_{dual}$. The first three elements of $O_{opt}^{dual}$ contain the optimal beam-1 weighting in the three different basis directions. The last three elements contain the optimal beam-2 weighting in its basis directions. The elements corresponding to beam 1 and the elements corresponding to beam 2 are scaled such that relative weighting between the beams is optimal.

The cost of computation is low because the eigenvalue decompositions are performed on matrices ($K_{dual}$ and $Q_{dual}$) with low dimensions (6 by 6). Since the DCBF is a vector formulation of the previous dual beamformer method, reconstructed dipole orientations and weighting should be the same for both methods. To examine the computational efficiency (speed) resulting from directly computing orientations and weights instead of performing a non-linear search, 100 direct computations and 100 Nelder-Mead non-linear simplex searches were performed and timed. The reconstructed time-course for the source dipoles is given by:

$$p(t) = O_{opt}^{dual} \cdot (P_{opt}^{dual} \cdot C^{-1} \cdot L_{dual} \cdot O_{opt}^{dual})^T \cdot b(t) \quad (13)$$

p(t), the source time-course, is a 6×t matrix whose first three rows comprise the time-course for the first source and whose last three rows comprise the time-course for the second source. Each row contains the component of the time-course along each axis. An assumption of signal reconstruction is that both signals are highly correlated. As a result, only one time-course is actually reconstructed. However, this time-course is weighted appropriately to generate a time-course for each component of each source.

Since the optimal weighting, orientations, and pseudo-Z-statistic are computed directly, the only parameter left to optimize is the specific combination of dipoles that leads to the maximum pseudo-Z-score. As noted before, this can be accomplished by an exhaustive brute-force search over all possible dipole combinations (Brookes et al., 2007). In this scenario, if p is the number of dipoles, one would have to compute p(p+1)/2 pseudo-Z-scores to find the best dipole combination. To circumvent the long computational time of a brute-force search, a priori information can be used to fix the location of one dipole. However, this method is not ideal when knowledge of sources is not widely accepted or is unavailable.

In the present study, a modified Powell search algorithm was implemented to find the best dipole combination without performing a brute-force calculation and without requiring a priori information. Let $[r_1, r_2]$ be the two coordinate axes on which the search is performed. The $r_1$ axis corresponds to the index of the first dipole in a given source grid, while $r_2$ corresponds to the index of the second dipole. Let the function that we are searching over be defined as:

$$f(r_1, r_2) = Z_{opt}^{dual}(r_1, r_2) \quad (14)$$

Suppose $r_1^0$ is a dipole picked randomly from a given source grid. The profile $f(r_1^0, r2)$ is calculated and then maximized to find the corresponding $r_2^{opt}$ value. Subsequently, the profile $f(r1, r_2^{opt})$ is calculated to find an optimized $r_1$ value. This process is repeated until stable $Z_{opt}^{dual}$, $r_1^{opt}$, and $r_2^{opt}$ are reached. Since this search may converge to a local maximum, the process may be iterated multiple times using random initializations of dipoles. In this manner, $r_1^{opt}$ and $r_2^{opt}$, or the optimal dipole combination can be reached more quickly than the brute-force method. In our reconstructions, the Powell search was also implemented with a taboo list to reduce computational time by interrupting the search every time a dipole combination that had already been traversed was selected again.

The results of all Powell search iterations (pairs of correlated dipoles) were saved as they represent local maxima of $Z_{opt}^{dual}$ that could correspond to different pathways of cortical activation or different highly-correlated networks that co-exist in the data.

The signal-to-noise ratio (SNR) for any given two sources is useful for localization purposes. Similar to the pseudo-Z-statistic computation for the single vector beamformer in (3) and (6), the 6×6 matrix $K_{dual}$ can be defined by constructing the $K_{dual}$ matrix which is inversely proportional to the SNR:

$$K_{dual} = (L_{dual}^T \cdot C^{-1} \cdot L_{dual})^{-1} \cdot (L_{dual}^T \cdot (C^{-1} \cdot \epsilon \cdot C^{-1}) \cdot L_{dual}) \quad (15)$$

$\epsilon$: (m×m) noise covariant matrix of $b_{noise}$ (t), a set of sensor noise recordings.

By diagonalizing $K_{dual}$ with eigenvalue decomposition and inverting the smallest eigenvalue, we obtain the best possible pseudo-Z-score for the two dipoles.

$$Z_{opt}^{dual} = (\min(\text{eig}(K_{dual})))^{-1} \quad (16)$$

This step is an extension of the approach used in the single beamformer. To determine source correlation, an optimized $Q_{dual}$ matrix can be constructed as follows:

$$L_{dual}^{opt} = [L_1 \cdot O_{opt}^{dual}(1:3) L_2 \cdot O_{opt}^{dual}(4:6)]$$

$$Q_{dual}^{opt} = (L_{dual}^{opt})^T \cdot C^{-1} \cdot L_{dual}^{opt}$$

$$\pi_{dual}^{opt} = (Q_{dual}^{opt})^{-1} \quad (17)$$

$\pi_{dual}^{opt}$: (2×2) source power covariant matrix

The correlation between the sources may then be determined by:

$$X_{12} = \frac{(\pi_{dual}^{opt}(1,2))^2}{\pi_{dual}^{opt}(1,1) \cdot \pi_{dual}^{opt}(2,2)} \quad (18)$$

$X_{12}$: correlation between sources 1 and 2
(1,2) refers to the off-diagonal component, whereas (1,1) and (2,2) refer to the diagonal components.

The source time-courses may be reconstructed as follows:

$$p(t) = \pi_{dual}^{opt} \cdot (C^{-1} \cdot L_{dual}^{opt})^T \cdot b(t) \quad (19)$$

All of the above mathematics is easily extended to multiple cores by adding additional terms into $L_{dual}$:

$$L_N = [L_1 L_2 \ldots L_N] \quad (20)$$

MCBF Regional Analysis

The above functional-connectivity analysis between two points (voxels) on the source grid (Eqs. 9-12 and 15-19) can be expanded for functional-connectivity analysis between two regions of interest (ROIs). This is particularly useful for assessing regional functional-connectivity across two standard ROIs in a human subject, for example. In this approach, the MRI from individual subjects will be registered to a standard brain atlas (e.g., using FSL (www.fmrib.ox.ac.uk/fsl/)) in which two ROI masks (e.g., two different Brodmann areas) will be obtained. Then, two ROIs in the standard atlas will be transferred back to the individual subject's imaging space, and only the grid nodes within these ROI masks are selected. Finally, the regional functional-connectivity can be calculated as the root-mean-square functional-connectivity index (either pseudo-Z-score or correlation) in Eqs. 9-12 and 15-19 among dipole pairs across the two ROI masks: one dipole in the first ROI and the other dipole in the second ROI. The Harvard-Oxford Atlas, as part of the FSL software (www.fmrib.ox.ac.uk.fsl/), with masks of 96 cortical regions (48 in each hemisphere) and 21 sub-cortical regions is currently implemented in the MCBF software package.

Data Processing Stream of Regional Connectivity Analysis Using MCBF for Clinical Diagnosis Described below is the theory of changing the functional-connectivity analysis from accessing all combinations of dipole pairs, to a small number of brain regions. Usually, the number of combinations for dipole pairs in the brain is quite large: for a grid of 5000 dipoles, the number of independent dipole pairs is ~12.5 million. Connectivity analysis with such a large number of combinations is difficult to interpret. Regional-based connectivity analysis is used to reduce the scale to a manageable level.

FIGS. 1a-g illustrate the data-processing stream of the regional-based MEG connectivity analysis: 1) The T1-weighted MR images from a subject (FIG. 1(a) 100) is registered to a standard atlas (e.g., MNI-152 as in FIG. 1(b) 110) using FSL. 2) The cortical (FIG. 1(c) 120) and sub-cortical masks with pre-defined brain regions from the standard atlas are transferred to the individual subject's coordinate (FIG. 1(d) 130), using the inverse of the transformation in the first step. The Harvard-Oxford Atlas, as part of the FSL software (www.fmrib.ox.ac.uk/fsl/) with masks of 96 cortical regions (48 in each hemisphere) and 21 sub-cortical regions, is used in this step. 3) The regional masks in this subject are down-sampled to a cubic grid with 5 mm size (FIG. 1(e) 140). Note that the color coding for different brain regions in this subplot is different from the one used in FIGS. 1(c),(d). The gray triangles are the boundary elements used to describe the boundary of the inner skull surface for MEG forward calculation. 4) The MEG regional-based functional-connectivity can be calculated as the root-mean-square (RMS) value of the pseudo-Z-score or correlation in Section 4A (Eqs. 6 and 8) among all dipole pairs across the two regions in the masks: one dipole in the first region and the other dipole in the second region. FIG. 1(f) 150 shows the regional connectivity maps among all 96 cortical regions (see an example in next section for details). By repeating the above procedure in all healthy control subjects, a normative data base can be established. 5) For a given TBI patient, his/her regional connectivity map is compared with the normative database and the regions that show abnormal connectivity are detected (FIG. 1(g) 160).

How MCBF can be Used to Help the Diagnosis of Different Neurological and Psychiatric Disorders Neurological and psychiatric disorders will show abnormal functional connectivity among different brain areas which can be measured accurately by MCBF using MEG. Traumatic brain injury, stroke, Alzheimer's dementia, Autism, and schizophrenia cause reduction of the functional connectivity among different brain areas, whereas post-traumatic stress disorder (PTSD) causes hyper-activity with abnormally enhanced connectivity in a neuronal network that includes the amygdala, hippocampus, para-hippocampal cortex, and cingulate cortex. Such abnormally reduced and enhanced functional connectivity in the source (brain) space can be used as imaging-markers for diagnosing the above disorders, and for monitoring their responses to therapeutic interventions.

Computer Simulations that Document the Performance of the MCBF

Figure 2:
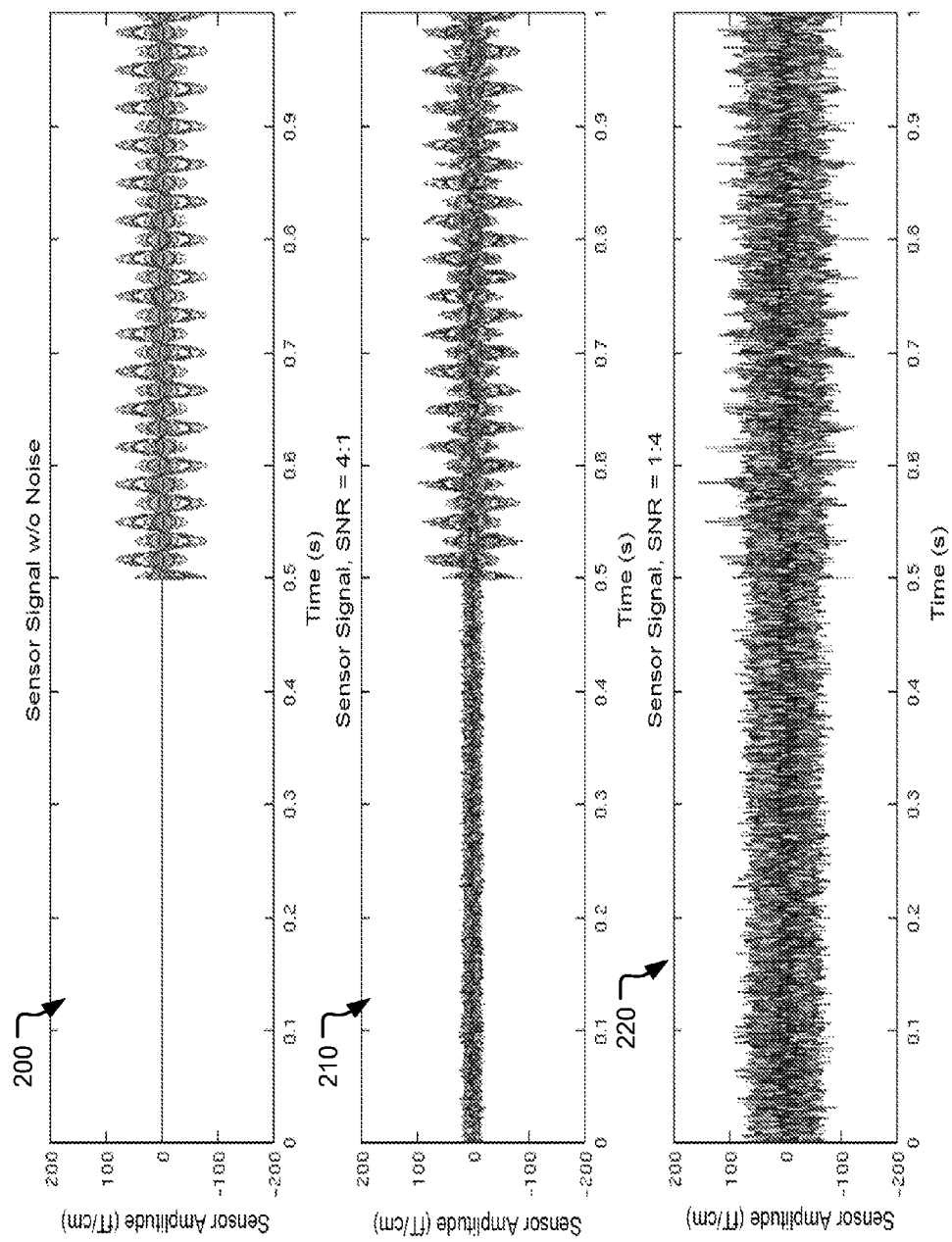
FIG. 2 shows Magnetoencephalography (MEG) sensor signals.

Simulations were used to test the performance of the MCBF. For two sources, the FIG. 2 below shows a variety of SNR conditions under which MCBF performs well. Please see attached manuscript for further details of computer simulations. FIG. 2 shows MEG sensor signals 200, 210 and 220. The top panel shows the sensor signal for a simulation with no noise 200. The center panel shows the same signal for a simulation with signal/noise ratio (SNR)=4:1 (210). The bottom panel shows the same signal for a simulation with SNR=1:4 (220). Accurate reconstructions were obtained even with the noise level depicted in the lower panel, SNR=1:4.

Simulations were also used to test the ability of the MCBF to recover source correlations. The table 1 below shows reconstructed correlations over a wide range of source correlations, and the error of the reconstruction. The simulations were carried out at SNR=2.0 with two sources and two cores.

| Dual-core Beamformer | | |
| --- | --- | --- |
| Actual 2-Source Correlation | Reconstructed Correlation | Error |
| 90.46% | 88.17% | 2.29% |
| 86.36% | 83.38% | 2.98% |
| 75.00% | 73.61% | 1.39% |
| 50.00% | 49.75% | 0.25% |
| 38.88% | 39.00% | 0.12% |
| 25.00% | 25.45% | 0.45% |
| 9.55% | 10.09% | 0.54% |
| 2.02% | 2.37% | 0.35% |

As is evident, the correlations are reconstructed with only minor error in the case of the two sources. The table 2 below lists pair-wise correlations and reconstructions for a simulation with three sources and three cores at SNR=3.0.

| Tri-core Beamformer | | | |
|---|---|---|---|
| Pair | Actual Correlation | Reconstructed Correlation | Error |
| 1-2 | 81.17% | 80.89% | 0.28% |
| 1-3 | 50.00% | 50.29% | 0.29% |
| 2-3 | 89.09% | 88.45% | 0.64% |

Figures 3A, 3B:
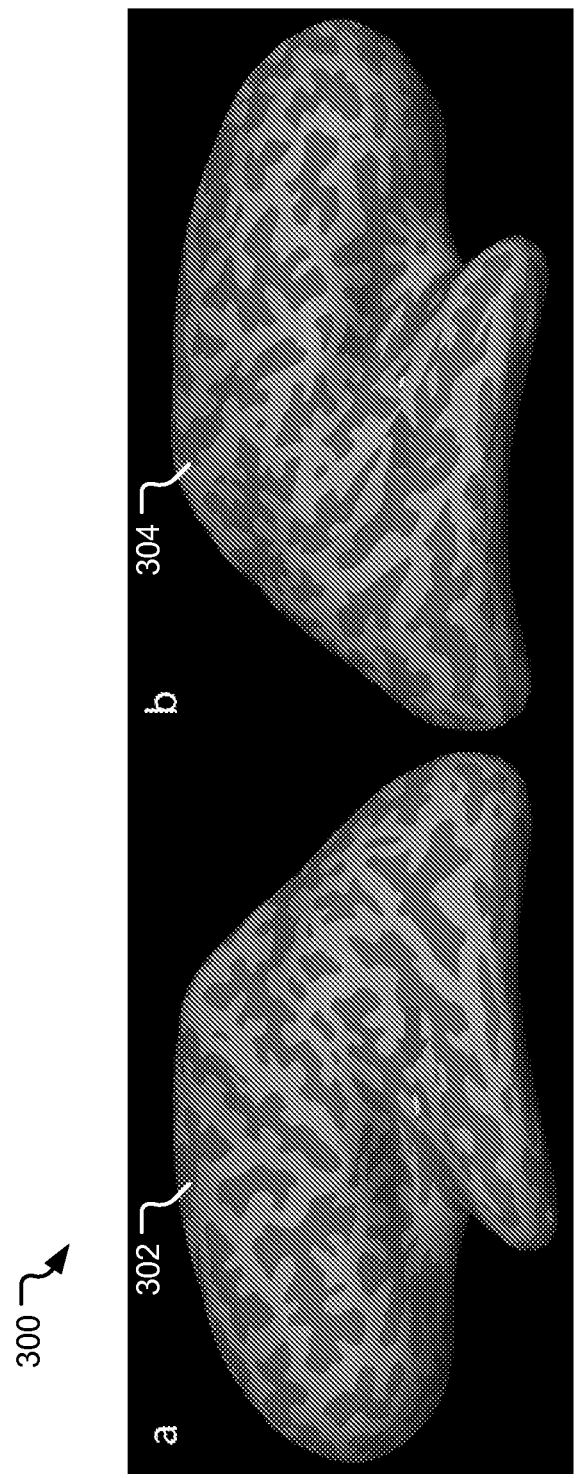
FIGS. 3A and 3B show Cortical activity map during stereo auditory stimulation.

As is evident, the errors in correlation reconstruction are all quite low. Thus, the MCBF also performs well with three sources and three cores. The FIGS. 3A and 3B show the two-core version of the MCBF used to reconstruct the human auditory response in magnetoencephalography readings. The experiment consisted of 200 epochs of evoked responses to a stereo test file. The test file consisted of an 1800 ms pre-stimulus noise measurement period and a 2000 ms post-stimulus period. The stimulus was a 500 Hz pure tone with a 40 Hz envelope modulated at 100% level, delivered to both ears simultaneously. FIGS. 3A and 3B show a cortical activity map 300 during stereo auditory stimulation: (a) Left hemisphere 302: The cortical activity map shows activation in the left primary auditory cortex; (b) Right hemisphere 304: The cortical activity map shows activation in the right primary auditory cortex. Red regions were thresholded at p<0.05 and yellow regions were thresholded at p<0.005.

Figure 4:
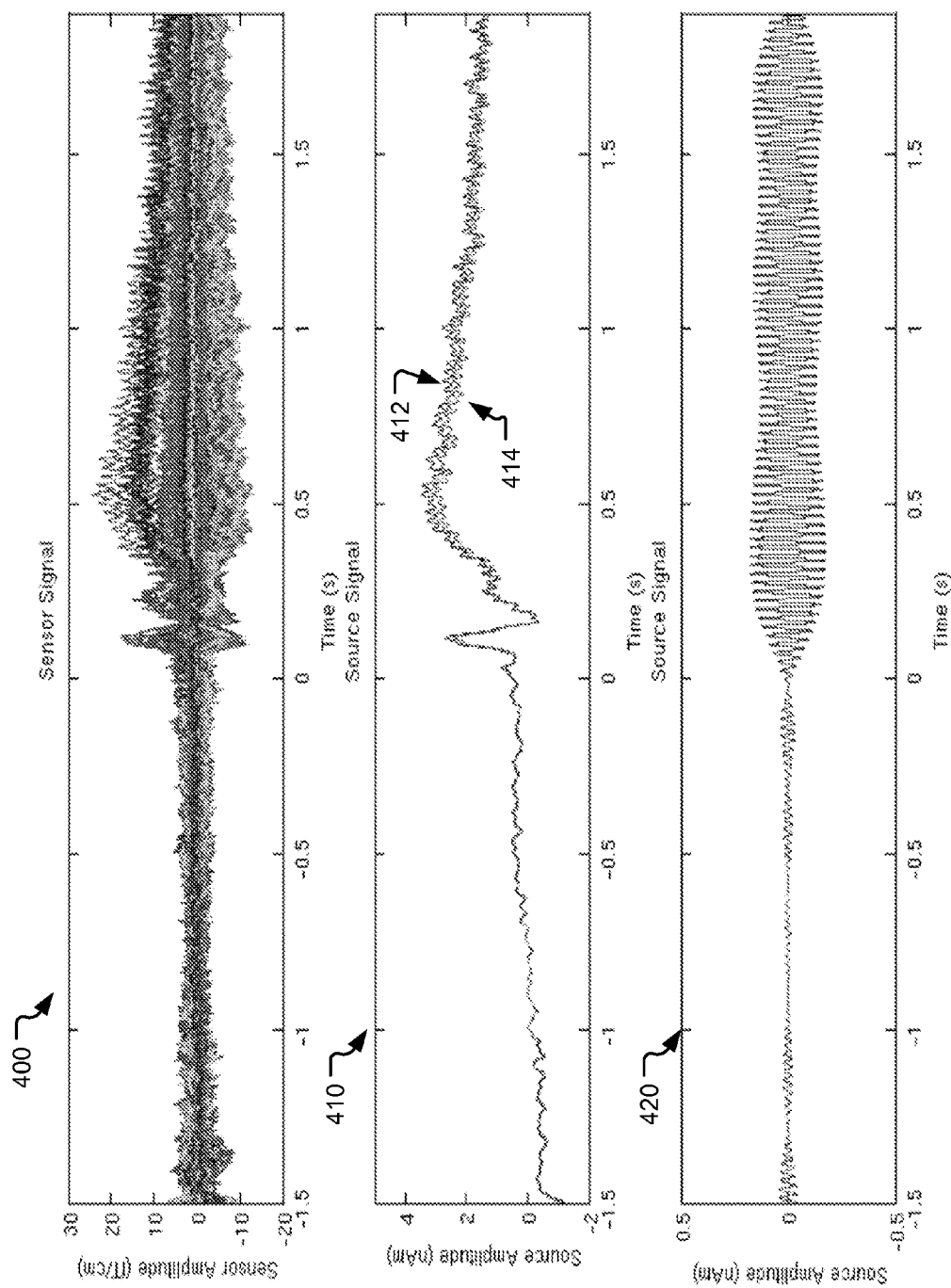
FIG. 4 shows stereo auditory-stimulation signal time-courses.

FIG. 4 shows the reconstructed time-courses from the two locations specified in FIG. 3. FIG. 4 shows stereo auditory-stimulation signal time-courses. The top panel shows the averaged sensor waveform for the auditory response 400. The center panel (410) shows the transient auditory response for both right hemisphere (blue:412) and left hemisphere (green:414). The bottom panel shows the 40 Hz steady-state auditory response for both hemispheres (420).

Figure 5:
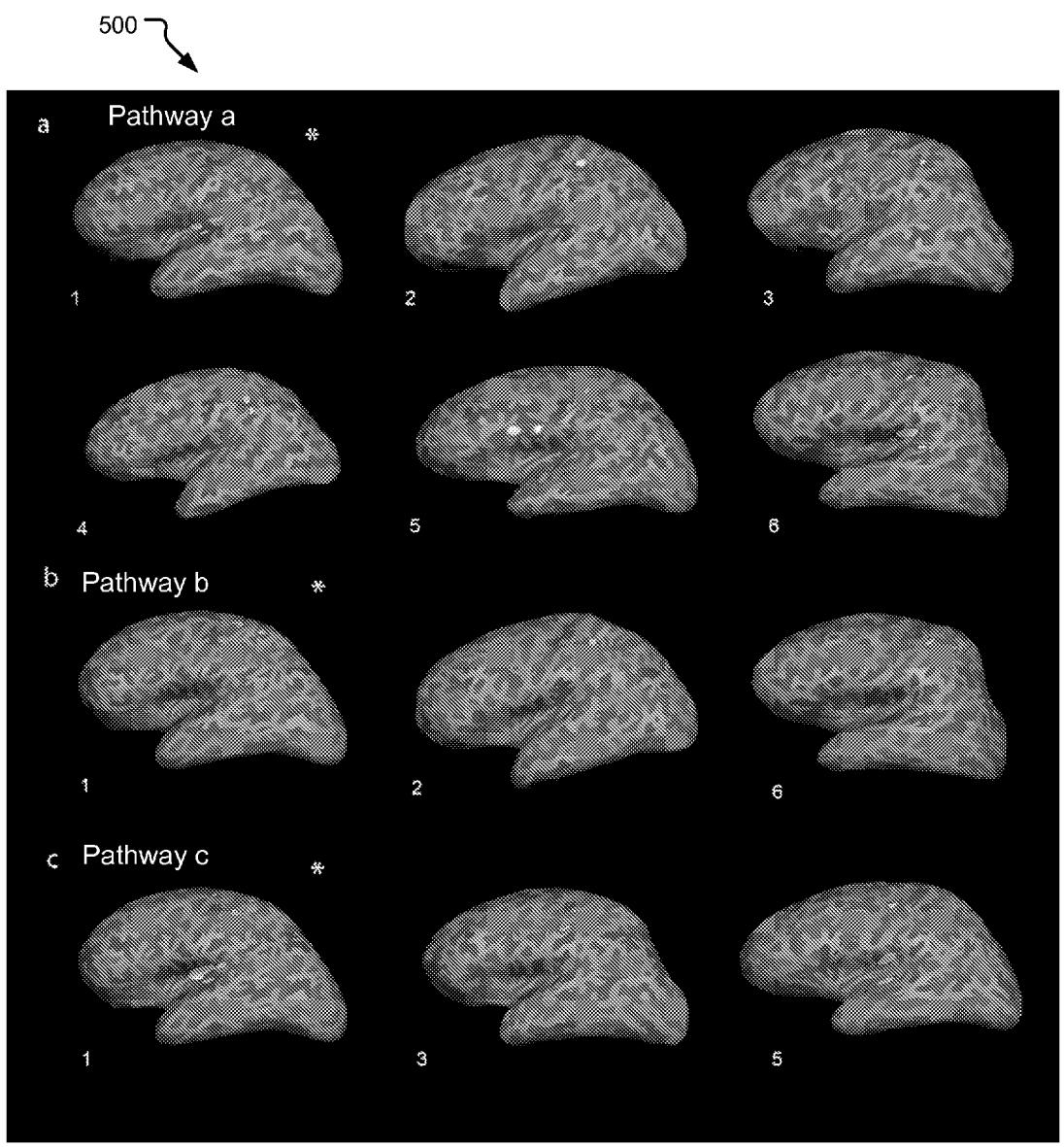
FIG. 5 shows right median-nerve stimulation activity maps for six human subjects.

FIG. 5 shows the dual-core version of the MCBF used to reconstruct the human median-nerve stimulation response in magnetoencephalography recordings (500). Each subject's median nerve was stimulated using a bipolar Grass™ constant-current stimulator. The stimuli were square-wave electric pulses of 0.2 ms duration delivered at a frequency of 1 Hz. The inter-stimulus-interval (ISI) was between 800 and 1200 ms. The intensity of the stimulation was adjusted until robust thumb twitches were observed. A trigger was designed to simultaneously send a signal to the MEG for every stimulus delivery to allow averaging over evoked trials. An interval of 500 ms post-stimulus was recorded, using 300 ms of prestimulus data for noise measurement. A minimum of 150 artifact-free MEG responses per subject were averaged with respect to the stimulus trigger. FIG. 5 shows right median-nerve stimulation activity maps 500 for six human subjects. Three common pathways were observed. Not all subjects showed activity in all pathways. Pathway 5a—Activity in primary somatosensory area (S1) and secondary somatosensory area (S2) (shown with red arrows) in all 6 subjects. Pathway 5b—Activity in S1 and somatosensory association cortex (Brodmann Area 5) in 3 subjects. Pathway 5c—Activity in S1 and/or S2 and the dorsal aspect of the primary motor area (M1) in 3 subjects. Red regions were thresholded at p<0.05 and yellow regions were thresholded at p<0.001.

Figure 6:
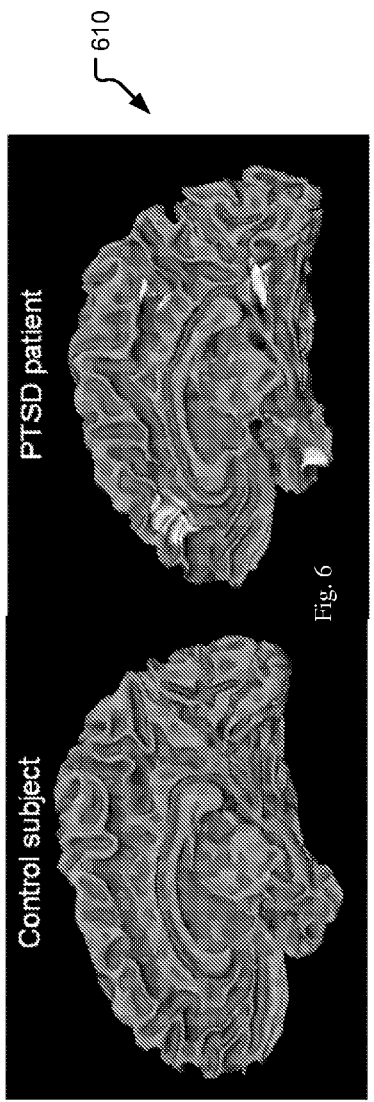
FIG. 6 shows the MCBF functional-connectivity map of the right hemisphere from resting-state MEG data. The left panel is from a representative healthy control and the right is from a PTSD patient. Hyperactivation is clearly visible in the amygdala/anterior-hippocampus, the posterior parahippocampal cortex, and the anterior and posterior cingulate cortices.

MCBF Data Showing the Abnormal Hyper-Activated Neuronal Network in One PTSD Patient FIG. 6 shows the MCBF functional-connectivity map of the right hemisphere from resting-state MEG data. The left panel 600 is from a representative healthy control and the right 610 is from a PTSD patient. Hyperactivation is clearly visible in the amygdala/anterior-hippocampus, the posterior parahippocampal cortex, and the anterior and posterior cingulate cortices.

Figure 7:
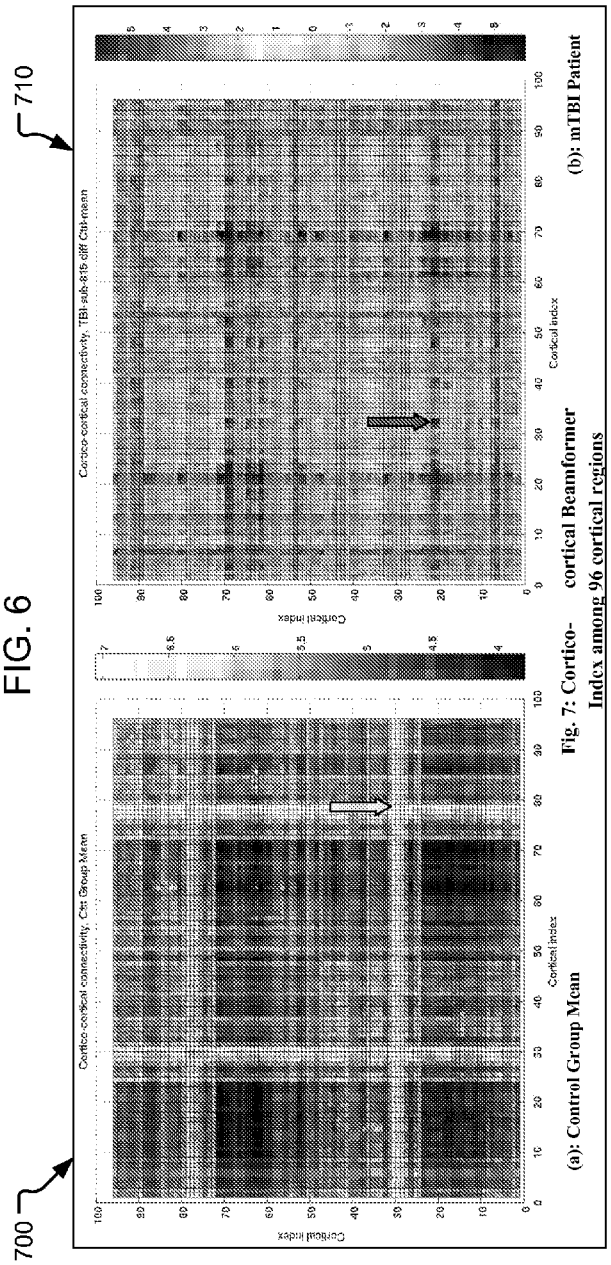
FIG. 7 shows Cortico-cortical Beamformer Index among 96 cortical regions.

MCBF Data Showing Abnormally Reduced Connectivity in Mild Traumatic Brain Injury (TBI) Patient FIG. 7 shows preliminary results of the regional-based dual-core beamformer: a connectivity map (RMS-value) among 96 cortical regions. The x- and y-labels are the indices of the 96 regions with 1-48 in left hemisphere and 49-96 in the right hemisphere; see www.cma.mgh.harvard.edu for their definitions. FIG. 7 (left panel) shows the regional connectivity in the gamma-band (30-100 Hz) from a MEG resting-state recording with eyes-closed (700). The map is the average over 12 healthy controls. The pseudo-Z-score is used to test gamma-band signal again the baselines of environmental and sensor noises. The green arrow shows that the correlated activity in region 30 (L posterior cingulate gyrus) and region 78 (R posterior cingulate gyrus) are substantially higher than the background noise. With such a preliminary "normative database", we examined if a TBI patient showed some abnormally (hyper- or hypo-) activated networks. In Fig. (right panel), we plot the difference of the connectivity map between an mTBI patient and the group-mean of the healthy control group, normalized by the standard deviation (SD) of the healthy control group (710). The color bar in this plot is in units of standard deviations, with negative values showing lower connectivity in this mTBI patient as compared to the normative mean in healthy controls. Many regions in the mTBI patients show abnormally reduced connectivity (beyond 3 SD). For example, the red arrow shows that the connectivity between region 21 (L angular gyrus) and region 32 (L cuneal cortex) is markedly reduced by ~5 SD.

Setup for Computer Simulations

Computer simulations were performed in order to examine the performance of both the dual-core spatial filter and the non-linear modified Powell search portions of the DCBF. The simulator was programmed to test up to three pairs of source dipoles under differing conditions of frequency, cross-correlation, and amplitude. The base signal for each dipole was programmed to be a simple sinusoidal wave in a specific direction. In addition, the noise simulation was programmed so that the SNR of each simulation could be chosen manually by adding uncorrelated random noise. The searchable source space was simulated with a fixed-source grid based on the gray-matter boundary obtained from a healthy subject's T1-weighted MRI using Freesurfer and a grid spacing of 7 mm. The boundary element method (BEM) was used for the MEG forward model calculation with the BEM mesh (5 mm mesh size) being the inner-skull surface from the MRI. In each case, SVD was used to reduce the lead-field vectors to m×2 matrices. In each simulation, the search was given 1000 random re-starts. Performance was evaluated by average time to find the correct solution or equivalently, the number of searches required on average to find the solution.

To evaluate the performance of our reconstruction under differing levels of noise, simulations were performed with the following control conditions: 1 pair of sources, 30 Hz frequency, 100% intra-pair correlation, and 1:1 amplitude ratio for the two source dipoles. Reconstruction was evaluated at SNRs of 4.0, 3.0, 2.0, 1.0, 0.50, 0.33, and 0.25. In our simulations, we defined SNR in sensor domain as the total power of the signal divided by the total power of the noise that was added to the signal. To examine the effects of source signals containing more than one frequency component, the 0.25 SNR test condition was repeated for 1 pair of 100% correlated sources with a dominant 30 Hz component and a half-amplitude 20 Hz component. The 0.25 SNR test condition was also repeated to test DCBF performance in the presence of correlated noise at 10 Hz. Correlated noise was introduced by means of a single noise source of same amplitude oscillating at a frequency of 10 Hz throughout the entire simulation.

To evaluate the performance of our reconstruction under differing correlations within the source pair, simulations were performed with the control conditions: 1 pair of sources, 30 Hz frequency, 1:1 source amplitude ratio, and SNR of 2.0. The following intra-pair correlations were simulated as the variable condition: 86.6%, 75%, and 50%. To evaluate the performance of our reconstruction under differing source amplitudes, simulations were performed with the control conditions: 1 pair of sources, 30 Hz frequency, 100% intra-pair correlation, and SNR of 2.0. The following amplitude ratios were simulated as the variable condition: 1:1, 2:1, and 3:1. To evaluate the performance of our reconstruction in a more realistic scenario and for multiple dipoles, three source-pairs were selected with frequencies of 20 Hz, 30 Hz, and 40 Hz. Each source dipole had differing amplitudes. Each pair of dipoles was programmed with slightly different intra-pair correlations. The dipoles were also uncorrelated across pairs. The SNR was set to 0.6075.

To evaluate the performance of our reconstruction in the presence of three correlated sources, three sources were given a sinusoidal signal with a frequency of 30 Hz at a SNR of 0.25. The second and third sources were phase-shifted 22.5 degrees and 45 degrees from the first source. Activation maps were generated for the pathway with highest pseudo-Z-score from the formula:

$$Z_{comb} = \frac{\max(z_1)[z_1 - \min(z_1)]}{\max(z_1) - \min(z_1)} + \frac{\max(z_2)[z_2 - \min(z_2)]}{\max(z_2) - \min(z_2)} \quad (21)$$

$Z_1$ contains the pair-wise pseudo-Z-scores for the first optimal dipole with all other dipole sources. $Z_2$ contains the pair-wise pseudo-Z-scores for the second optimal dipole with all other dipole sources. Monte Carlo simulations were used to obtain a distribution of pseudo-Z-scores produced by noise. A kernel-smoothed density-estimate was computed to produce a continuous distribution. Statistical significance of pseudo-Z-scores for all activation maps was determined by integration of the continuous distribution.

Setup for Auditory Steady-State MEG Response

An auditory stimulus experiment was designed to test DCBF reconstruction of correlated sources in an actual MEG measurement. The experiment consisted of 200 epochs of evoked responses to a stereo test file. The test file consisted of an 1800 ms pre-stimulus noise measurement period and a 2000 ms post-stimulus period. The stimulus was a 500 Hz pure tone with a 40 Hz envelope modulated at 100% level. The intensity of the stimulus was balanced between left and right ears. The start and end of the stimulus were smoothed with a cosine roll-off to prevent any artifacts from the stimulus. Magnetic fields evoked by auditory stimulation were measured using an Elekta/Neuromag™ whole-head MEG system (VectorView) with 204 gradiometers and 102 magnetometers in a magnetically shielded room (IMEDCO-AG, Switzerland). EOG electrodes were used to detect eye blinks and eye movements. An interval of 1900 ms post-stimulus data was recorded, using 1500 ms of pre-stimulus data for noise measurement. Data were sampled at 1000 Hz and run through MaxFilter to remove environment noise. 188 artifact-free MEG responses were averaged with respect to the stimulus trigger. A BEM mesh of 5-mm mesh size for the subject was generated from the inner-skull surface using a set of T1 MRI images taken on a 1.5 T GE scanner. A fixed source grid with 7-mm spacing was generated from the gray-white matter boundary of the T1 image by Freesurfer. Lead-field vectors for each dipole source were reduced to m×2 matrices by ignoring the weakest orientation, reducing all reconstructed time-courses to two components. Registration of MRI and MEG was performed using data obtained from the Isotrack system prior to subject scanning in the MEG machine. The signal was then reconstructed using the dual-core beamformer approach coupled to the non-linear modified Powell search. Activation maps were generated in the same fashion as in (Eqn. 21). Source time-courses were low-pass filtered under 50 Hz to display the auditory response. Time-frequency (TF) analysis of the source time-courses with Morelet wavelets (5 Hz width) was performed between 1 and 50 Hz to identify transient and steady-state auditory responses.

Setup for Right Median Nerve Stimulation MEG Response

The performance of the DCBF was further examined using human MEG responses to right median nerve stimulation. This task is widely used to study the somatosensory system and provides a useful standard for analyzing DCBF performance since the location of activated dipole sources is easily predictable. We conducted MEG recordings for this experiment on 6 healthy subjects (men, ages 20-42) as they underwent right median-nerve stimulation. All subjects signed the consent forms approved by the Institutional Review Board of the University of California at San Diego. Each subject's median nerve was stimulated using a bipolar Grass™ constant-current stimulator. The stimuli were square-wave electric pulses of 0.2 ms duration delivered at a frequency of 1 Hz. The inter-stimulus-interval (ISI) was between 800 and 1200 ms. The intensity of the stimulation was adjusted until robust thumb twitches were observed. A trigger was designed to simultaneously send a signal to the MEG for every stimulus delivery to allow averaging over evoked trials. Magnetic fields evoked by median nerve stimulation were measured using the Elekta/Neuromag™ whole-head MEG system. EOG electrodes were used to detect eye blinks and eye movements. An interval of 500 ms post-stimulus was recorded, using 300 ms of pre-stimulus data for noise measurement. Data were sampled at 1000 Hz and run through a high-pass filter with a 0.1 Hz cut-off and through MaxFilter to remove environmental noise. A minimum of 150 artifact-free MEG responses per subject were averaged with respect to the stimulus trigger. BEM mesh generation, source grid generation, MRI-MEG registration, and source time-course reconstruction were carried out in the same manner as in the auditory steady-state MEG response experiment. Activation maps were generated in the same fashion as in (Eqn. 21).

Computer Simulations: Computational Time for Obtaining the Optimal Dipole Orientations and Weights To examine the difference in computational costs between the non-linear search approach from Brookes and colleagues and our analytical approach, we performed 100 Nelder-Mead non-linear simplex searches and 100 eigenvalue decompositions to obtain the optimal dipole orientations and optimal dipole weighting for two simulated dipoles. Non-linear searching and eigenvalue decomposition both resulted in accurate reconstruction of orientations and weighting with less than 1% difference. The average times for reconstruction were 0.0142 s and $1.4 \times 10^{-4}$ s for the simplex search and the eigenvalue decomposition, respectively, resulting in a speed up of 100 times using our approach. Performing the exhausted analysis for all combinations of two-dipole pairs in a 5000 dipole-grid would take approximately 50 hours using the non-linear search approach from Brookes and colleagues. In contrast, our direct computation approach based on eigenvalue decomposition would take approximately 30 minutes. As we show later in this section, the modified Powell approach further speeds up the analysis by bypassing the exhaustive analysis of all dipole combinations.

SNR

The results from the simulations designed to test performance under varying SNR are listed in Table 3.

TABLE 3

DCBF Performance under varying SNR

| SNR | Amplitude (nAm) | | | | Reconstructed Amplitude (nAm) | | | | Orientation Ratio | | Reconstructed Orientation Ratio | | Average # Searches | Average Time (min) | Pseudo-Z-score |
|---|---|---|---|---|---|---|---|---|---|---|---|---|---|---|---|
| | Dipole 1 | | Dipole 2 | | Dipole 1 | | Dipole 2 | | Dipole 1 | Dipole 2 | Dipole 1 | Dipole 2 | | | |
| 4.0 | 10 | 20 | 10 | 20 | 9.4 | 18.7 | 9.2 | 18.5 | 0.5 | 0.5 | 0.501 | 0.498 | 31.3 | 1.502 | 11.3 |
| 3.0 | 10 | 20 | 10 | 20 | 9.4 | 18.7 | 9.2 | 18.5 | 0.5 | 0.5 | 0.501 | 0.498 | 28.6 | 1.411 | 11.2 |
| 2.0 | 10 | 20 | 10 | 20 | 9.4 | 18.8 | 9.2 | 18.4 | 0.5 | 0.5 | 0.502 | 0.497 | 21.7 | 1.015 | 11.1 |
| 1.0 | 10 | 20 | 10 | 20 | 9.5 | 18.9 | 9.1 | 18.3 | 0.5 | 0.5 | 0.503 | 0.495 | 14.3 | 0.716 | 10.9 |
| 0.50 | 10 | 20 | 10 | 20 | 9.7 | 19.3 | 8.9 | 18.1 | 0.5 | 0.5 | 0.505 | 0.491 | 5.4 | 0.257 | 10.3 |
| 0.33 | 10 | 20 | 10 | 20 | 9.9 | 19.5 | 8.7 | 17.8 | 0.5 | 0.5 | 0.507 | 0.487 | 2.3 | 0.102 | 9.9 |
| 0.25 | 10 | 20 | 10 | 20 | 10.1 | 19.8 | 8.5 | 17.6 | 0.5 | 0.5 | 0.509 | 0.483 | 1.4 | 0.059 | 9.4 |

In each test, the dipole-pair locations reconstructed with the highest pseudo-Z-score were identical to the dipole-pair locations that were originally programmed with the signal. Thus, even under an SNR of 0.25, the reconstruction was able to localize the sources perfectly. Under all levels of SNR, the orientations were recovered faithfully ($0.27\% < \epsilon < 2.56\%$). Orientation error, $\epsilon$, was defined as the mean of the fractional errors of the individual dipole orientation ratios. Source amplitudes were reconstructed accurately across all levels of SNR ($6.8\% < \epsilon < 7.2\%$). Reconstructed amplitudes were determined by finding the intensity of the Fourier transform for the reconstructed time-course at the appropriate frequency. When source dipoles contained signals of two frequencies, the accuracy of reconstructing each frequency component's amplitude was similar to the single frequency scenario ($\epsilon_{30}=7.24\%$, $\epsilon_{20}=7.70\%$). In the presence of correlated noise, source dipole locations were reconstructed accurately and quickly, though the amplitude error ($\epsilon=8.5\%$) and orientation error ($\epsilon=4.29\%$) were slightly higher. Interestingly, the average number of searches and the average time taken to find the optimum dipole pair are reduced linearly as the SNR decreases, but saturate as the SNR approaches zero ($r_{search}^2=0.9608$; $r_{time}^2=0.9599$).

Signal Correlation

The results from the simulations designed to test performance under varying signal correlations are displayed in Table 4.

TABLE 4

DCBF Performance under varying source correlation

| Correl. | Amplitude (nAm) | | | | Reconstructed Amplitude (nAm) | | | | Orientation Ratio | | Reconstructed Orientation Ratio | | Average # Searches | Average Time (min) | Pseudo-Z-score |
|---|---|---|---|---|---|---|---|---|---|---|---|---|---|---|---|
| | Dipole 1 | | Dipole 2 | | Dipole 1 | | Dipole 2 | | Dipole 1 | Dipole 2 | Dipole 1 | Dipole 2 | | | |
| 100% | 10 | 20 | 10 | 20 | 9.4 | 18.8 | 9.2 | 18.4 | 0.5 | 0.5 | 0.502 | 0.498 | 21.7 | 1.015 | 11.1 |
| 86.6% | 10 | 20 | 10 | 20 | 9.1 | 18.2 | 8.8 | 17.8 | 0.5 | 0.5 | 0.501 | 0.497 | 1 | 0.034 | 11.3 |
| 75.0% | 10 | 20 | 10 | 20 | 8.9 | 17.7 | 8.5 | 17.1 | 0.5 | 0.5 | 0.501 | 0.497 | 1 | 0.033 | 11.0 |
| 50.0% | 10 | 20 | 10 | 20 | 8.3 | 16.5 | 7.8 | 15.7 | 0.5 | 0.5 | 0.501 | 0.497 | 1 | 0.035 | 10.5 |

In each case, the dipole pair reconstructed was identical to the original source dipoles. Thus, even under a correlation of only 50%, the reconstruction was able to localize the sources perfectly. The reconstructed amplitudes in each of these simulations faithfully matched the original source amplitudes ($\bar{\epsilon}$=12.5%; $\sigma_{\bar{\epsilon}}$=5.1%) and became linearly more accurate as the pair correlation increased ($r^2$=0.99905). The reconstructed orientations also faithfully matched the original source orientations and exhibited little dependence on the correlation ($\bar{\epsilon}$=0.40% $\sigma_{\bar{\epsilon}}$=0.18%). Interestingly, the proper dipole pair was found more immediately, repeatedly, and quickly for non-perfectly correlated than perfectly-correlated sources. For each non-perfectly correlated simulation, decreasing the original source correlation led to a concomitant linear decrease in the pseudo-Z-score ($r^2$=0.99998).

Source Amplitude Ratio

The results from the simulations designed to test performance under varying amplitude ratios within a pair of dipoles are shown in Table 5.

TABLE 5

DCBF Performance under varying source amplitude ratio

| Amplitude Ratio | Reconstructed Amplitude Ratio | Orientation Ratio | | Reconstructed Orientation Ratio | | Average # Searches | Average Time (min) | Pseudo-Z-score |
|---|---|---|---|---|---|---|---|---|
| | | Dipole 1 | Dipole 2 | Dipole 1 | Dipole 2 | | | |
| 1:1 | 0.98 | 0.5 | 0.5 | 0.502 | 0.497 | 21.7 | 1.015 | 11.1 |
| 2:1 | 1.93 | 0.5 | 0.5 | 0.505 | 0.497 | 6.1 | 0.274 | 11.2 |
| 3:1 | 2.87 | 0.5 | 0.5 | 0.508 | 0.498 | 1.5 | 0.065 | 11.2 |

The reconstructed amplitude ratios in each simulation closely reflect the original source amplitude ratio (1.97%<$\epsilon$<4.48%). In the reconstruction, the orientations faithfully represent the original source orientations (0.34%<$\epsilon$<1.63%). As one increases the relative amplitude ratios within each pair of dipoles from 1 to 2 to 3, the number of searches and the time required to find the dipole pair decrease linearly ($r_{search}^2$=0.908; $r_{time}^2$=0.905). The amplitude ratio did not affect the computed pseudo-Z-scores.

Three Pairs of Dipoles

The results for the six dipole (3 source-pair) simulation are presented in Table 6.

TABLE 6

DCBF Performance with three source pairs

| Source Index | Correl. | Freq. (Hz) | Amp. (nAm) | | Reconst. Amplitude (nAm) | | Orient. Ratio | Reconst. Orientation Ratio | Average # Searches | Average Time (min) | Pseudo-Z-score |
|---|---|---|---|---|---|---|---|---|---|---|---|
| | | | Dir. 1 | Dir. 2 | Dir. 1 | Dir. 2 | | | | | |
| 1 | 92.39% | 20 | 10 | 20 | 8.26 | 16.27 | 0.500 | 0.508 | 6.37 | 0.21 | 7.57 |
| 2 | 92.39% | 20 | 15 | 25 | 13.88 | 23.97 | 0.600 | 0.579 | 6.37 | 0.21 | 7.57 |
| 3 | 95.11% | 30 | 30 | 20 | 28.30 | 18.98 | 1.500 | 1.492 | 1.20 | 0.04 | 8.97 |
| 4 | 95.11% | 30 | 12 | 8 | 9.77 | 6.90 | 1.500 | 1.415 | 1.20 | 0.04 | 8.97 |
| 5 | 96.59% | 40 | 20 | 15 | 17.90 | 14.26 | 1.333 | 1.255 | 142.86 | 4.80 | 7.09 |
| 6 | 96.59% | 40 | 10 | 12 | 8.59 | 10.12 | 0.833 | 0.849 | 142.86 | 4.80 | 7.09 |

All six sources were reconstructed in an average of 4.8 minutes and 143 searches. Increasing the number of correlated pathways in the simulation did not result in an unmanageable increase in computational time. Even with the low SNR (0.6075), differing intra-pair correlations, and differing amplitudes both inside and outside of each dipole pair, all of the dipoles were reconstructed to the proper spatial position. The three inter-pair correlations in this study were all zero. Furthermore, the twelve reconstructed amplitudes closely represented the original source amplitudes ($\bar{\epsilon}$=11.32% $\sigma_{\bar{\epsilon}}$=5.67%). Reconstruction of each source's orientation was reasonably accurate ($\bar{\epsilon}$=3.16% $\sigma_{\bar{\epsilon}}$=2.22%).

A Third Correlated Source

Figure 8:
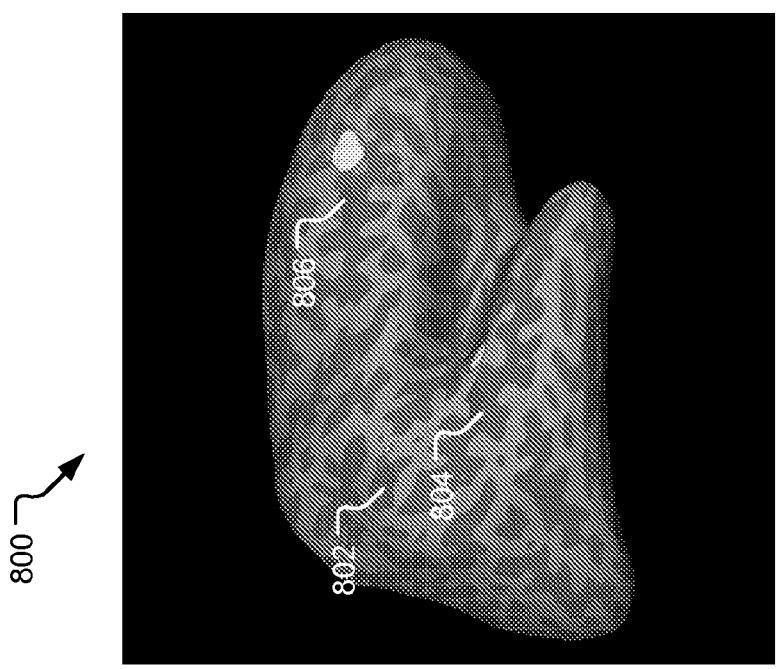
FIG. 8 shows an Activation Map for Three Correlated Sources. The red arrows on the activity map indicate the position of the three source dipoles. The map was thresholded such that red indicates P<0.05 and yellow indicates $P<10^{-5}$.

Two of the three sources in the simulation were reconstructed accurately in an average of 1.03 searches and 0.04 minutes. As expected, the amplitudes of the reconstructed sources were suppressed by 47.29% due to the third correlated source. FIG. 8 shows an activation map 800 of the three reconstructed sources, which was derived by combining the dipole pseudo-Z-scores. The red arrows 802, 804 and 806 on the activity map indicate the position of the three source dipoles. Red values were thresholded at P<0.05, and yellow values were thresholded at P<$10^{-5}$. The combined pseudo-Z-score for all three dipoles was significant (P<$10^{-5}$).

Applying DCBF to Human Auditory MEG Responses

Figure 9:
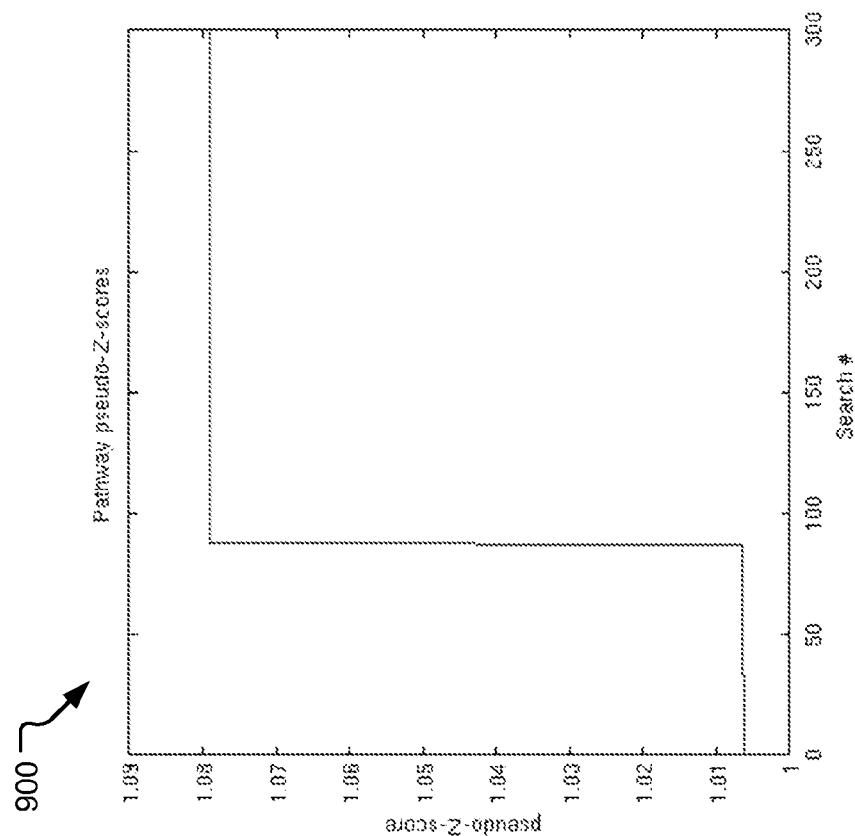
FIG. 9 shows an exemplary stereo auditory stimulation in a human subject: activated pathways with associated pseudo-Z-scores. Plateaus in the plot denote searches that yield the same result (local maximum) multiple times. Results that are found multiple times are termed pathways. The pathway with maximum correlation (pseudo-Z-score) and maximum size involved both primary auditory cortices and is depicted in FIG. 11. Only 300 out of 1000 searches are shown to emphasize the transition between pathways.
Figure 10:
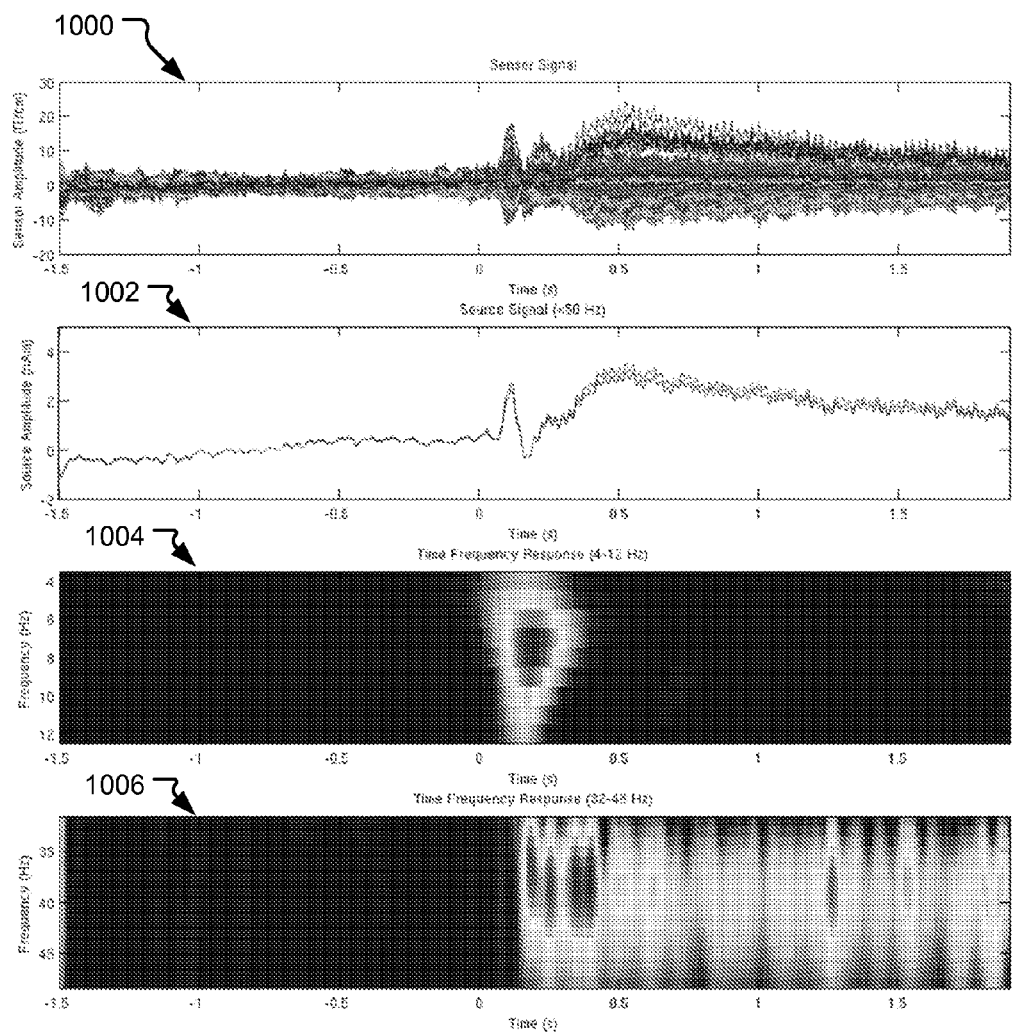
FIG. 10 shows exemplary Stereo auditory-stimulation signal time-courses. The top panel shows the averaged sensor waveform for the auditory response. The second panel shows the auditory response for both right hemisphere (blue) and left hemisphere (green). The third panel shows the transient auditory-response between 4 and 12 Hz with time-frequency analysis. The fourth panel shows the steady-state auditory centered at 40 Hz with time-frequency analysis.

MEG data were obtained for the 500 Hz tone auditory stimulus tests (Brookes et al., 2007). All data were subsequently processed with MaxFilter and the signal was reconstructed utilizing our new DCBF approach coupled with the modified Powell search restricted to inter-hemispheric searches. To enhance the SNR of the relatively weak auditory response, 188 responses were averaged. FIG. 9 displays the pseudo-Z-scores 900 of the pathways or local maxima found by the modified Powell search algorithm. After 1000 starts, the optimum pathway had a Z-score of 1.0791 (p<1.3·$10^{-5}$), indicating that two highly correlated dipoles had been found. Out of the 3 identified pathways, this pathway was also found most often, taking an average of 1.1 searches or 0.0305 minutes. Referring back to FIGS. 3A and 3B, displayed is the cortical activity map 300 derived from plotting the combined correlations of each optimal dipole with all other dipoles in the brain: a) Left hemisphere 302: The cortical activity map shows activation in the left primary auditory cortex; and b) Right hemisphere 304: The cortical activity map shows activation in the right primary auditory cortex. For both hemispheres, red values were thresholded at P<0.05, and yellow values were thresholded at P<0.005. FIGS. 3A and 3B show that the activity is localized to Brodmann Areas 41 and 42 (primary and association auditory cortices) in both left and right hemispheres. Weaker pathways localized to deep sources. FIG. 10 displays exemplary stereo auditory-stimulation signal time-courses, the time-courses 1000, 1002, 1004 and 1006 of the transient and steady-state auditory responses. The left to right hemisphere source amplitude ratio was 1.11. Wavelet transform time-frequency (TF) analysis was performed on the reconstructed signal to identify the transient and steady-state responses. TF analysis between 4 and 12 Hz showed a focal region of power immediately following stimulus delivery, corresponding to the auditory transient response. TF analysis of the source signal in the 32-48 Hz band indicated the presence of power throughout the entire stimulus period centered at 40 Hz, corresponding to the auditory steady-state response.

Applying DCBF to Human Median Nerve Stimulation MEG Responses

Figure 11:
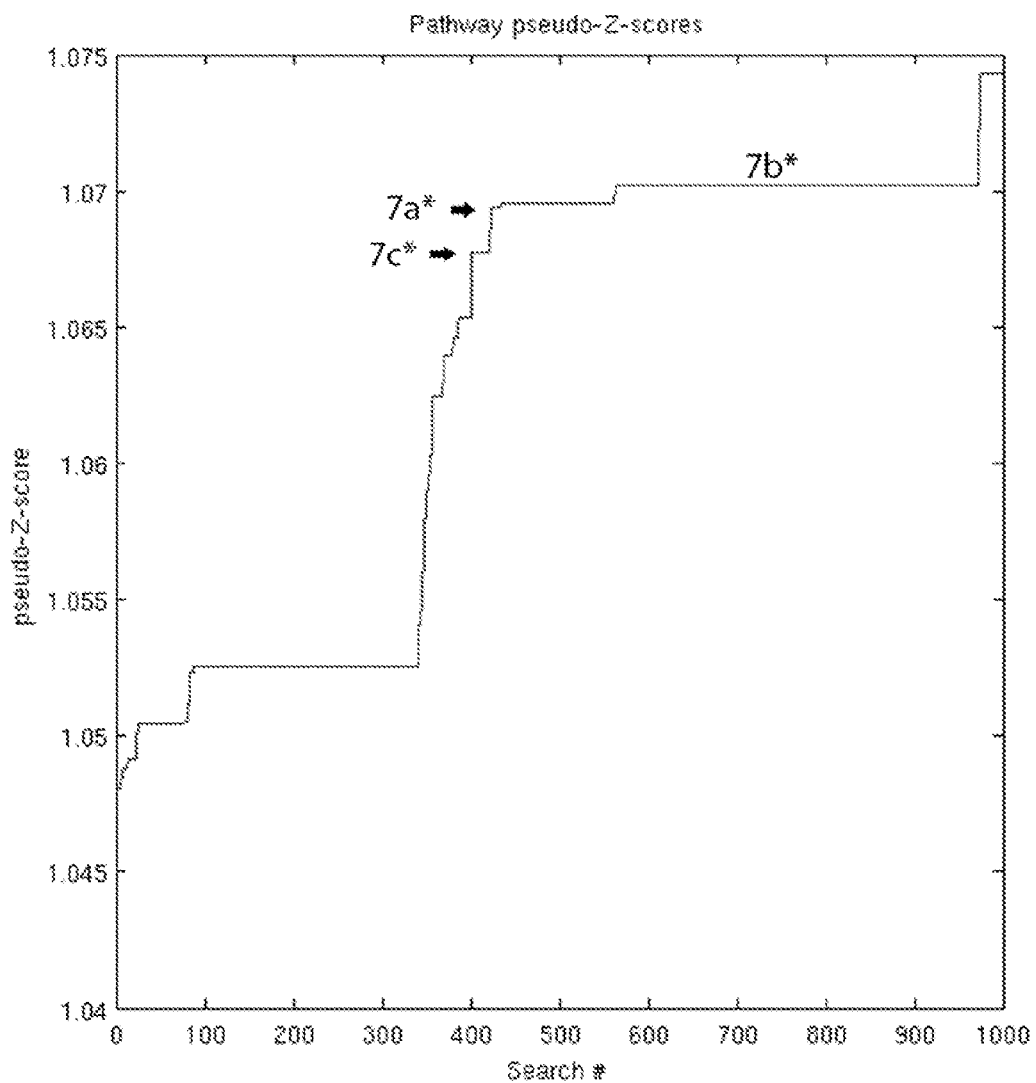
FIG. 11 shows an exemplary right median-nerve stimulation in a single human subject: activated pathways with associated pseudo-Z-scores. Plateaus in the plot above denote searches that yield the same result (local maximum) multiple times. Results that are found multiple times are termed pathways.

MEG data were obtained from six healthy subjects for the right median nerve stimulus test. Individual trials were averaged to enhance the SNR of the MEG evoked-response. All data were subsequently processed with MaxFilter), and spatial locations were reconstructed utilizing the DCBF approach. FIG. 11 shows an exemplary right median-nerve stimulation 1100 in a single human subject: activated pathways with associated pseudo-Z-scores. FIG. 11 shows the multiple pathways found by DCBF sorted according to pseudo-Z-score or correlation for a single representative subject.

The plateaus or clusters in FIG. 11 designate searches that yielded the same result multiple times, referred to as pathways or networks of activation. Referring back to FIG. 5, shown are activity maps 500 computed with (Eqn. 21) for three of these selected networks along with similar networks reconstructed from other subjects. The activity maps 500 were computed in the same manner as for the auditory-response analysis. All subjects had a common network of activation in the primary somatosensory cortex (S1, including Brodmann Areas 1, 2, and 3) and the secondary somatosensory cortex (S2) (Pathway a). Three subjects showed common networks involving the primary somatosensory cortex (S1) and Brodmann Area 5 of the posterior parietal lobe (Pathway b). Three subjects also had a common network of activation involving the primary motor cortex (M1) and parts of the somatosensory cortex (S1 or S2) (Pathway c). Two subjects showed a previously observed network of activation involving the primary somatosensory cortex (S1) and the temporal-parietal junction, a poly-sensory area.

Applications

Only a few embodiments have been described of a novel and powerful dual-beamformer method paired with the modified-Powell search to create the DCBF. Our DCBF approach addressed various shortcomings of the earlier dual-beamformer method, the CCSM, and the NB. Instead of using a spatial filter or lead-field vector consisting of a linear combination of lead-field vectors from two dipoles, we chose to concatenate the lead-field vectors from the two dipoles together, which simultaneously covered two spatial locations at once. We were also able to perform eigenvalue decomposition and analysis of the low-dimensional K matrix to analytically find the optimal pseudo-Z-score of two dipoles directly, without having to search for their best orientations non-linearly. In addition, we performed eigenvalue decomposition of another low-dimensional Q matrix to analytically recover the most favorable weighting between dipoles and the best orientation of the dipoles that optimized the pseudo-Z-score (Sekihara et al., 2004) without the need for a time-consuming non-linear search process that takes approximately 100 times longer. Optimal source dipoles were found by our modified non-linear Powell search instead of through exhaustive brute-force search, which is about three times slower. The Powell search also enabled analysis without a priori information about any of the dipole positions. Thus, we were able to identify multiple highly-correlated neuronal networks that were associated with meaningful local maxima of pseudo-Z-scores.

We conducted a series of computer simulations to test the robustness and performance of the DCBF with regards to variations in several important parameters. We showed that decreased SNR leads to faster localization of the source dipoles during the modified Powell search. A Powell search has the best probability of finding peaks with broad bases. Thus, we believe that lower SNR leads to a broader peak in pseudo-Z-score, which allows the optimal dipole combination to be identified more readily. In fact, the reconstruction performed reliably even under conditions of 0.25 SNR for both single and dual frequency sources and for both uncorrelated and correlated band-limited noise. At every SNR tested, our reconstruction technique successfully located the source dipoles without error. For spontaneous recordings, the MEG signal can often have a very low SNR, especially since the data cannot be averaged. For evoked recordings, a higher SNR can be obtained from averaging. Our computer simulations show that the DCBF may be applied for both types of recordings, since the method operates over a wide range of SNR.

By varying source correlation, we found that the DCBF successfully identified sources even when their signals were only 50% correlated. In fact, non-purely correlated sources were localized much more quickly than 100% correlated sources because the pseudo-Z-score solution space is less sharply peaked around the global maximum for non-purely correlated sources than for fully correlated sources.

To test the performance of our direct computation of optimal dipole weighting, we performed computer simulations with source dipoles emitting signals at varying ratios of amplitudes. Interestingly, as we increased the disparity in amplitude between signals, the reconstruction was able to localize the source dipoles more quickly. Differing source amplitudes likely led to a broader peak in pseudo-Z-score, allowing the optimal dipole combination to be identified more readily. The primary purpose of the amplitude simulations, however, was to examine if the reconstructed signals still maintained the proper amplitude weighting. Reconstructed amplitude ratios were indeed quite close to the original source amplitude ratios, confirming that our approach to obtaining optimal weighting was successful.

To determine whether the DCBF could perform in real-world conditions, we designed one simulation with three pairs of non-purely correlated dipoles. All three pairs of correlated sources were localized accurately within an average of 5 minutes. Furthermore, the amplitude ratios and orientations were reconstructed with only minor error, demonstrating that the DCBF can accurately reconstruct multiple simultaneously-activated networks of correlation.

Another simulation was designed at low SNR to test the ability of the DCBF to reconstruct three correlated dipoles. Only two sources could be located with the Powell search, and their amplitudes were suppressed. The suppression occurred due to the underlying assumption that only two sources are correlated. Thus, the effect was similar to suppression of the conventional single beamformer in the presence of a second correlated source. However, the generated activity map shows that the DCBF successfully localized all three correlated-source in a significant manner (FIG. 8).

By applying our novel method to the analysis of bilateral auditory-stimulation data in humans, we showed that the DCBF could quickly (<20 sec) and accurately reconstruct correlated sources in a real experiment. The localized sources corresponded to the primary auditory cortices, as expected. In addition, the reconstructed signal showed both the expected 40 Hz steady-state response and the transient response. The optimal dipoles also corresponded to the auditory network, which was the network most frequently found with the highest pseudo-Z-score.

To explore the idea of finding multiple networks, we also applied the DCBF approach in an analysis of right median-nerve stimulation data from six healthy subjects. A plot of the number of searches as a function of pseudo-Z-scores showed that searches that yielded the same results multiple times corresponded to different pathways of correlated sources. We found that the most common pathway among subjects corresponded to activation in the primary somatosensory area (S1, including BA 1, 2, and 3) and the secondary somatosensory area (S2). Two other pathways identified in half of the subjects included S1 and a classic sensory-transduction area (Brodmann Area 5), and S1 or S2 and the dorsal aspect of the primary motor area (M1). The activations in S1, S2, and M1 evoked by median-nerve stimuli are well-documented by MEG.

The most important features of the DCBF approach arise from incorporating the lead-field vectors of two simultaneously-activated neuronal sources into a single spatial filter. With this novel beamformer, we were able to successfully compute optimal dipole weights, orientations, and pseudo-Z-scores, eliminating time-consuming searches that hindered the previous dual-beamformer approach. In addition, by utilizing a powerful Powell search with a taboo list, we were able to reconstruct optimal source dipoles quickly without the use of a priori information. The changes and optimizations we made decreased the total computing time from tens of hours to less than 15 minutes, making the DCBF a viable and useful MEG source localization method for correlated sources. Future directions include extending the DCBF framework to three or four beams to find tightly correlated and complex networks of activity. The DCBF can also be migrated from a time-domain analysis to a frequency domain or time-frequency (wavelet) domain analysis to reduce the effects of noise and phasing.

Time Course, Correlation, and Orientation Determination Using the Enhanced Multi Core Beamformer (eMCBF) Algorithm for Sensor Array Signal Processing In another aspect, techniques, apparatus and systems are described for implementing an enhanced multi-core beamformer (MCBF) reconstruction. The orientation (direction) of the signals can be detected and allow correlation and reconstruction of multiple interfering sources at the same time. When two or more sources are in close proximity to one another, by tracing the orientation of the signal, the origins of the sources can be separated and precisely located. This feature can greatly enhance the clinical utility of the technology in situations like stroke, mild traumatic brain injury, and other brain function related disorders and diseases. Furthermore, the eMCBF can accurately obtain the individual source time-courses whereas previous MCBF can only obtain the common mode among multiple source time-courses. Such improvement will allow faithful reconstruction of the source temporal dynamics for individual neuronal sources which is important, for example, in the clinical diagnosis of epilepsy in which primary epilepsy source and propagations often co-exist in the data. eMCBF can also be used to recover source information from any types of sensor arrays, including radar, sonar, astronomical telescopes; magnetotelluric arrays for geologic exploration of water, oil, or minerals in the earth; optical and other electromagnetic arrays, and others.

The eMCBF uses the full dual-source covariance matrix, instead of a single eigenvector, when determining the beamformer weighting matrix, preventing undesired amplitude suppression and allowing reconstruction of individual time-courses without distortion. Thus, the eMCBF makes it possible to define and compute source correlation. In comparison, the use of the MCBF (2010-340) source orientations leads to a rank 1 beamformer weight, resulting in scaled copies of a single time-course representing a common mode of the sources. Furthermore, a single eigenvector can only capture either the correlated or uncorrelated part of the signal and is not sufficient to span the entire signal subspace, leading to incorrect estimates of source amplitude in the presence of correlated sources.

Magnetoencephalography (MEG) is a functional imaging modality that directly detects neuronal activity with millisecond temporal resolution. Reconstruction of source-space neural activity requires an adequate forward model based on the sensor and conductivity distribution (related to head geometry) and subsequent inverse modeling with the actual neuromagnetic recordings. Since the MEG inverse problem does not have a unique solution, assumptions about the sources (i.e. source modeling) must be made to properly localize and reconstruct sources of neuronal activity. The conventional single beamformer (SBF), a type of adaptive spatial filter, reconstructs sources with high spatial accuracy under poor signal-to-noise ratio (SNR) conditions, but assumes that the neuronal sources are uncorrelated. This assumption is not ideal since neural responses commonly involve communication between multiple sources within the same or across different neuronal networks. Many modified beamformer approaches have been proposed to overcome this limiting assumption.

The nulling beamformer (NB) and the coherent source suppression model (CSSM) seek to deal with correlated sources by constraining the beamformer gain for a single source to zero at pre-determined interfering locations. While the NB and CSSM can successfully handle correlated sources individually given the appropriate nulling constraints (location of interfering sources), multiple computations of source beamformer weights are still required to determine source correlation. The array-gain constraint minimum-norm filter with recursively-updated gram matrix (AGMN-RUG) spatial filter seeks to improve the spatial reconstruction of both uncorrelated and correlated sources by optimizing the gram matrix with the actual biomagnetic measurements. Though the AGMN-RUG spatial filter does not require a priori information and is quite powerful with only a few iterations of the recursive algorithm, measurements with high SNR are necessary for it to perform effectively. Thus, the beamformer is well-suited to study neural response to evoked stimulation, but is not ideal for studying brain activities that are not time- or phase-locked to stimuli.

The dual source beamformer (DSBF) seeks to reconstruct correlated sources by using spatial filters formulated from a linear combination of two sources' lead-field vectors. The technique requires non-linear optimization of source orientation angles and source amplitude weighting, in addition to a brute-force search across all possible source dipole combinations. This approach has a high computational cost, which greatly limits its application in practice. Furthermore, source time-course retrieval yields only a single, combined waveform for both sources. Also, the output from the DSBF spatial filter is compromised when sources are poorly, correlated, while its inability to produce individual source time-courses limits the quantitative measurement of source correlation.

The above described dual-core beamformer (DCBF) addresses many of the limitations of the DSBF developed by Brookes and colleagues. The DCBF implements the DSBF with a vector description, eliminating the need for non-linear searches of source orientations and source weighting. Furthermore, pairing the DCBF with a Powell search optimization algorithm allows quick localization of the correlated source pairs. However, our simulations demonstrated that the estimation of source amplitudes with DCBF grows inaccurate as correlation values decrease since time-course reconstruction only generates a single signal (scaled accordingly for each source). Though DCBF provides an effective way to identify source pairs, the measurement statistic (pseudo-Z-score) obtained is dependent on both source power and source correlation and does not exclusively quantify correlation between sources.

Ideally, in addition to localizing active sources, a quantitative measure of correlation is desired to obtain a more complete understanding of neuronal networks. Such a measure (e.g. power correlation) would more completely characterize highly sophisticated networks. In this manuscript, we propose an enhanced dual-core beamformer (eDCBF), which is capable of accurately estimating the source covariance matrix from multiple sources, providing a proper measure of correlation in addition to individual source time-courses without amplitude suppression. Once sources are localized, their correlation can be found without time-course reconstruction, allowing the eDCBF to handle large datasets quickly and requiring little memory. If desired, the eDCBF also provides a simple way of computing correlations in frequency bands of interest. Moreover, eDCBF's improved design offers robustness to a wide range of both source correlations and SNR. Finally, the eDCBF framework may be generalized to effectively account for the presence of multiple sources.

The mathematical formulation of the eDCBF and extension to the multi-core beamformer (MCBF) are first presented to fully demonstrate the design of the new spatial filter. In simulations we demonstrate that the eDCBF spatial filter is robust to a wide range of correlations, SNRs, source locations, and various source temporal dynamics. Using a three-core MCBF filter, we further demonstrate how additional sources of interference can be accounted for once source localization is performed. Finally, we cross-validate our findings from the simulations in an analysis of a human MEG recording during a stereo-auditory stimulation task, showing that the eDCBF produces meaningful correlation estimations and accurate time courses.

General Lead-Field Model:

Let b(t) be an m×1 vector of sensor measurements at time t, n(t) be an m×1 vector of sensor noise measurements, and s(t) be a 2p×1 matrix of vector source amplitudes, where m is the number of sensors and p is the number of pre-defined dipolar sources. Let the lead-field matrix defined in two directions θ and Φ for the $i^{th}$ source be denoted by the m×2 matrix $L_i=[1_{\theta,i}\ 1_{\Phi,i}]$. In the spherical MEG forward head model, θ and Φ represent the two tangential orientations for each dipole location, whereas in a realistic MEG forward model using the boundary element method (BEM), the θ and Φ orientations are obtained as the two dominant orientations from the singular value decomposition (SVD) of the m×3 lead-field matrix for each dipole, as previously documented (Huang et. al., 2006). The composite lead-field matrix or gain matrix is defined as the m×2p matrix $L=[L_1\ L_2\ L_3\ \ldots\ L_p]$. The MEG signal equation can be written as:

$$b(t)=L_s(t)+n(t) \qquad (22)$$

Taking the covariance of (1) and assuming that the noise and signal are uncorrelated leads to the covariance relationship:

$$R_b=LR_s^PL^T+R_n \qquad (23)$$

$R_b$ is the m×m sensor covariance matrix, $R_s^P$ is the 2p×2p source covariance matrix, and $R_n$ is the m×m noise covariance matrix.

Previous Dual-core Beamformer Formulation:

The DCBF was developed assuming the presence of two sources. Let $L_1$ and $L_2$ define the lead-field matrices of the two sources of interest. The dual-core lead-field matrix is expressed as the m×4 matrix $L_d=[L_1\ L_2]$. The DCBF weighting matrix is then defined as the m×1 vector $W_d$ designed such that:

$$\hat{s}(t)=v_1 W_d^T b(t) \quad (24)$$

where $\hat{s}(t)$ represents the 4×1 vector of estimated source time-courses in both the θ and Φ directions. $v_1$ is defined as a 4×1 vector containing both optimal non-normalized 2×1 source orientations $\eta_1$ and $\eta_2$:

$$v_1 = \begin{pmatrix} \eta_1 \\ \eta_2 \end{pmatrix} \quad (25)$$

$v_1$ is obtained by computing the eigenvector associated with the weakest eigenvalue of $Q_{dual}=L_d^T R_b^{-1} L_d$, where the dual-source power $P_{opt}$ is represented by the inverse of the eigenvalue. The DCBF solution for the weighting matrix was shown to be:

$$W_d=P_{opt} R_b^{-1} L_d v_1 \quad (26)$$

The DCBF orientations from (25) reduce $L_d$ to a rank 1 scalar lead-field matrix leading to an m×1 beamformer weight (26), resulting in scaled copies of a single time-course to represent both sources. Furthermore, a single eigenvector of $Q_{dual}$ ($v_1$) can only capture either the correlated or uncorrelated part of the signal and is not sufficient to span the entire signal subspace, leading to incorrect estimates of source amplitude in the presence of correlated sources.

Enhanced Dual-core Beamformer Formulation:

The enhanced Dual-core Beamformer (eDCBF) offers a novel solution to overcome the deficits of the previous DCBF. The eDCBF dual-core lead-field matrix is expressed identically to the original DCBF. Instead of using the DCBF m×1 weighting vector, the eDCBF weighting matrix is defined as the m×4 matrix $W_d=[W_1\ W_2]$, where $W_i$ are the individual weighting matrices for each source, ensuring no reduction in rank and enabling the computation of unique source time-courses and correlation. The eDCBF weighting matrix is designed such that:

$$\hat{s}(t)=W_d^T b(t) \quad (27)$$

$\hat{s}(t)$ is the 4×1 vector of unique estimated dual-source time-courses in both the θ and Φ directions. As a measure of source strength and activity, the 4×4 eDCBF estimated dual-source covariance matrix $R_{\hat{s}}$ is determined by taking the covariance of (27):

$$R_{\hat{s}}=\langle \hat{s}(t)\hat{s}(t)^T \rangle = W_d^T R_b W_d \quad (28)$$

The constraints of the vector minimum-variance beamformer, consistently shown to produce accurate beamformer reconstruction with single sources, may be used to derive the eDCBF weighting matrix $W_d$:

$$W_d=\arg_{W_d}\min tr\{W_d^T R_b W_d\} \text{ subject to } W_d^T L_d=I \quad (29)$$

The matrix product $W_d^T L_d$ represents the spatial filter output from two unit-magnitude impulse currents. The linear constraint $W_d^T L_d=I$ ensures that each weighting vector $W_i$ passes signal from its respective source while not passing signal from the second source. Furthermore, the trace of the beamformer output source power $W_d^T R_b W_d$ is minimized to suppress both noise and additional source contributions. However, no assumptions are made about the correlation between the two sources of interest. In fact, the correlation can take on any value from 0 for uncorrelated sources to 1 for completely synchronized sources. The solution for the minimization problem may be obtained by minimizing the Lagrangian with Lagrange multiplier k:

$$\mathcal{L}(W_d,\kappa)=tr\{W_d^T R_b W_d+(W_d^T L_d-I)\kappa\} \quad (30)$$

The derivative of the Lagrangian may be computed using the matrix derivative identities $$\frac{\partial}{\partial X} tr\{X^T A\} = A \text{ and } \frac{\partial}{\partial X} tr\{X^T AX\} = AX + A^T X: \quad (31)$$

$$\frac{\partial \mathcal{L}(W_d,\kappa)}{\partial W_d} = 2R_b W_d + L_d \kappa = 0$$

$$W_d = -\frac{R_b^{-1} L_d \kappa}{2} \quad (32)$$

Substituting the unit-gain constraint $W_d^T L_d=I$ into (32) yields:

$$\kappa=-2(L_d^T R_b^{-1} L_d)^{-1} \quad (33)$$

$$W_d=R_b^{-1} L_d (L_d^T R_b^{-1} L_d)^{-1} \quad (34)$$

The eDCBF estimated dual-source covariance matrix $R_{\hat{s}}$, which is equal to the inverse of the DCBF $Q_{dual}$, may be obtained by substituting the derived eDCBF beamformer weight (34) into (28):

$$R_{\hat{s}}=W_d^T R_b W_d=(L_d^T R_b^{-1} L_d)^{-1} \quad (35)$$

The eDCBF time-courses are obtained by substituting the derived eDCBF beamformer weight from (23) into (16):

$$\hat{s}(t)=W_d^T b(t)=(L_d^T R_b^{-1} L_d)^{-1} L_d^T R_b^{-1} b(t)=R_{\hat{s}} L_d^T R_b^{-1} b(t) \quad (36)$$

The eDCBF uses the full dual-source covariance matrix ($R_{\hat{s}}$ or $Q_{dual}^{-1}$) instead of a single dual eigenvector when determining the weighting matrix, preventing undesired amplitude suppression and allowing reconstruction of unique time-courses. Thus, the eDCBF makes it possible to define and compute source correlation.

eDCBF Estimated Correlation Reconstruction:

The eDCBF estimated vector covariance matrix $R_{\hat{s}}$ can be expressed as:

$$R_{\hat{s}} = \begin{bmatrix} \langle \hat{s}_1(t)\hat{s}_1(t)\rangle \bar{\eta}_1 \bar{\eta}_1^T & \langle \hat{s}_1(t)\hat{s}_2(t)\rangle \bar{\eta}_1 \bar{\eta}_2^T \\ \langle \hat{s}_2(t)\hat{s}_1(t)\rangle \bar{\eta}_2 \bar{\eta}_1^T & \langle \hat{s}_2(t)\hat{s}_2(t)\rangle \bar{\eta}_2 \bar{\eta}_2^T \end{bmatrix} \quad (37)$$

where $\hat{s}(t)$ are the estimated scalar source time-courses and $\bar{\eta}_i$ are the 2×1 normalized orientations for the two sources. The two diagonal 2×2 sub-matrices of $R_{\hat{s}}$ are of the same form as SBF vector covariance matrices. Thus, the eigenvectors corresponding to the maximum eigenvalues (signal-related) of these sub-matrices contain the source orientations, while the eigenvectors corresponding to the minimum eigenvalues (noise-related) contain the noise orientations. The 4×2 source orientation matrix ψ is used to reduce the 4×4 vector source covariance matrix to the 2×2 estimated dual-source scalar covariance matrix $\tilde{R}_{\hat{s}}$:

$$\psi = \begin{pmatrix} \bar{\eta}_1 & 0 \\ 0 & \bar{\eta}_2 \end{pmatrix} \quad (38)$$

$$\tilde{R}_{\hat{s}} = \psi^T R_{\hat{s}} \psi \quad (39)$$

The orientation matrix also allows scalar source time-course recovery:

$$\tilde{s}(t)=\psi^T W_d^T b(t) \quad (40)$$

The estimated dual-source power correlation $\hat{\chi}_{12}$ may be computed from:

$$\hat{\chi}_{12} = \frac{\hat{R}_{\hat{s}}(1,2)^2}{\hat{R}_{\hat{s}}(1,1)\hat{R}_{\hat{s}}(2,2)} \quad (41)$$

Amplitude correlation $\hat{\chi}_{12}{}^a$ can be computed as the square root of (41).

eDCBF Transformed Correlation Reconstruction:

Often, it is desirable to examine the source activity in a certain frequency band or envelope of the source signals. The eDCBF weighting matrix $W_d$ can be derived from either the transformed or original sensor recordings. Use of the original recordings allows determination of source orientations and $W_d$ based on the complete source power spectrum, which is more representative of true source activity. Furthermore, the eDCBF provides a straightforward way to compute correlations and time courses when $W_d$ has been derived from the original signal. $\hat{s}_\xi(t)$, the transformed time courses of $\hat{s}(t)$, are defined by transforming (36) in the time-domain:

$$\hat{s}_\xi(t) = \xi[\hat{s}(t)] = W_d{}^T \xi[b(t)] = W_d{}^T b_\xi(t) \quad (42)$$

where $b_\xi(t)$ are the transformed sensor time-courses and $\xi$ is the operator of the transformation. The transformed source covariance matrix $R_{\hat{s}}{}^\xi$ may be computed with the transformed sensor covariance matrix $R_b{}^\xi = \langle b_\xi(t) b_\xi(t)^T \rangle$ without computation of source time-courses:

$$R_{\hat{s}}{}^\xi = \langle \hat{s}_\xi(t) \hat{s}_\xi(t)^T \rangle = W_d{}^T R_b{}^\xi W_d \quad (43)$$

The estimated correlation may be computed from the transformed source covariance matrix in the same fashion as (39) and (41). Furthermore, (42) and (43) hold for any linear transformations in the time domain.

eDCBF Regularized Correlation Reconstruction:

Use of the regularized beamformer has greatly improved the quality of beamformer signal time-course reconstruction. The eDCBF beamformer weight can be reformulated to obtain the regularized beamformer weight $W_d{}^r$ $$W_d{}^r = (R_b + \gamma I)^{-1} L_d (L_d{}^T (R_b + \gamma I)^{-1} L_d)^{-1} \quad (44)$$

where $\gamma$ is the regularization parameter that increases the full-width half-maximum of the beamformer point-spread function while reducing the amount of uncorrelated noise. Source time-courses may be reconstructed as:

$$\hat{s}_r(t) = (W_d{}^r)^T b(t) \quad (45)$$

Source correlation may be computed from the regularized estimated source covariance matrix $R_{\hat{s}}{}^r$ without computation of time courses using equations (39) and (41).

$$R_{\hat{s}}{}^r = \langle \hat{s}_r(t) \hat{s}_r(t)^T \rangle = (W_d{}^r)^T R_b W_d{}^r \quad (46)$$

Correlation and time courses in specific frequency bands may be computed by using the regularized beamformer weight $W_d{}^r$ in conjunction with (42) and (43).

eDCBF Noise-corrected Correlation Reconstruction:

The estimated dual-source covariance matrix can be heavily biased by the presence of noise, making true prediction of correlation difficult. Further investigation reveals that this bias can be corrected using the sensor noise covariance $R_n$. The expression for $R_b$ from (23) may be equivalently written as $R_b = \tilde{L} \tilde{R}_s{}^P \tilde{L}^T + R_n$, where the scalar composite lead-field matrix is given by $\tilde{L} = [l_1 \, l_2 \, \ldots \, l_p]$ and $\tilde{R}_s{}^P$ is the p×p scalar source covariance matrix. The m×1 vectors $l_i$ that comprise $\tilde{L}$ are the scalar lead-fields for each source along its true orientation $\bar{\eta}_i$ where $l_i = l_i \bar{\eta}_i$. By substituting this expression for $R_b$ into (28), it is evident that the estimated source covariance matrix $R_{\hat{s}}$ is composed of a noise-free component (first term on the right-hand-most side of (47)) and a noise-related component (second term on the right-hand-most side of (47)):

$$R_{\hat{s}} = \langle \hat{s}(t) \hat{s}(t)^T \rangle = W_d{}^T R_b W_d = W_d{}^T \tilde{L} \tilde{R}_s{}^P \tilde{L}^T W_d + W_d{}^T R_n W_d \quad (47)$$

The process of minimization and application of linear constraints result in weight vectors that satisfy $W_d{}^T l_i = 0$ for i: 3→p by assuming that the corresponding sources are uncorrelated with each other as well as the two sources of interest (Sekihara et al., 2002). The noise-free component then reduces to the 4×4 true dual-source vector covariance matrix $R_s$:

$$W_d{}^T \tilde{L} \tilde{R}_s{}^P \tilde{L}^T W_d = R_s \quad (48)$$

Equation (48) also remains valid when only two sources are present. When additional partially correlated sources exist, the multi-core extension presented in the next section must be used. Equation (47) then simplifies to:

$$R_{\hat{s}} = R_s + W_d{}^T R_n W_d \quad (49)$$

Substituting the derived beamformer weight (23) into (38) and solving for $R_s$ yields:

$$R_s = (I - R_{\hat{s}} L_d{}^T R_b{}^{-1} R_n R_b{}^{-1} L_d) R_{\hat{s}} \quad (50)$$

To obtain the noise-corrected correlation, an unbiased estimate of the noise covariance $R_n$ is essential. The true dual-source vector covariance matrix can then be reduced using the derived orientations to the 2×2 true dual-source scalar covariance matrix $\tilde{R}_s$ to compute the noise-corrected correlation value $x_{12}$:

$$\tilde{R}_s = \psi^T R_s \psi \quad (51)$$

$$x_{12} = \frac{\tilde{R}_s(1,2)^2}{\tilde{R}_s(1,1) \tilde{R}_s(2,2)} \quad (52)$$

Using the definition of the matrix $K = W_d{}^T R_n W_d (W_d{}^T R_b W_d)^{-1} = R_{\hat{s}} L_d{}^T R_b{}^{-1} R_n R_b{}^{-1} L_d$ from the original DCBF, (50) can be written as:

$$R_s = (I - K) R_{\hat{s}} \quad (53)$$

Thus, the relationship between the true dual-source vector covariance and the estimated dual-source vector covariance is dependent on the K matrix, which is inversely proportional to the source space SNR. As shown previously, the K-related dual-source pseudo-Z-score ($Z^K$) may be obtained by inverting the minimum eigenvalue of the K matrix:

$$Z^K = \min(\text{eig}(K))^{-1} \quad (54)$$

This pseudo-Z-score can be used as a measure of relative source activity. Alternatively, the power pseudo-Z-score may be computed by dividing the dual source power by the noise power:

$$Z^P = \frac{tr\{R_{\hat{s}}\}}{tr\{(L_d{}^T R_n{}^{-1} L_d)^{-1}\}} \quad (55)$$

The differences in the spatial profile of $Z^K$ and $Z^P$ will be investigated in the Results.

Extension to Multi-core Beamformer (MCBF):

As described above, using DCBF to model two sources is sufficient to reveal complex neuronal networks with many sources due to only partial suppression of the pseudo-Z-score. However, as shown by (48), the eDCBF can only account for two correlated sources in the presence of other uncorrelated sources. When multiple correlated sources exist, the correlation coefficient and time-course reconstruction are affected severely. Therefore, the model needs to be expanded to handle such environments.

A multi-core beamformer (MCBF) can be developed to account for additional sources. The technique can be described by a straightforward extension of the eDCBF. Starting from (23), the multi-core lead-field vector is defined as the m×2c matrix $L_m[L_1 L_2 \ldots L_C]$, where c is the desired number of sources to be modeled. The corresponding multi-core weighting vector is then defined as the m×2c matrix $Wm=[W_1 W_2 \ldots W_C]$. The solution to the multi-core weighting vector, $W_m$, is derived in an equivalent manner to (29) through (34):

$$Wm = R_b^{-1} L_m (L_m^T R_b^{-1} L_m)^{-1} \quad (56)$$

The derivations presented from (35) to (52) can be then applied to the multi-core beamformer to obtain the 2c×2c estimated multi-core vector covariance matrix $R_s$, the 2c×2c true multi-core vector covariance matrix $\tilde{R}_s$, the c×c estimated multi-core scalar covariance matrix $\hat{R}_s$, and the c×c true multi-core scalar covariance matrix $\tilde{R}_s$. The orientation vector ψ is defined as:

$$\psi = \begin{pmatrix} \bar{\eta}_1 & 0 & \ldots & 0 \\ 0 & \bar{\eta}_2 & \ldots & 0 \\ \vdots & \vdots & \ddots & \vdots \\ 0 & 0 & \ldots & \bar{\eta}_C \end{pmatrix} \quad (57)$$

The estimated pair-wise correlation $\hat{\chi}_{ij}$ and the noise-corrected pair-wise power correlation $\tilde{\chi}_{ij}$ between the $i^{th}$ and $j^{th}$ sources are given by:

$$\hat{\chi}_{ij} = \frac{\hat{R}_s(i,j)^2}{\hat{R}_s(i,i)\hat{R}_s(j,j)} \quad (58)$$

$$\tilde{\chi}_{ij} = \frac{\tilde{R}_s(i,j)^2}{\tilde{R}_s(i,i)\tilde{R}_s(j,j)} \quad (59)$$

Amplitude correlation can be computed as the square root of (58) and (59). The formulation of the MCBF is similar to that of the NB and CSSM except that instead of deriving the beamformer weight for only one source of interest at a time, the MCBF applies additional constraints to simultaneously find weights for all modeled sources. This feature allows correlation reconstruction of multiple interfering sources at the same time. The MCBF requires three degrees of freedom for spatial location and two degrees of freedom for orientation per core. Theoretically, if all signals from m sensors are linearly independent and signal-related (achieved at infinite SNR), the MCBF can model a maximum of m/5 sources. However, at the typical SNR of real measurements recorded on a modern MEG system, the number of signal-related independent spatial modes is approximately 40-50, allowing the MCBF to model a maximum of 8-10 sources. The MCBF is most appropriately used to determine source activity for a given set of sources that already have been accurately localized by methods utilizing a metric such as the DCBF pseudo-Z-score).

General Setup for Simulations:

To measure the performance of the eDCBF spatial filter for both correlation and temporal reconstruction, a series of computer simulations were conducted with a simulator designed to allow variation of the sources present (number, location, orientation) and their corresponding waveforms (frequency, amplitude, lag, duration, SNR), thereby providing vast flexibility for simulation execution.

Figure 12:
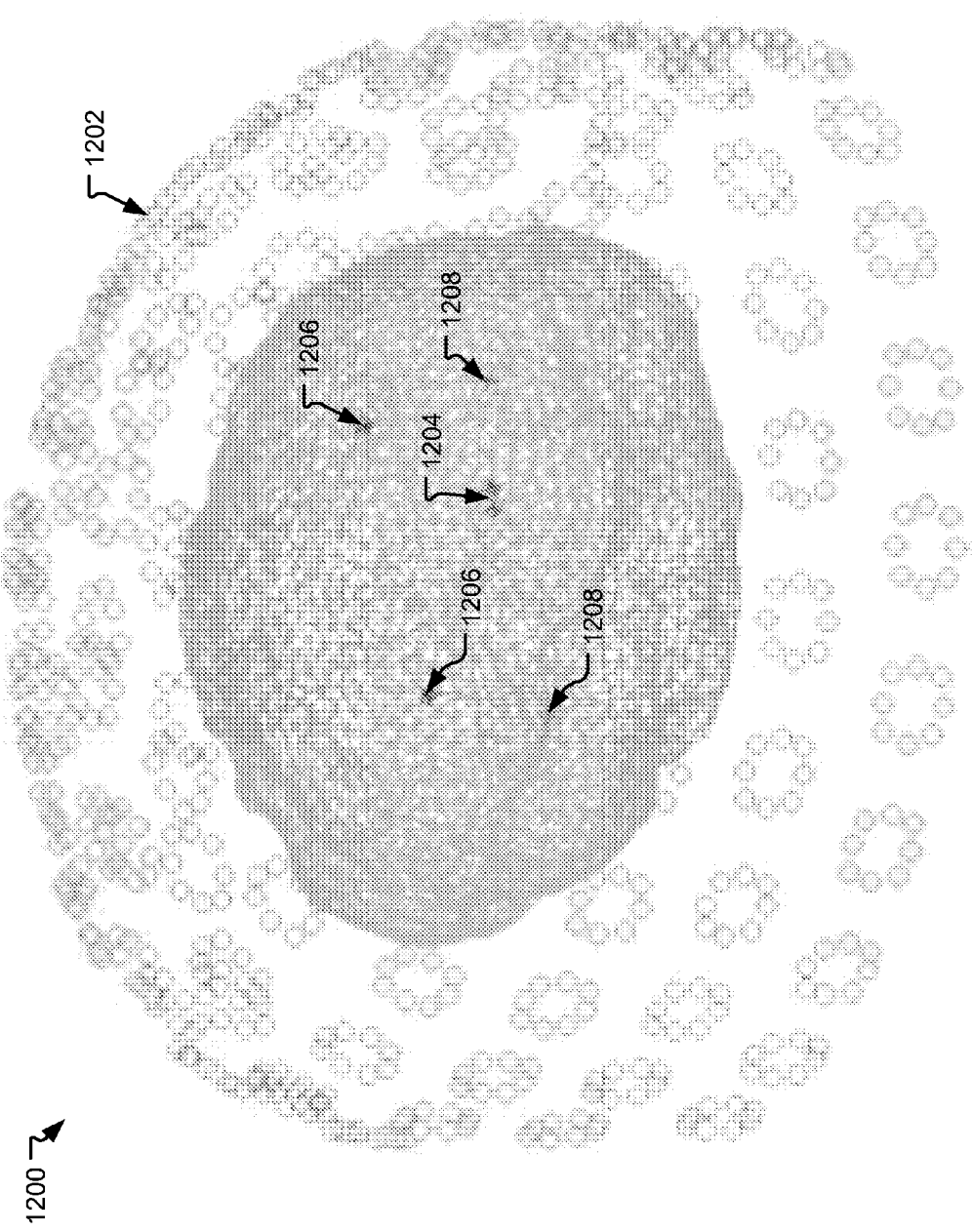
FIG. 12 shows an exemplary Source and Sensor Model. Green—MEG sensor groups. Blue—Posterior Cingulate Cortex dipoles. Black—Motor Cortex dipoles. Red—Auditory Cortex dipoles.

The source space was simulated with a grid covering the cortical gray matter with homogenous 5 mm spacing in the x, y, and z directions. The cortical boundaries were obtained from a healthy subject's T1-weighted anatomical MRI. The sensor configuration was based on the Elekta/Neuromag™ whole-head MEG system (VectorView), in which 306 sensors are arranged on a helmet-shaped surface (204 gradiometers and 102 magnetometers). The source-sensor configuration is shown in FIG. 12 (inner-skull surface represented by gray mesh).

To compute the forward model, the boundary element method (BEM) was employed where the inner-skull surface (from MRI) served as the BEM mesh (size 5 mm). SNR levels were adjusted by adding uncorrelated random Gaussian noise to the sensor waveforms, where the SNR was defined as the ratio of the Frobenius norm of the signal vector to that of the noise vector calculated over the interval with signal. Using the simulator, eDCBF correlation and time-course reconstruction were inspected over varying source coherence, SNRs, and temporal dynamics. Additional simulations were designed to test the eDCBF at various source separations as well as to investigate correlation estimation for the three-core MCBF.

Setup for SNR, Correlation, and Time-course Simulations:

Two source dipoles were placed in the left and right hemisphere auditory cortices. FIG. 12 shows an exemplary source and sensor model 1200. Green (1202) shows MEG sensor groups, Blue (1204) shows Posterior Cingulate Cortex dipoles, Black (1206) shows Motor Cortex dipoles, and Red (1208) shows Auditory Cortex dipoles. Their signals were composed of a 6-second inactive period followed by 6 seconds of a sinusoidal wave with amplitude of 5 nAm and frequency of 30 Hz (sampling rate 1000 Hz). The phase shift of the second source was varied from 0° to 90° in steps of 10° to test a wide range of correlations. Reconstruction of the estimated correlation and the noise-corrected correlation was carried out at SNRs of 4, 2, 1, 0.5, 0.25, and 0.167. Estimation of source amplitudes was carried out by FFT examination of extended length (50×) source time-course reconstructions over all phase lags and SNRs. To test time-course recovery of a more complicated signal, a linear chirp was utilized, wherein the frequency was varied from 5 to 10 Hz (and back) over a period of 5 seconds and the amplitude was modulated by a 0.1 Hz sinusoid. Noise-corrected correlation was computed for all SNRs and for source time-lags of 0.05, 0.1, 0.4 and 1 second. Source time-courses and RMS amplitudes were calculated at all time-lags and at an SNR of 4. Finally, Monte Carlo methods were employed to properly quantify the results' probability distribution (1000 simulations unless otherwise noted).

Setup for Location Simulations:

To test eDCBF reconstruction at varying source locations, the sinusoidal simulation from the previous section was performed for two additional sets of sources. Noise-corrected correlation values were computed for distantly-placed sources in the left and right hemisphere primary motor cortices with a separation of 70 mm and for closely-placed sources in the left and right posterior cingulate cortex (PCC) with a separation of 5 mm (FIG. 12). A set of 1000 randomly chosen source pairs was also tested for noise-corrected correlation accuracy at a fixed SNR of 4.

Setup for Three-core MCBF Simulation:

An additional simulation was designed to test MCBF performance for a core size of three. Sources were placed in the PCC and the left and right primary motor cortices. The right motor cortex source's phase lag ranged from 45° to 90° (in steps of 5°) whereas the PCC source's phase lag decreased from 45° to 0° (in steps of 5°), creating a variety of correlation conditions. The simulation was executed 1000 times to compute the noise-corrected correlation for the full SNR and correlation ranges.

Setup for Human MEG Auditory Study:

A stereo auditory test stimulus was designed to compare eDCBF correlation and time-course reconstruction in actual MEG measurements (200 epochs of evoked responses) to reconstruction using two-dipole fit, a method known to adequately represent neuronal activity in the auditory cortices. The test sound file consisted of 1800 ms of pre-stimulus silence followed by a 2000 ms stereo stimulus period. The stimulus consisted of a 500-Hz pure tone with a 40-Hz envelope modulated at 100% level. The modulation envelopes between the left and right channels were designed to be fully correlated. The intensities of the left and right channels were balanced for equal sensitivity for the left and right ears. The start and end of the stimulus epochs were smoothed with a cosine roll-off to prevent any artifacts. Magnetic fields evoked by auditory stimulation were measured using an Elekta/Neuromag™ whole-head MEG system (VectorView) with 204 gradiometers and 102 magnetometers in a magnetically shielded room (IMEDCO-AG, Switzerland). EOG electrodes were used to detect eye blinks and eye movements.

Intervals of 1400 ms of post-stimulus data and 200 ms of pre-stimulus data were used for analysis. Data were sampled at 1000 Hz and processed by MaxFilter to remove environment noise. Artifact-free MEG responses (n=181) were averaged with respect to the stimulus trigger. A BEM mesh of 5-mm size for the subject was generated from the inner-skull surface using a set of T1-weighted MRI images taken on a 1.5 T MRI scanner. Registration of MRI and MEG was performed using data obtained from the Polhemus Isotrak system prior to MEG scanning.

Reconstructions of MEG auditory recordings with the eDCBF, SBF, and dipole-fit modeling were compared to assess the accuracy and validity of the eDCBF reconstruction. SVD was used to separate the original sensor measurements into signal and noise components. The top eight singular modes were chosen as a conservative estimate of the noise-free signal based on manual inspection of the elbow-shaped region of the singular value spectrum. The remaining singular modes were considered to contain only the noise-related signal. The noise components were removed and replaced with white noise of the same power, resulting in an estimated SNR of 3.7 and allowing construction of a noise covariance matrix. A regularization parameter equal to 4% of the largest eigenvalue of $R_b$ was used for reconstruction with both the eDCBF and the vector SBF.

Dual-source localization was performed with a Nelder-Mead downhill simplex search for the maximum power pseudo-Z-score. The eDCBF regularized beamformer weight $W_d^r$ was computed and used with equations (45), (42), and (40) to generate unfiltered and low-pass filtered (<50 Hz) regularized time-courses for each source. Inter-hemispheric correlation values were computed from filtered time-courses, from the source covariance matrix presented in (43), and from the noise-corrected source covariance matrix. Vector-based SBF was also used to reconstruct unfiltered and filtered regularized time-courses for the source locations identified by the eDCBF. Inter-hemispheric correlations were computed with the reconstructed filtered regularized SBF time-courses for comparison.

Localization was also performed using a multi-start downhill simplex dipole-fit algorithm with a spherical head model. The fitted locations were further refined with a BEM forward model. The dipole-fit source time-course reconstruction was obtained by multiplying the pseudo-inverse of the gain matrix for the fitted dipoles and the sensor measurements. Inter-hemispheric correlations were computed with unfiltered and low-pass filtered dipole-fit source time-courses (<50 Hz). Correlations were also computed between filtered regularized reconstructions (eDCBF and SBF) and filtered time-courses obtained from dipole fit as a measure of time-course similarity.

Analysis of eDCBF Across Entire Correlation Range:

To test the performance of eDCBF across the entire range of possible correlations, a phase lag was introduced to the sinusoid of the second source. The simulation was performed with an SNR of 4, minimizing noise effects so that the eDCBF's sensitivity to correlation was emphasized. Source reconstruction was completed using estimated correlation reconstruction. Table 7 shows that eDCBF estimates of the sources' time-course correlations are highly accurate ($\epsilon$<0.003, $\sigma$≤0.0013, where $\epsilon$ is the error, and $\sigma$ is the standard deviation across Monte Carlo iterations) regardless of the actual value of the correlation. In addition, the low standard deviation demonstrates eDCBF's exceptional stability. Accuracy of source localization was not examined here, as it was already confirmed with the original DCBF.

Table 7 shows estimated correlation reconstruction for auditory dipole (SNR=4). Correlation averages and standard deviations determined using 1000 Monte Carlo simulations.

| θ Shift | χ (Actual) | χ (Estimated) | σ |
|---|---|---|---|
| 0° | 1.000 | 0.997 | 3.83E−05 |
| 10° | 0.970 | 0.967 | 1.96E−04 |
| 20° | 0.883 | 0.881 | 4.44E−04 |
| 30° | 0.750 | 0.748 | 7.96E−04 |
| 40° | 0.587 | 0.585 | 1.03E−03 |
| 50° | 0.413 | 0.412 | 1.22E−03 |
| 60° | 0.250 | 0.250 | 1.21E−03 |
| 70° | 0.117 | 0.117 | 9.85E−04 |
| 80° | 0.030 | 0.030 | 5.47E−04 |
| 90° | 0.000 | 0.000 | 1.07E−04 |

Figure 13:
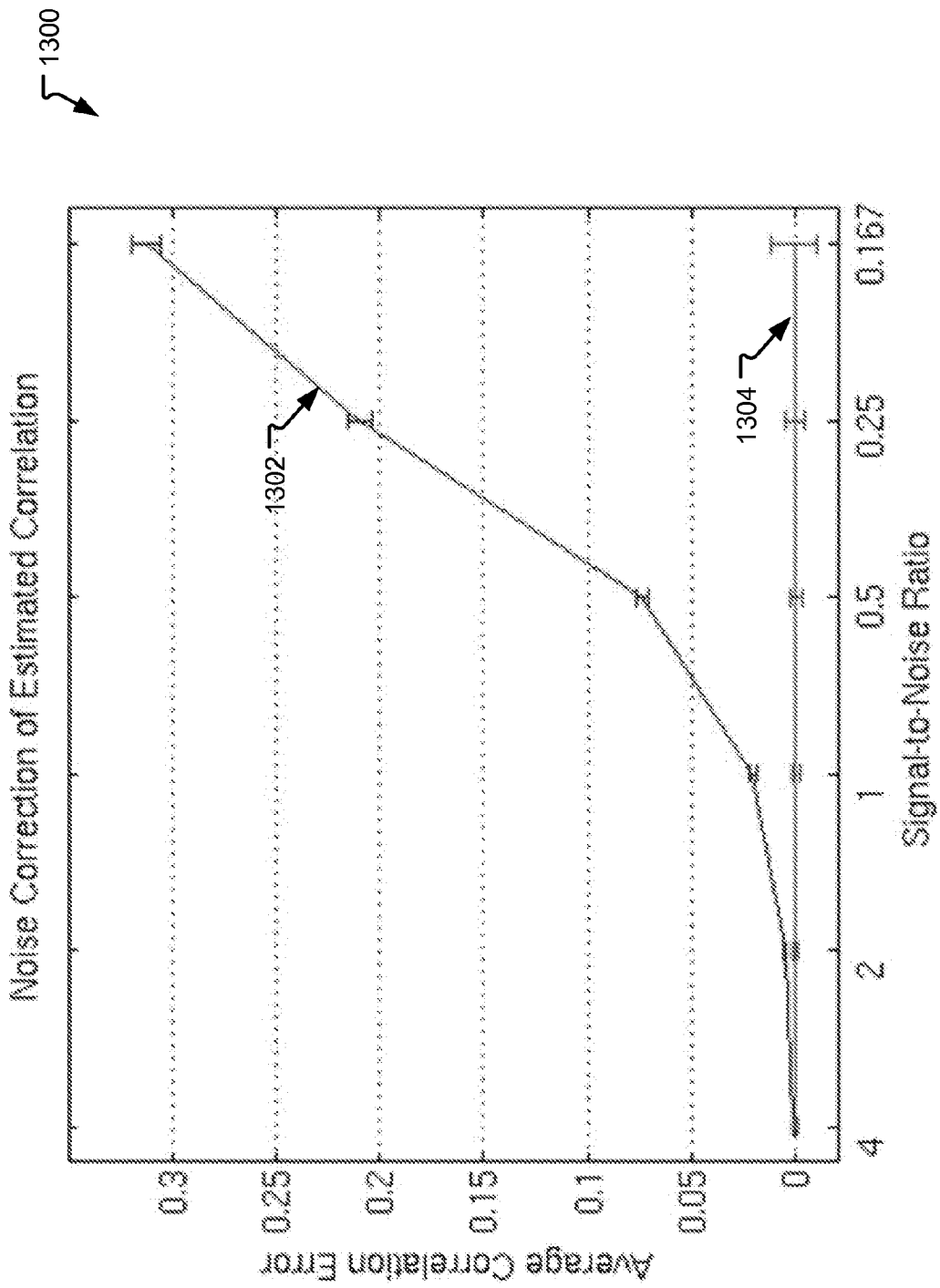
FIG. 13 shows an estimated (blue) and Noise-corrected (red) correlation reconstruction errors and standard deviations (error bars) for auditory dipoles. Correlation values determined using 1000 Monte Carlo simulations.

Examination of eDCBF Performance Across SNR Range:

Real-world noise commonly dominates the underlying signal, frequently posing a problem for beamformers. Therefore, we characterized eDCBF performance across a range of SNR values. The following simulation allowed comparison of the estimated and noise-corrected correlation reconstruction from (31) and (42). We observed that even though the estimated correlation works well initially, as SNR drops below 1, the accuracy of eDCBF estimated correlations fell to unacceptable levels. By a SNR level of 0.167, the filter became practically ineffective and was unable to appropriately resolve the underlying signal ($\bar{\epsilon}$<0.32), where $\bar{\epsilon}$ is the averaged correlation error over all phase shifts for a given SNR. From the noise time-courses (added to sensor waveforms to create the desired SNR), an unbiased estimate of the noise covariance matrix was used to examine the noise-corrected correlation. The correction allowed the beamformer to perform successfully at the entire range of SNR and correlation values ($\bar{\epsilon}<0.0008$, $\bar{\sigma}<0.011$), where $\bar{\sigma}$ is the averaged Monte Carlo standard deviation across all phase shifts in a given SNR 1300 as shown in FIG. 13, rendering eDCBF an extremely robust and flexible beamformer filter given a reasonably accurate estimation of the noise covariance. FIG. 12 shows estimated (blue) 1302 and Noise-corrected (red) 1304 correlation reconstruction errors and standard deviations (error bars) for auditory dipoles. Correlation values determined using 1000 Monte Carlo simulations.

Figure 14:
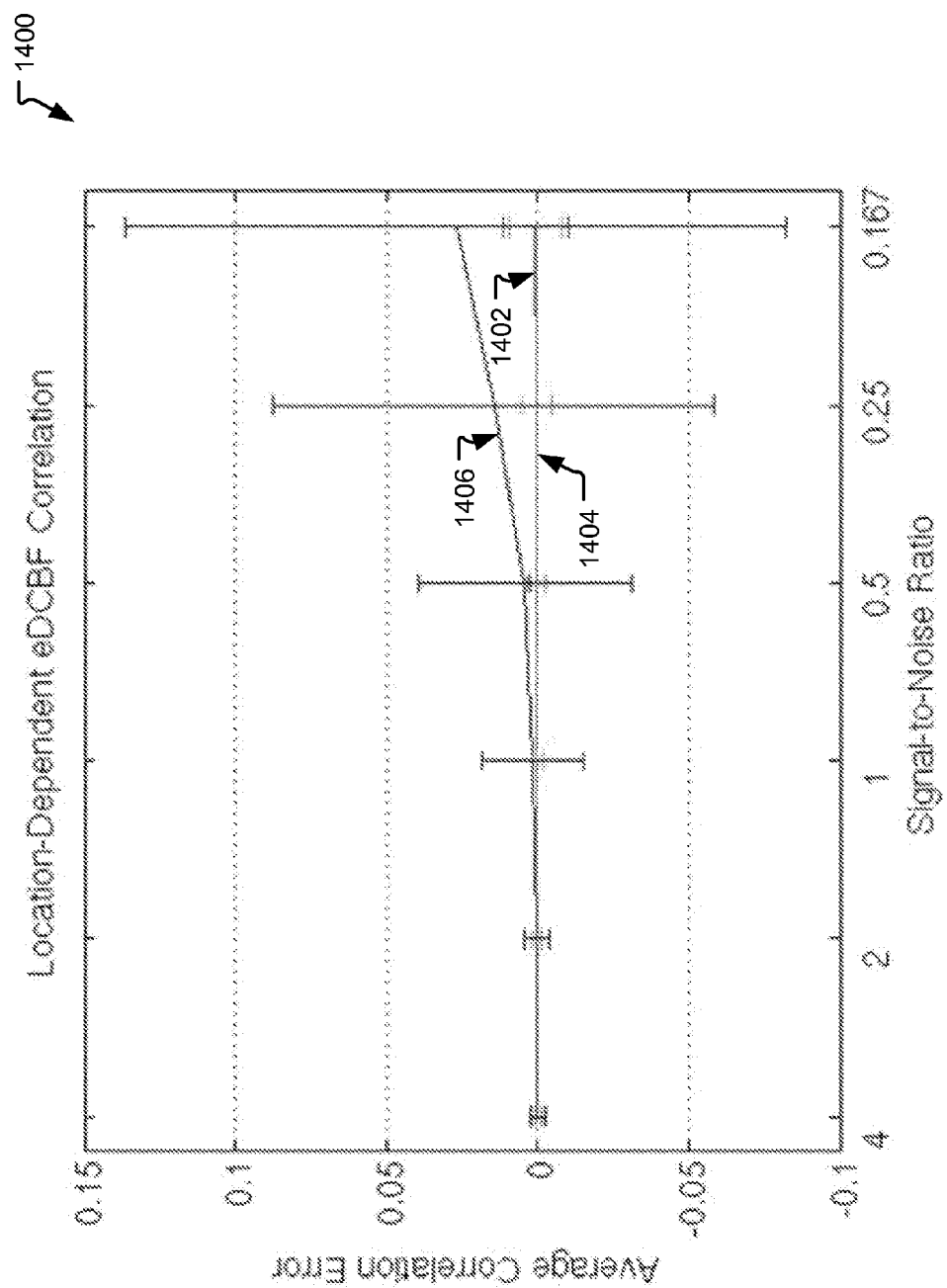
FIG. 14 shows Noise-corrected correlation reconstruction errors and standard deviations (error bars) for auditory cortex (red), motor cortex (green), and posterior cingulate cortex (blue) dipoles. Correlation values determined using 1000 Monte Carlo simulations.

Validation of eDCBF Performance Regardless of Source Location:

The sensitivity of the eDCBF filter to the location of the two sources was investigated by examining three cases: a pair of distantly-spaced dipoles, a pair of closely spaced dipoles, and a pair of randomly placed dipoles. For distant dipoles, we observed that the correlation reconstruction worked precisely throughout the entire SNR and correlation ranges ($\bar{\epsilon}<0.0005$, $\bar{\sigma}<0.009$). When dipoles were closely placed (PCC dipoles spaced only 5 mm apart), a hindrance for beamformer operation at low SNR, the eDCBF still performed effectively. At SNRs at or above 0.5, the eDCBF was reasonably accurate ($\bar{\epsilon}<0.005$, $\bar{\sigma}<0.036$), while at SNRs of 0.25 or lower it slightly overestimated the correlation value ($\bar{\epsilon}<0.027$, $\bar{\sigma}<0.11$) due to bias in the noise covariance estimate at very low SNRs (FIG. 14). FIG. 14 shows noise-corrected correlation reconstruction errors and standard deviations (error bars) for auditory cortex (red) 1402, motor cortex (green) 1404, and posterior cingulate cortex (blue) 1406 dipoles. Correlation values determined using 1000 Monte Carlo simulations. Finally, the eDCBF filter still performed accurately when dipole pairs were chosen randomly ($\bar{\epsilon}<0.0002$, $\bar{\sigma}<0.003$).

Figure 15:
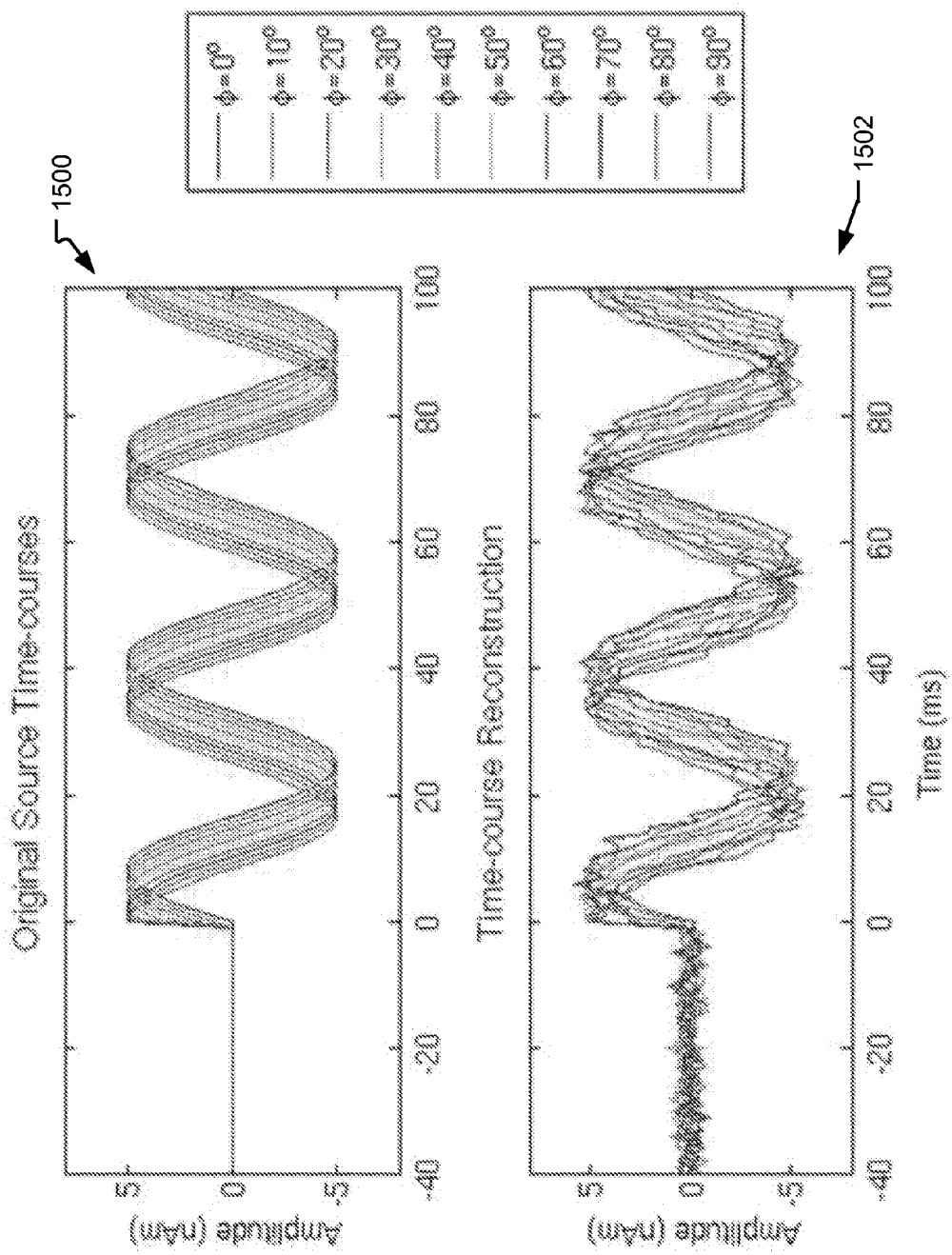
FIG. 15 shows Sinusoidal Time-course Reconstruction at phase shifts ranging from 0 to 90 degrees. Top panel—simulated source waveforms. Bottom panel—eDCBF time-courses.

Time-Course Reconstruction Sinusoid/Chirp Source Waveforms:

For most of the simulations, a sinusoid wave was used to construct the source signal. To investigate the precision of the reconstructed waveform, we examined the accuracy of the reconstructed amplitude as the SNR and phase lag were varied, which is another concern associated with previous dual beamformers. FIG. 15 shows a set of reconstructed waveforms (for the entire range of phase shifts) at SNR of 4 computed from (40). Figure shows sinusoidal Time-course Reconstruction at phase shifts ranging from 0 to 90 degrees: Top panel—simulated source waveforms 1502; and Bottom panel 1504 eDCBF time-courses.

As shown in Table 8, eDCBF reconstructed the amplitude with the same success regardless of SNR or correlation value, underestimating by more than 1% only in a single case. The small bias in amplitude estimation occurs due to a rank deficient sensor covariance matrix before the addition of noise. Amplitudes estimated from the eDCBF were far more accurate than those from the previous DCBF, which were suppressed by an average of 12.5%.

Table 8 shows amplitude values for left auditory cortex dipole (results equivalent for right dipole). Amplitude values determined using 100 Monte Carlo simulations.

| | | SNR | | | | |
|---|---|---|---|---|---|---|
| | | 4 | 2 | 1 | 0.5 | 0.25 |
| θ Shift | χ (Actual) | | | Amplitude | | |
| 0° | 1.000 | 4.99 | 4.99 | 4.99 | 4.99 | 4.99 |
| 10° | 0.970 | 4.99 | 5.00 | 4.99 | 4.99 | 4.99 |
| 20° | 0.883 | 4.99 | 4.99 | 5.00 | 4.99 | 4.99 |
| 30° | 0.750 | 4.99 | 5.00 | 5.00 | 4.99 | 4.99 |
| 40° | 0.587 | 4.99 | 4.99 | 4.99 | 4.99 | 4.99 |
| 50° | 0.413 | 4.99 | 4.99 | 5.00 | 4.99 | 4.99 |
| 60° | 0.250 | 4.99 | 4.99 | 5.00 | 4.99 | 4.98 |
| 70° | 0.117 | 4.99 | 5.00 | 4.99 | 4.99 | 4.98 |
| 80° | 0.030 | 4.99 | 4.99 | 4.99 | 4.99 | 4.97 |
| 90° | 0.000 | 4.99 | 4.99 | 4.99 | 4.99 | 4.93 |

Figure 16:
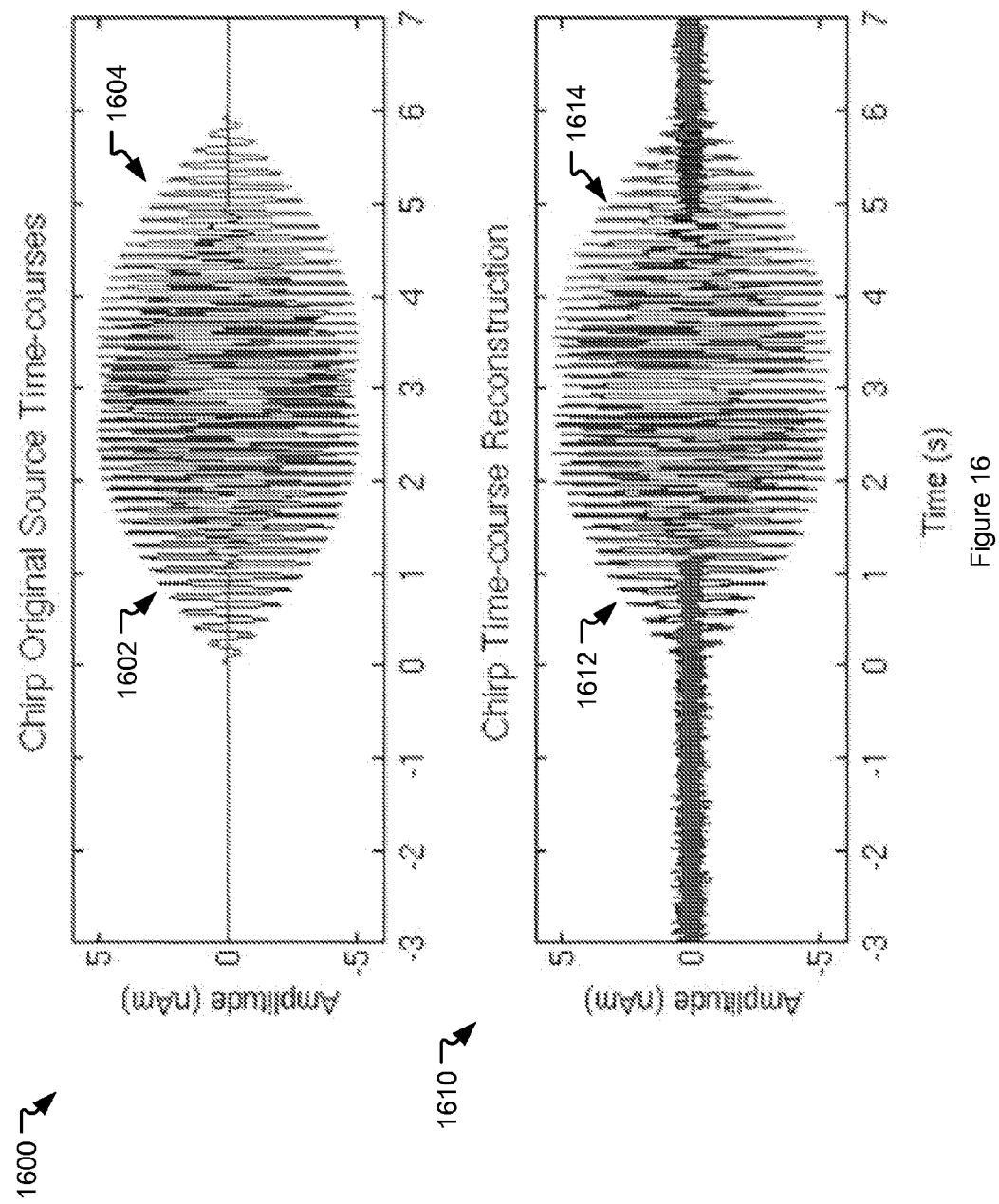
FIG. 16 shows Chirp Time-course Reconstruction at 1 second time lag. Top panel—original source waveforms. Bottom panel—eDCBF time-courses. Blue—left auditory cortex. Green—right auditory cortex.
Figure 17:
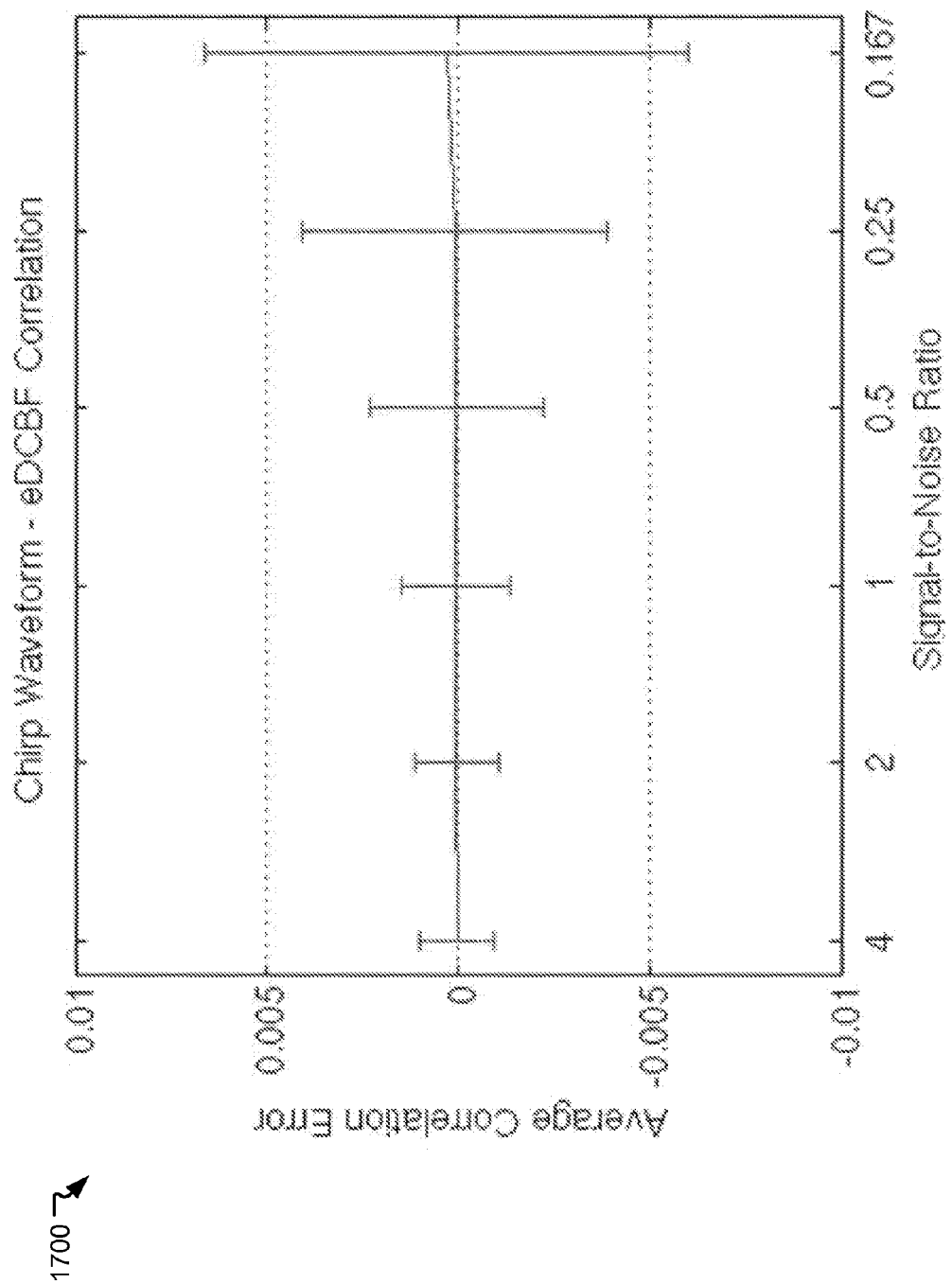
FIG. 17 shows Noise-corrected correlation reconstruction errors and standard deviations (error bars) for chirp waveforms at different time-lags. Correlation values determined using 1000 Monte Carlo simulations.

Since neuronal signals typically contain complex features, a more sophisticated waveform in the form of a linear chirp was also considered. To simulate various correlations, a series of time lags were introduced to the chirp present in the second source. FIG. 16 shows an example of the reconstructed waveform for a one-second time-lag at a SNR of 4 for the sensor waveforms. FIG. 16 shows Chirp Time-course Reconstruction at 1 second time lag: Top panel 1600 original source waveforms; and Bottom panel 1610 eDCBF time-courses. Blue (1602 and 1612)—left auditory cortex. Green (1604 and 1614)—right auditory cortex. To quantitatively asses the reconstruction, an RMS amplitude measure was employed. When comparing the original waveform's amplitude with the reconstructed waveform (for the example above), it was accurate to 99.9%. The accuracy of the correlation computation was also tested (1000 Monte Carlo simulations). FIG. 17 shows that the eDCBF successfully estimates the correlation for any combination of SNR and time lag ($\bar{\epsilon}<0.0004$, $\bar{\sigma}<0.007$). FIG. 17 shows Noise-corrected correlation reconstruction errors and standard deviations (error bars) for chirp waveforms at different time-lags (1700). Correlation values determined using 1000 Monte Carlo simulations.

Figure 18:
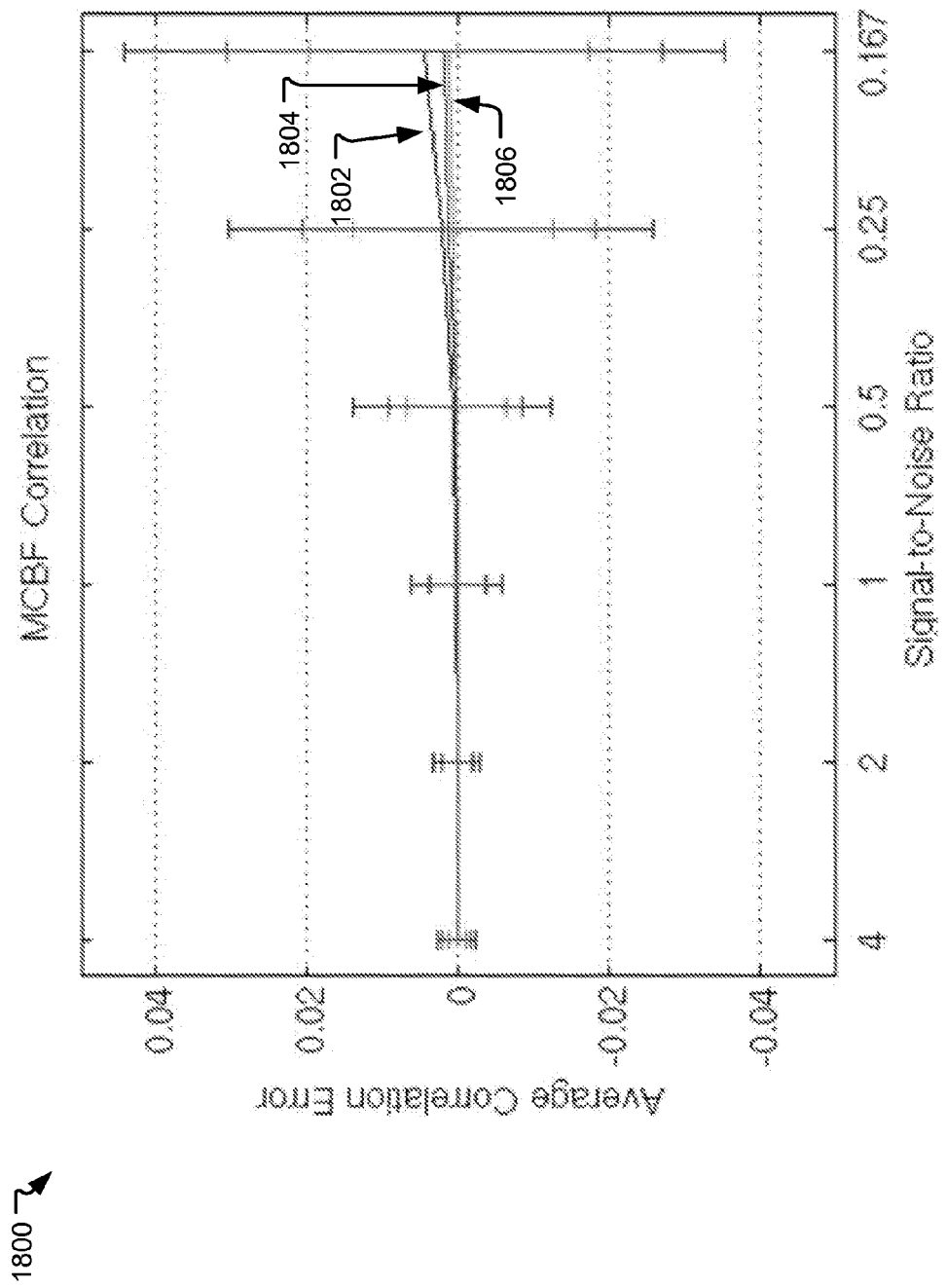
FIG. 18 shows Pair-wise three-core MCBF noise-corrected correlation reconstruction errors and standard deviations (error bars). Blue—left motor cortex and posterior cingulate cortex. Green—left motor cortex and right motor cortex. Red—right motor cortex and posterior cingulate cortex. Correlation values determined using 1000 Monte Carlo simulations.

Three-Source Simulation with MCBF:

The last simulation examined the performance of the MCBF filter when reconstructing three simultaneously-active correlated sources. Currently, no beamformer method is able to properly address this issue. MCBF performance in reconstructing the source correlation values for all three dipole combinations can be seen in FIG. 18. For any given condition, MCBF properly reconstructed all correlation values ($\bar{\epsilon}<0.005$, $\bar{\sigma}<0.04$). FIG. 18 shows Pair-wise three-core MCBF noise-corrected correlation reconstruction errors and standard deviations (error bars) 1800: Blue (1802)—left motor cortex and posterior cingulate cortex. Green (1804)—left motor cortex and right motor cortex. Red (1806)—right motor cortex and posterior cingulate cortex. Correlation values determined using 1000 Monte Carlo simulations.

Figure 19:
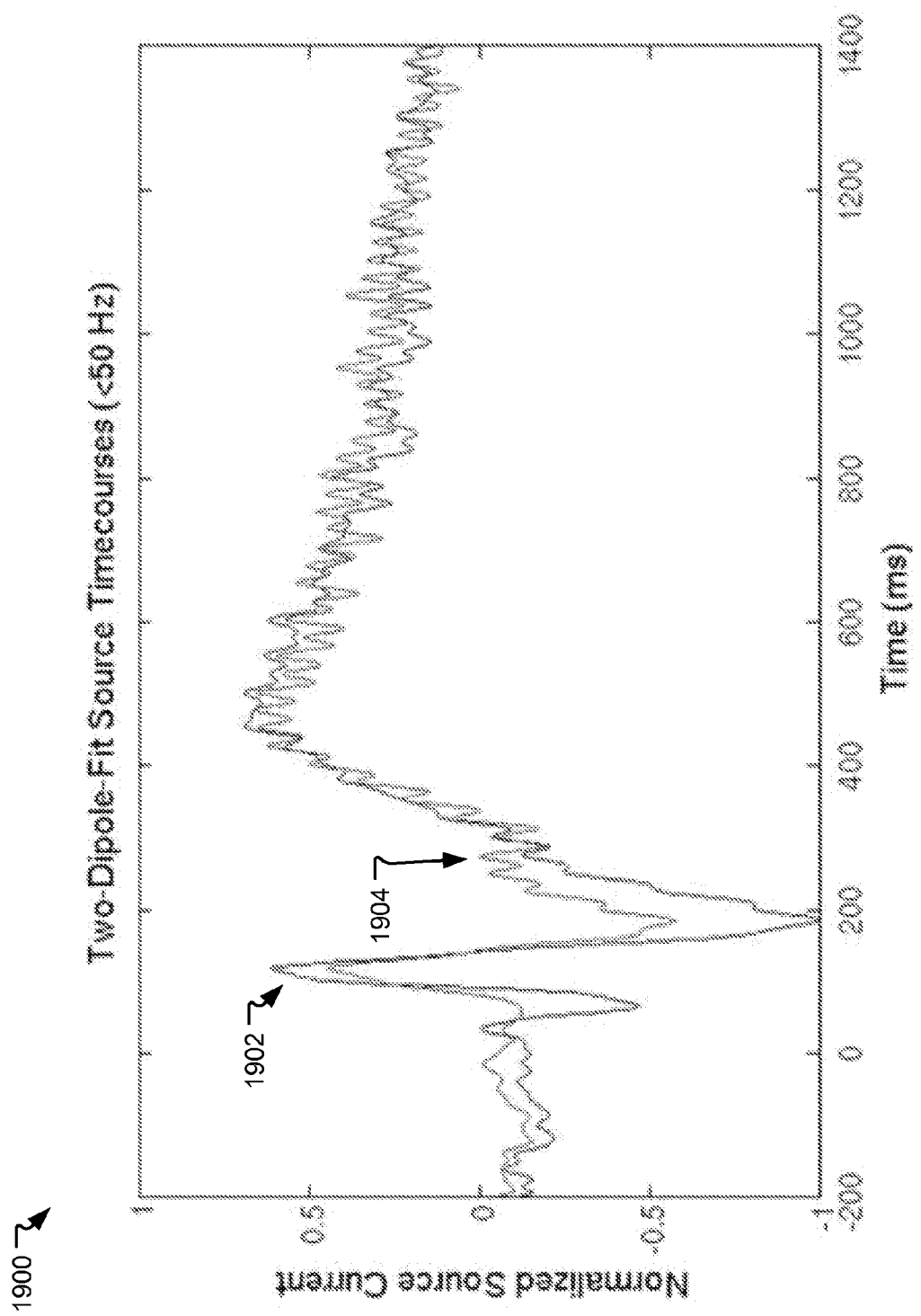
FIG. 19 shows Normalized dipole-fit source time-course reconstruction. Reconstruction of time courses shows a transient and steady-state response in both left (blue) and right (green) auditory cortices. The left transient response is higher in amplitude, while the right 40-Hz steady-state oscillations are more pronounced.

Human Auditory Reconstruction Results:

The two-dipole-fit reconstruction of the evoked MEG auditory response to the 500-Hz pure tone with a 40-Hz envelope (FIG. 19) showed bilateral activation of both the left and right auditory cortices. FIG. 19 shows Normalized dipole-fit source time-course reconstruction 1900. Reconstruction of time courses shows a transient and steady-state response in both left (blue) 1902 and right (green) 1904 auditory cortices. The left transient response is higher in amplitude, while the right 40-Hz steady-state oscillations are more pronounced. The left hemisphere neuronal source (blue) 1902 showed a large transient response followed by a steady-state response with a weak 40-Hz component. The right hemisphere neuronal source (green) 1904 revealed a slightly smaller transient response with strong 40-Hz steady-state oscillations from 500 ms to 1400 ms.

Figure 20:
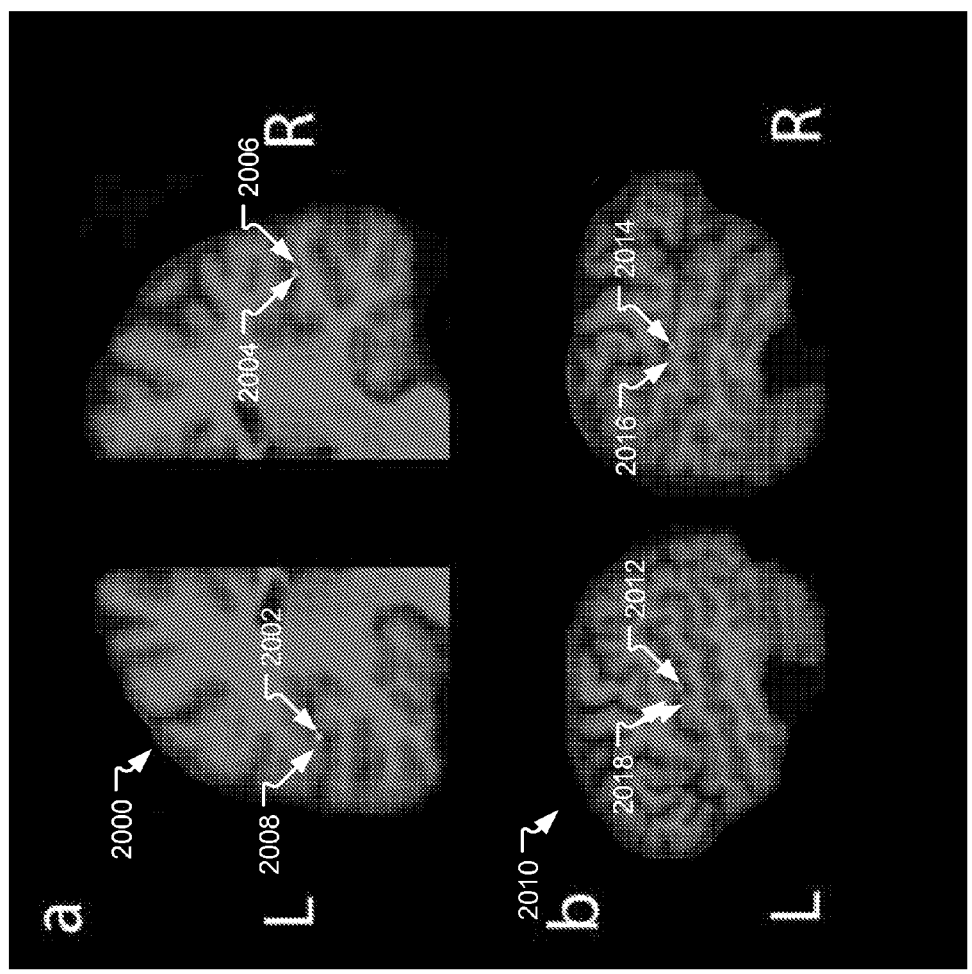
FIG. 20 shows: a) Coronal view of left and right auditory response localization; and b) Sagittal view of left and right auditory response localization. Green—eDCBF localization. Red—dipole-fit localization.
Figure 21:
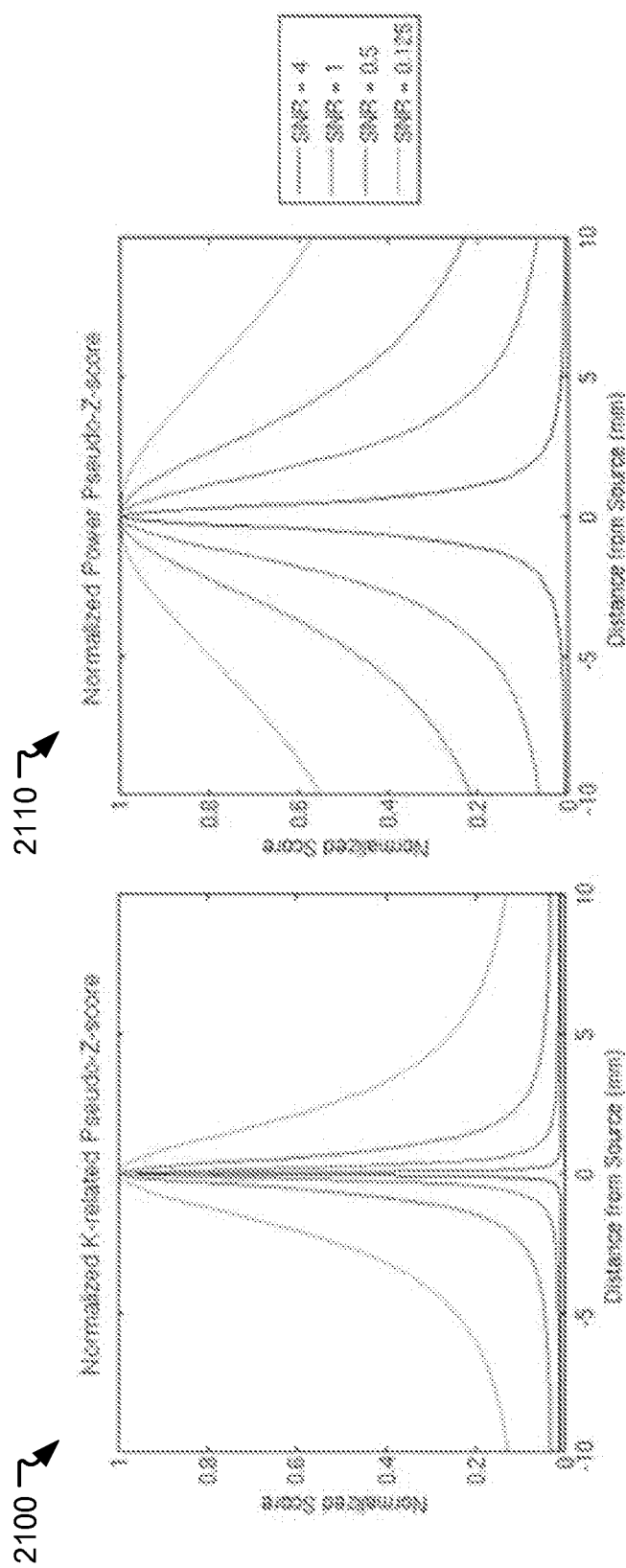
FIG. 21 shows SNR dependence of pseudo-Z-scores. Left Panel—The K-related pseudo-Z-score peaks sharply at high SNR but provides a reasonable profile for localization at lower SNR. Right Panel—The power pseudo-Z-score has much broader peaks, providing an appropriate tool for localization in evoked recordings.

During eDCBF reconstruction of the auditory response, maximizing the power pseudo-Z-score (45) appropriately localized sources to the left and right auditory cortices (FIG. 20). FIG. 20 shows a) Coronal view of left and right auditory response localization 2000; and b) Sagittal view of left and right auditory response localization 2010. Green (2002, 2004, 2012 and 2014)—eDCBF localization. Red (2008, 2006, 2016 and 2018)—dipole-fit localization. Though the K-related pseudo-Z-score provides a valid method of localization at low SNRs as shown previously, its spatial distribution at high SNR is sharply peaked, rendering it unsuitable for grid spacing of a few millimeters. However, the power pseudo-Z-score provides a suitable measure of detection for high SNR recordings (FIG. 21). FIG. 21 shows SNR dependence of pseudo-Z-scores (2100 and 2110). Left Panel (2100)—The K-related pseudo-Z-score peaks sharply at high SNR but provides a reasonable profile for localization at lower SNR. Right Panel (2110)—The power pseudo-Z-score has much broader peaks, providing an appropriate tool for localization in evoked recordings. Localization of the auditory response found by dipole-fit and the eDCBF differed by less than 2.5 mm for each hemisphere (FIG. 20).

Figure 22:
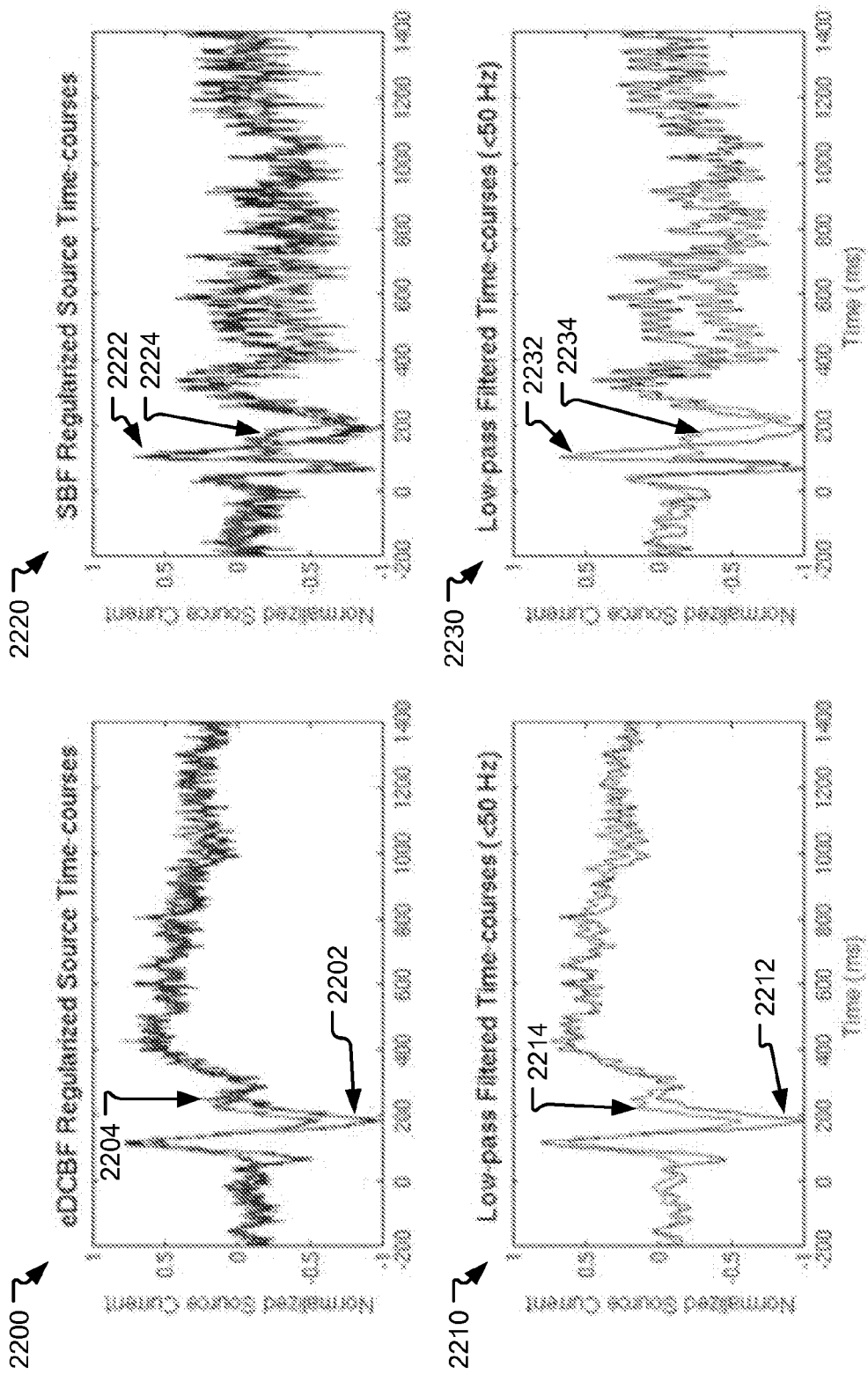
FIG. 22 shows Normalized eDCBF and SBF source time-course reconstruction. eDCBF reconstruction of time courses shows a transient and steady-state response in both left (blue) and right (green) auditory cortices. The left transient response was higher in amplitude while the right steady-state response was more visible. SBF reconstruction of time courses shows distortion and features that are difficult to identify.

Figure shows normalized eDCBF (2200 and 2210) and SBF (2220 and 2230) source time-course reconstruction. eDCBF reconstruction of time courses shows a transient and steady-state response in both left (blue: 2202, 2212, 2222, 2232) and right (green: 2204, 2214, 2224, 2234) auditory cortices. The left transient response was higher in amplitude while the right steady-state response was more visible. SBF reconstruction of time courses shows distortion and features that are difficult to identify. The eDCBF regularized recovery of source time-courses (FIG. 22—left panels 2200 and 2210) showed individual signals for the left (blue: 2202, 2212, 2222, 2232) and right (green: 2204, 2214, 2224, 2234) hemisphere neuronal sources. Furthermore, examination of both right and left source signals showed well-defined transient and steady-state responses that closely resembled the time courses obtained from dipole-fit as indicated by high correlations ($\chi_L^a$=0.9630; $\chi_R^a$=0.9614). In contrast, SBF regularized time-courses (FIG. 22—right panels 2220 and 2230) correlated poorly with those obtained from dipole-fit ($\chi_L^a$=0.9630; $\chi_L^a$=0.9614). In fact, even features such as the larger, left-sided transient response and the stronger, right-sided 40-Hz steady-state response were preserved with the eDCBF. The errors in the SBF reconstruction were due to inaccurate determination of source orientations and the false assumption that sources are uncorrelated.

Correlations for dipole-fit time-courses showed strong coherence between the left and right auditory cortices ($\chi^a$=0.9535; $\chi_{filt}^a$=0.9567). The eDCBF noise-corrected correlation ($\chi_{reg}^a$=0.9349) and the filtered eDCBF correlation ($\hat\chi_{reg,filt}^a$=0.9385) agreed with these values ($\Delta\chi^a$<3%). However, the SBF-predicted correlation ($\hat\chi$reg,filt$^a$=0.6119) was quite poor ($\Delta\chi^a$≈35%). Correlations computed from eDCBF time-courses and from the appropriate source covariance matrices were identical.

Described in this document is an improved implementation of the above described DCBF, with the enhanced DCBF capable of accurately estimating source amplitudes or produce unique time-courses and correlations to characterize source activity. The eDCBF provides a novel approach designed to reconstruct the source power covariance matrix $R_s$ between multiple sources. With this matrix, individual time-courses and correlations for sources can be determined in low SNR conditions, overcoming the deficits of the DCBF.

Computationally, multiple source beamformers (e.g. DSBF, DCBF, eDCBF) require some searching for the optimum source configuration unlike traditional beamformers. Single beamformers may therefore appear more attractive as quick scanning methods but are less accurate due to the strict assumption of non-correlated sources. Furthermore, unlike beamformer spatial filters that are designed to work in a correlated environment (e.g. NB, CSSM, and AGMN-RUG), the eDCBF requires only a single computation of the weight matrix for accurate correlation determination.

For complex signals, the mathematical formulation of eDCBF flexibly enables examination of correlations in envelopes and frequency bands of interest without too much additional computational load, thereby permitting a more detailed investigation of neuronal communication. Moreover, the eDCBF correlation analysis can be naturally extended to the MCBF spatial filter to account for the presence of multiple correlated sources.

A variety of simulations were conducted to examine the performance of the eDCBF by quantifying the robustness of computed correlations across a range of SNRs (4 to 0.167), source locations, time lags, and waveform shape for two sources. The eDCBF reconstructed correlations with a high degree of accuracy even at a source spacing of only 5 mm. The results also showed that the eDCBF could handle both fully correlated and uncorrelated neuronal sources. Source time-course reconstructions resulted in accurate and individual time-courses regardless of the degree of correlation between sources. Furthermore, the amplitudes of time courses were accurately reproduced irrespective of the correlation between sources, which is a notable shortcoming of previous dual-beamformer approaches. The spatial width of the eDCBF localization peaks using different measures ($Z^K$ and $Z^P$) under different SNR conditions was also investigated. We observed that $Z^K$ provides a suitable width for low SNR data while $Z^P$ is preferable for high SNRs.

As a proof of principle, our investigation of the MCBF spatial filter showed accurate correlation reconstruction across a wide variety of source correlations and SNRs in the presence of three correlated sources. In reality, MEG signals can have many active sources. As such, future developments should include an optimization algorithm to determine the proper MCBF core-number to use for reconstruction, which would prevent inaccurate estimation of source activities due to under-modeling. For example, DCBF localization and pseudo-Z-score statistical thresholding can be used to determine MCBF core-number. Furthermore, typical SNR levels for real recordings must be considered, which limits the MCBF core-size to 8-10 sources in practice.

We also applied the eDCBF spatial filter to human MEG measurements from a stereo auditory tone paradigm to cross-validate reconstruction performance from our simulations. Localization with the power pseudo-Z-score showed activity in both auditory cortices. The SBF and eDCBF reconstructions were compared to a two-dipole-fit reconstruction. The eDCBF time-courses for both right and left hemisphere auditory cortices closely resembled dipole-fit time-courses, maintaining both transient and steady-state components of the signal. In contrast, reconstruction with SBF showed malformed and inaccurate time courses. Source localization with eDCBF was used for SBF reconstruction due to the SBF's inability to properly localize correlated neuronal sources. Inter-hemispheric correlations computed from eDCBF and dipole-fit estimated time-courses were very close; however, the SBF predicted correlation was underestimated, confirming that the eDCBF offers a more robust reconstruction than the SBF in correlated source environments. Furthermore, strong correlation between eDCBF time-courses and dipole-fit results showed that the two methods yield very similar waveforms.

In summary, the present results indicate that the eDCBF spatial filter provides a viable method for exploring complex neuronal networks and their communication, promoting the use of MEG to investigate brain activity.

Figure 23A:
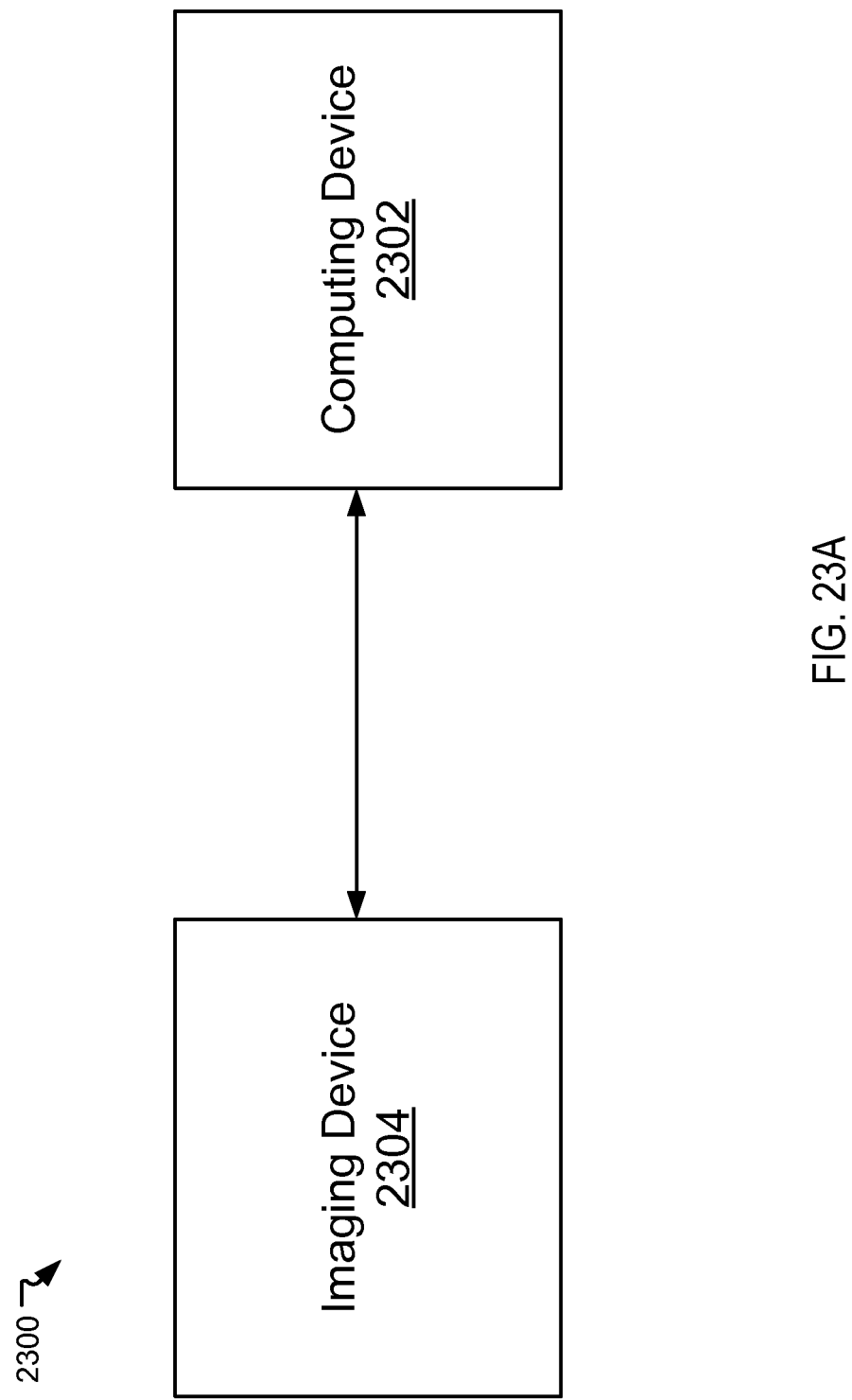
FIGS. 23A and 23B are block diagrams of a computing device 2302 and system 2300 that can be used, e.g., to implement techniques (e.g., DCBF, MCBF, eDCBF and SBF) described in this document.
Figure 23B:
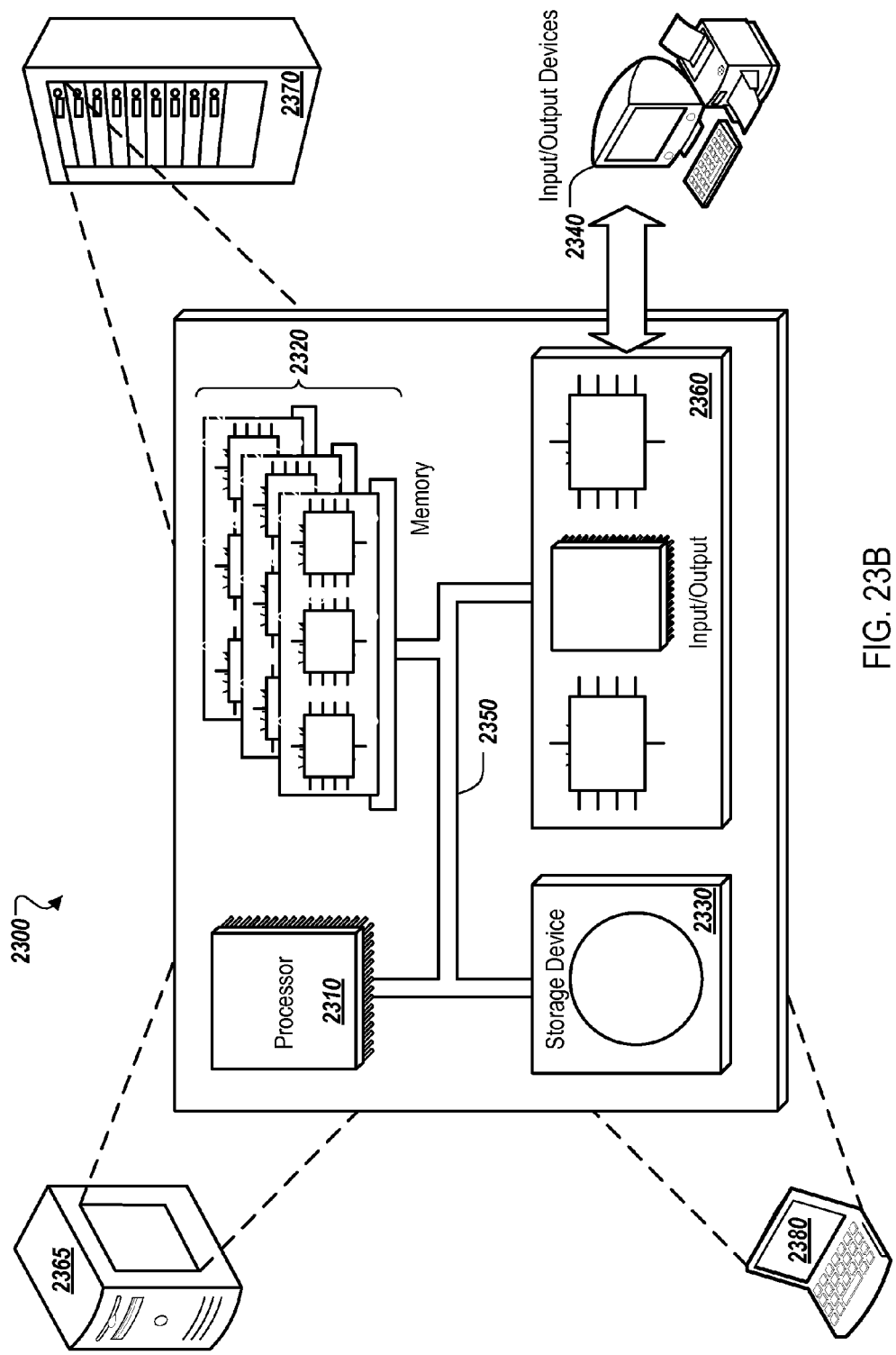

FIGS. 23A and 23B are block diagrams of a computing device 2302 and system 2300 that can be used, e.g., to implement techniques (e.g., DCBF, MCBF, eDCBF and SBF) described in this document. Computing device 2302 is intended to represent various forms of digital computers, such as laptops, desktops, workstations, personal digital assistants, servers, blade servers, mainframes, and other appropriate computers. The components shown here, their connections and relationships, and their functions, are meant to be exemplary only, and are not meant to limit implementations of the inventions described and/or claimed in this document.

The system 2300 can include the computing device 2302 that can interface with an imaging device 2304 to processing the imaging signal (or data) received from the imaging device 2304. The imaging device 2304 can include different types of imaging devices as described in this document including those that can perform MEG, fMRI, etc.

Computing device 2302 includes a processor 2310, memory 2320, a storage device 2330, a high-speed interface 2350 connecting to memory 2320. The computing device can also include high-speed expansion ports (not shown), and a low speed interface (not shown) connecting to low speed bus (not shown) and storage device 2330. Each of the components 2310, 2320, 2330, 2350, and 2320, are interconnected using various busses, and can be mounted on a common motherboard or in other manners as appropriate. The processor 2310 can process instructions for execution within the computing device 2300, including instructions stored in the memory 2320 or on the storage device 2330 to display graphical information for a GUI on an external input/output device, such as display 2340 coupled to an input/output interface 2360. In other implementations, multiple processors and/or multiple buses can be used, as appropriate, along with multiple memories and types of memory. Also, multiple computing devices 2300 can be connected, with each device providing portions of the necessary operations (e.g., as a server bank, a group of blade servers, or a multi-processor system).

The memory 2320 stores information within the computing device 2300. In one implementation, the memory 2320 is a computer-readable medium. In one implementation, the memory 2320 is a volatile memory unit or units. In another implementation, the memory 2320 is a non-volatile memory unit or units.

The storage device 2330 is capable of providing mass storage for the computing device 2300. In one implementation, the storage device 2330 is a computer-readable medium. In various different implementations, the storage device 2330 can be a floppy disk device, a hard disk device, an optical disk device, or a tape device, a flash memory or other similar solid state memory device, or an array of devices, including devices in a storage area network or other configurations. In one implementation, a computer program product is tangibly embodied in an information carrier. The computer program product contains instructions that, when executed, perform one or more methods, such as those described above. The information carrier is a computer- or machine-readable medium, such as the memory 2320, the storage device 2330, memory on processor 2310, or a propagated signal.

The high speed controller 2350 manages bandwidth-intensive operations for the computing device 2300, while the low speed controller manages lower bandwidth-intensive operations. Such allocation of duties is exemplary only. In one implementation, the high-speed controller 2350 is coupled to memory 2320, display 2340 (e.g., through a graphics processor or accelerator), and to high-speed expansion ports (not shown), which can accept various expansion cards (not shown). In the implementation, low-speed controller (not shown) is coupled to storage device 2330 and low-speed expansion port (not shown). The low-speed expansion port, which can include various communication ports (e.g., USB, Bluetooth, Ethernet, wireless Ethernet) can be coupled to one or more input/output devices, such as a keyboard, a pointing device, a scanner, or a networking device such as a switch or router, e.g., through a network adapter.

The computing device 2302 can be implemented in a number of different forms, as shown in the figure. For example, it can be implemented as a standard server 2365, or multiple times in a group of such servers. It can also be implemented as part of a rack server system 2370. In addition, it can be implemented in a personal computer such as a laptop computer 2380.

Embodiments of the subject matter and the functional operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer program products, i.e., one or more modules of computer program instructions encoded on a tangible program carrier for execution by, or to control the operation of, data processing apparatus. The tangible program carrier can be a propagated signal or a computer readable medium. The propagated signal is an artificially generated signal, e.g., a machine-generated electrical, optical, or electromagnetic signal, that is generated to encode information for transmission to suitable receiver apparatus for execution by a computer. The computer readable medium can be a machine-readable storage device, a machine-readable storage substrate, a memory device, a composition of matter effecting a machine-readable propagated signal, or a combination of one or more of them.

The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, or declarative or procedural languages, and it can be deployed in any form, including as a stand alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device.

Non-transitory computer readable media suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, input from the user can be received in any form, including acoustic, speech, or tactile input.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described is this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While this specification contains many specifics, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments.

Only a few implementations and examples are described and other implementations, enhancements and variations can be made based on what is described and illustrated in this application and attached Appendix.

What is claimed is:

1. A method of implementing a multi-core beamformer (MCBF) lead-field based inverse-modeling technique designed for simultaneously reconstructing highly-correlated and uncorrelated source dipoles from a sensor array, comprising:

combining a plurality of lead-field vectors for a plurality of source dipoles, without knowledge of locations of the plurality of source dipoles, into a multi-core spatial filter matrix, wherein each of the plurality of lead-field vectors contains information of a number of sensors in three orientations for a corresponding source dipole;

constructing a second matrix that is inversely proportional to a source power of the plurality of source dipoles using the multi-core spatial filter matrix and a covariant matrix of sensor signals that are generated by the sensor array;

obtaining a beamformer power and a weighting in each of the three orientations of the plurality of source dipoles by decomposing the second matrix;

constructing a plurality of time-courses for the plurality of source dipoles using the second matrix, the beamformer power, the covariant matrix of sensor signals, and the multi-core spatial filter matrix;

obtaining data from magnetoencephalography for combining with the plurality of time-courses for diagnosis; and decomposing each of the plurality of lead-field vectors to contain information of a number of sensors in two orientations for a corresponding source dipole.

2. The method of claim 1, wherein the sensor arrays include radar, sonar, astronomical telescopes, magnetotelluric sensors, optical or other electromagnetic arrays.

3. The method of claim 1, further comprising reconstructing a correlation between the plurality of source dipoles by computing a plurality of source power covariant matrices based on the second matrix.

4. The method of claim 3, further comprising: using the correlation to perform regional connectivity analysis to localize abnormal neuronal networks using data from magnetoencephalography (MEG) to provide more sensitive diagnosis than conventional neuroimaging techniques for neurological and psychiatric disorders comprising at least one of 1) traumatic brain injury (TBI), 2) stroke, 3) Post-Traumatic Stress Disorder (PTSD), 4) schizophrenia, 5) Alzheimer's dementia, or 6) Autism.

5. The method of claim 1, further comprising:
constructing a third matrix that is inversely proportional to a signal-to-noise ratio (SNR) for the plurality of source dipoles, and
obtaining a measurement of relative source activity for the plurality of source dipoles based on the third matrix.

6. The method of claim 5, further comprising using the measurement of relative source activity to perform regional connectivity analysis to localize abnormal neuronal networks using data from magnetoencephalography (MEG) to provide more sensitive diagnosis than conventional neuroimaging techniques for neurological and psychiatric disorders comprising at least one of 1) traumatic brain injury (TBI), 2) stroke, 3) Post-Traumatic Stress Disorder (PTSD), 4) schizophrenia, 5) Alzheimer's dementia, or 6) Autism.

7. The method of claim 1, wherein the decomposing the second matrix includes performing a singular value decomposition of the second matrix.

8. The method of claim 1, wherein the obtaining step is performed by using a search process in which a search is made for best combination of a first dipole and a second dipole of the sensor array by independently searching along two coordinate axes.

* * * * *